US011299460B2

(12) United States Patent
Wang et al.

(10) Patent No.: US 11,299,460 B2
(45) Date of Patent: Apr. 12, 2022

(54) MDM2 INHIBITOR, PREPARATION METHOD THEREFOR, PHARMACEUTICAL COMPOSITION THEREOF AND USE THEREOF

(71) Applicant: SHANGHAI LONGWOOD BIOPHARMACEUTICALS CO., LTD., Shanghai (CN)

(72) Inventors: Zhe Wang, Shanghai (CN); Zhihong Zeng, Shanghai (CN); Rongzhen Jiang, Shanghai (CN)

(73) Assignee: Shanghai Longwood Biopharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 17/281,368

(22) PCT Filed: Sep. 30, 2019

(86) PCT No.: PCT/CN2019/109428
§ 371 (c)(1),
(2) Date: Mar. 30, 2021

(87) PCT Pub. No.: WO2020/064004
PCT Pub. Date: Apr. 2, 2020

(65) Prior Publication Data

US 2022/0002248 A1 Jan. 6, 2022

(30) Foreign Application Priority Data

Sep. 30, 2018 (CN) ........................ 201811160163.0

(51) Int. Cl.
*C07D 211/74* (2006.01)

(52) U.S. Cl.
CPC .................................. *C07D 211/74* (2013.01)

(58) Field of Classification Search
CPC .................................................. C07D 211/74
See application file for complete search history.

(56) References Cited

U.S. PATENT DOCUMENTS

2014/0235629 A1* 8/2014 Bartberger .............. A61P 35/02
514/230.8

FOREIGN PATENT DOCUMENTS

| | | | |
|---|---|---|---|
| CN | 103180296 | A | 6/2013 |
| CN | 105121407 | A | 12/2015 |
| CN | 105358530 | A | 2/2016 |

OTHER PUBLICATIONS

International Search Report dated Dec. 27, 2019 in PCT/CN2019/109428.
Written Opinion dated Dec. 27, 2019 in PCT/CN2019/109428.
Wang, Yingcai et al., "Optimization beyond AMG 232: Discovery and SAR of Sulfonamides on a Piperidinone Scaffold as Potent Inhibitors of the MDM2-p53 Protein-Protein Interaction," Bioorganic & Medicinal Chemistry Letters, vol. 24, No. 16, Jul. 1, 2014, pp. 3782-3785.
Gonzalez, A.Z., et al., "Novel Inhibitors of the MDM2-p53 Interaction Featuring Hydrogen Bond Acceptors as Carboxylic Acid Isosteres," Journal of Medicinal Chemistry, vol. 57, No. 7, Mar. 6, 2014, pp. 2963-2988.

* cited by examiner

*Primary Examiner* — Timothy R Rozof
(74) *Attorney, Agent, or Firm* — Ice Miller LLP

(57) ABSTRACT

The present invention relates to an MDM2 inhabitor, a preparation method therefor, a pharmaceutical composition thereof, and the use thereof specifically, the present invention relates to a compound represented by formula I. The compound has excellent MDM2 inhibitory activities, and can be used for preparing a pharmaceutical composition for treating cancers and other diseases related to MDM2 activities, particularly p53 wild-type cancer.

I

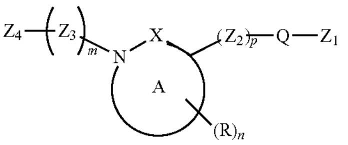

10 Claims, No Drawings

MDM2 INHIBITOR, PREPARATION METHOD THEREFOR, PHARMACEUTICAL COMPOSITION THEREOF AND USE THEREOF

CROSS-REFERENCE TO RELATED APPLICATION

This application is a Section 371 of International Application No. PCT/CN2019/109428 filed Sep. 30, 2019, which was published in the Chinese language Apr. 2, 2020, under International Publication No. WO 2020/064004 A1, which claims priority to Chinese Application No. 201811160163.0 filed Sep. 30, 2018, the disclosures of which are incorporated herein by reference in their entireties.

FIELD OF THE INVENTION

The present invention relates to the field of small molecular drugs. Specifically, provided herein is an MDM2 inhibitor, a preparation method therefor, a pharmaceutical composition thereof, and the use thereof.

BACKGROUND OF THE INVENTION

Gene p53 is a tumor suppressor gene with the highest correlation with human tumor which has functions such as maintaining genomic stability, inhibiting or preventing cell transformation, thus inhibiting the occurrence of tumor. The research of new anti-tumor drug targeting gene p53 has become a hotpot of the field. Results suggest that MDM2 (murine double minute 2) is the key negative regulator of gene p53. Gene p53 activates the transcription of MDM2, while MDM2 in turn suppresses the activity of gene p53, thus forming an auto-regulating feedback loop to keep both gene p53 and MDM2 at low level under normal conditions. The abnormal expression of MDMD2 in tumor cells causes rapid degredation of gene p53 and inactivity of gene p53 pathway, which affects tumor inhibition. Therefore, releasing gene p53 from the manipulation of MDM2 and activating gene p53 pathway are expected to inhibit tumor proliferation and induce apoptosis. Unlike normal activation of gene p53 inflicted by uncommon causes, tumor cells are under continuous cellular stress of damages including hypoxia and activation of pro-apoptotic oncogenes. Thus, the inactivation of gene p53 pathway has a strong selective advantage. Researchers also suggest that the elimination of gene p53 function may be the premise for tumor survival. To confirm this hypothesis, three research teams have confirmed with mice model that the loss of gene p53 function is the persistant requirement of tumor maintenance. Gene p53 inactivated tumor was found reduced after restoring gene p53 function.

In 50% solid tumors and 10% liquid tumors, gene p53 was inactivated by mutation and/or deletion. In cancer, other members of gene p53 pathway also undergo genetic or epigenetic changes. As a carcinoma protein, MDM2 inhibits the function of gene p53. Researches show that MDM2 can be activated by gene amplification with an incidence of up to 10%. MDM2 can be inhibited by another tumor inhibitor p14ARF. Downstream alterations of gene p53 are thought to deactivate at least some part of wild-type gene p53 pathways. As a support of the idea, some tumors with wild-type gene p53 demonstrate has shown lower apoptotic function, but their ability to sustain stagnant cell circle remains intact. There is a tumor treatment that involves small molecule binding MDM2 and counter-balancing the interaction thereof with gene p53. MDM2 inhibits the activation of gene p53 through three mechanisms: 1) promoting degredation of gene p53 with E3 ubiquitin ligase; 2) binding to gene p53 transactivation domain and blocking transactivation domain; 3) exporting P53 from nucleus to cytoplasm. All three mechanisms can be blocked through offsetting the interaction between MDM2 and gene p53. This therapeutic strategy can be applied to tumors with wild-type gene p53, and studies have shown that small molecule MDM2 inhibitor is expected to reduce tumor growth both in vitro and in vivo. Furthermore, in patients with deactivated gene p53 tumor, the inhibition of MDM2 stabilizes wild-type gene p53 in normal tissue, thus selectively protecting normal tissues.

In summary, there is an urgently need in the field to develop novel MDM2 inhibitor.

BRIEF SUMMARY OF THE INVENTION

The purpose of the present invention is to provide a novel MDM2 inhibitor.

In the first aspect of the present invention, a compound according to the Formula I:

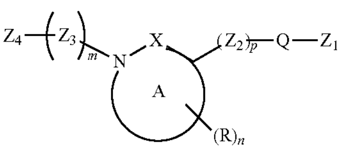

I or stereoisomers or tautomers thereof, or pharmaceutically acceptable salts, hydrates or solvates thereof is provided, wherein,

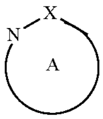

is selected from the group consisting of 5, 6 or 7 membered heterocyclic with 1-3 N and 0-2 heteroatoms selected from S and O;

X is C═O or S═$(O)_2$;

n is 1, 2, 3 or 4;

each R is selected independently from the group consisting of H, cyano, halogen, substituted or unsubstituted $C_1$-$C_6$ alkyl, substituted or unsubstituted $C_1$-$C_6$ alkoxy, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O;

$Z_1$ is selected from the group consisting of H, substituted or unsubstituted $C_1$-$C_6$ alkyl, substituted or unsubstituted $C_1$-$C_6$ alkoxy, substituted or unsubstituted $C_3$-$C_8$ cycloalkyl (including single, fused or bridged ring), substituted or unsubstituted $C_6$-$C_{10}$ aryl;

Q is selected from the group consisting of

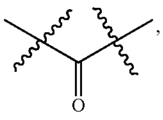,
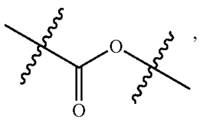,

-continued

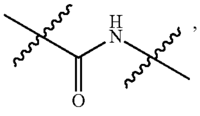

,

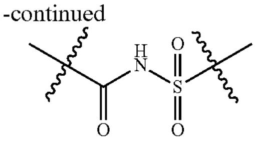

or

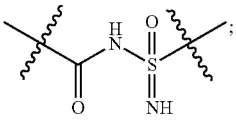

;

M and p are selected independently from the group consisting of 1, 2, 3 or 4;

Each $Z_2$ and $Z_3$ is selected independently from the group consisting of none, substituted or unsubstituted $C_1$-$C_7$ alkylidene, $NR_1$, O, S, C═O, S═$(O)_2$;

$Z_4$ is selected from

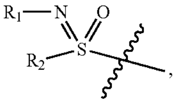

,

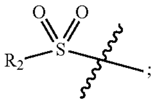

;

wherein, $R_1$ is selected from the group consisting of H, substituted or unsubstituted $C_1$-$C_6$ alkyl, substituted or unsubstituted $C_6$-$C_{10}$ aryl, CN, —C(═O)—NRdRe, —C(═O)— substituted or unsubstituted $C_1$-$C_6$ alkoxy, —C(═O)— substituted or unsubstituted $C_1$-$C_6$ alkyl, —C(═O)— substituted or unsubstituted $C_3$-$C_{10}$ cycloalkyl, —C(═O)— substituted or unsubstituted $C_2$-$C_6$ alkenyl, —C(═O)— substituted or unsubstituted $C_2$-$C_6$ alkynyl;

Rd and Re are selected independently from the group consisting of H, substituted or unsubstituted $C_1$-$C_6$ alkyl, substituted or unsubstituted $C_3$-$C_8$ cycloalkyl, substituted or unsubstituted $C_6$-$C_{10}$ aryl; the Rd and Re herein form a 4-10 membered heterocyclic with adjacent N, and the heterocyclic contains 1-2 N and 0-2 S or O.

$R_2$ is selected from the group consisting of substituted or unsubstituted $C_1$-$C_6$ alkyl, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O.

Unless otherwise specified, "substituted" refers to being substituted by one or more (for example, 2, 3, 4, etc.) substituents selected from the group consisting of halogen, $C_1$-$C_6$ alkyl, halogenated $C_1$-$C_6$ alkyl, $C_1$-$C_6$ alkoxy, halogenated $C_1$-$C_6$ alkoxy, $C_3$-$C_8$ cycloalkyl, halogenated $C_3$-$C_8$ cycloalkyl, oxo, —CN, hydroxy, —$NH_2$, carboxy, unsubstituted or substituted group selected from the group consisting of $C_6$-$C_{10}$ aryl, halogenated $C_6$-$C_{10}$ aryl, 5-10 membered heteroaryl with 1-3 heteroatoms selected from N, S, O; halogenated 5-10 membered heteroaryl with 1-3 heteroatoms selected from N, S, or O; and the substituted means substituted by groups selected from the group consisting of halogen, $C_1$-$C_6$ alkoxy;

with the proviso that, when $Z_4$ being

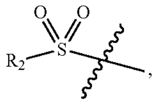

, then Q is

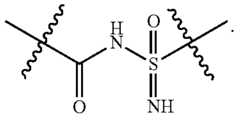 [SMILES: *C(=O)NS(*)(=N)=O]

.

In a preferred embodiment

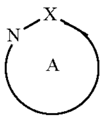

is

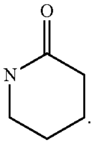

.

In a preferred embodiment, the compound of Formula I has a structure according to Formula II:

II

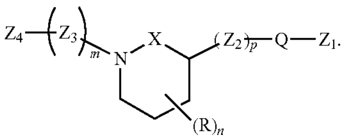

.

In a preferred embodiment, n is 3.

In a preferred embodiment, R is selected from the group consisting of substituted or unsubstituted $C_1$-$C_6$ alkyl, substituted or unsubstituted $C_6$-$C_{10}$ aryl.

In a preferred embodiment, the compound of Formula I has a structure according to Formula III:

III

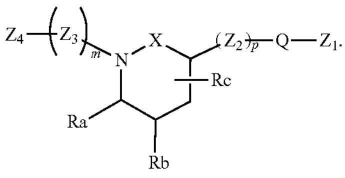

.

wherein, Ra and Rb are selected independently from substituted or unsubstituted $C_6$-$C_{10}$ aryl and 5-10 membered heteroaryl with 1-3 heteroatoms selected from N, S, or O;

Rc is selected from the group consisting of H, CN, halogen, substituted or unsubstituted C1-C6 alkyl, substituted or unsubstituted C1-C6 alkoxy;

each group is defined as above.

In a preferred embodiment, Ra and Rb are independently selected from substituted or unsubstituted phenyl.

In a preferred embodiment, the compound of Formula I has a structure according to Formula IV:
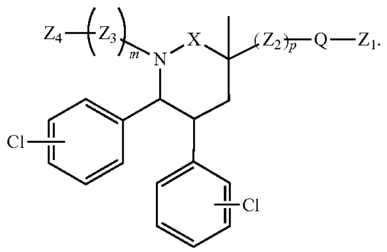
IV
In a preferred embodiment, the compound of Formula I have a structure selected from table A.
TABLE A
| number | structure |
|---|---|
| 001 | 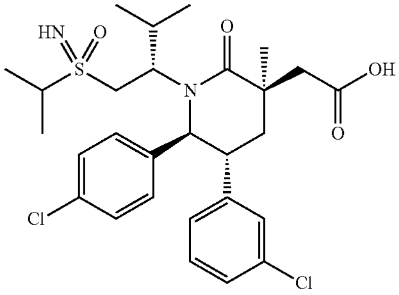 isomer with high TLC polarity |
| 002 | 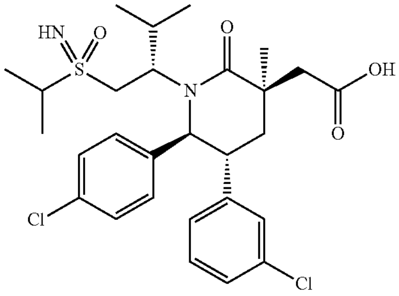 isomer with low TLC polarity |
| 003 | 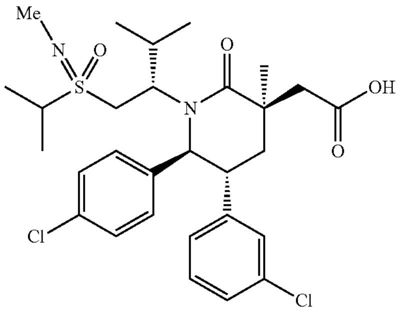 isomer with low TLC polarity |

TABLE A-continued
| number | structure |
|---|---|
| 004 | 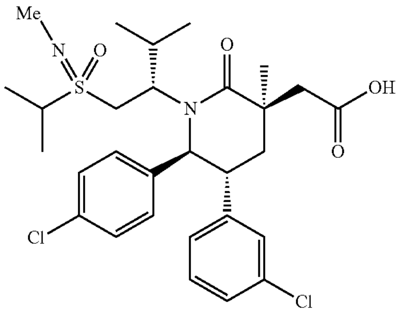 isomer with high TLC polarity |
| 005 | 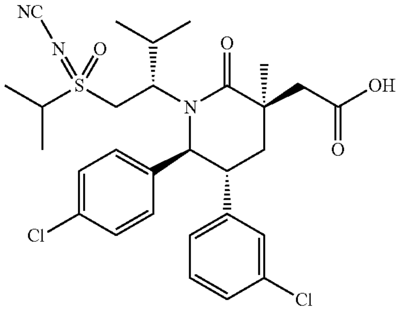 peak 1 isomer in HPLC |
| 006 | 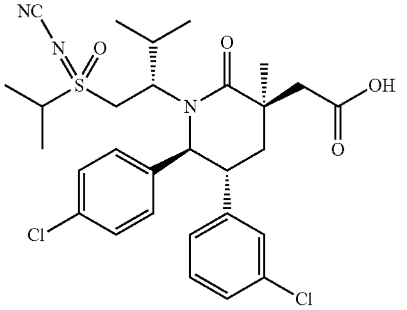 peak 2 isomer in HPLC |
| 007 | 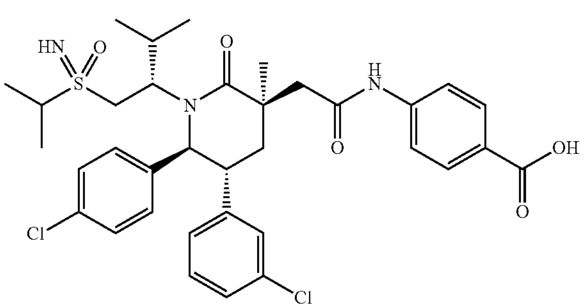 [SMILES: CC(C)[C@@H](CS(=N)(=O)C(C)C)N1C(=O)[C@@](C)(CC(=O)Nc2ccc(C(=O)O)cc2)C[C@H](c2cccc(Cl)c2)[C@H]1c1ccc(Cl)cc1] |

TABLE A-continued
| number | structure |
|---|---|
| 008 | 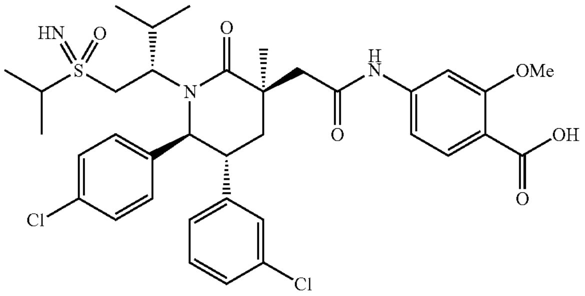 [SMILES: COc1cc(NC(=O)C[C@@]2(C)C[C@H](c3cccc(Cl)c3)[C@@H](c3ccc(Cl)cc3)N([C@H](CS(=N)(=O)C(C)C)C(C)C)C2=O)ccc1C(=O)O] |
| 009 | 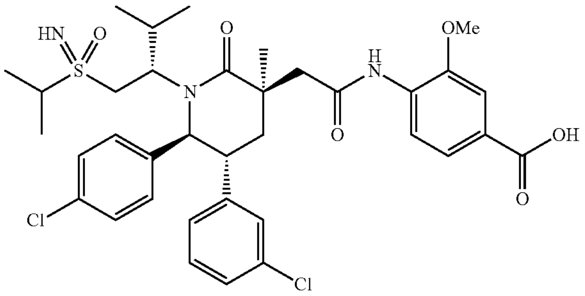 [SMILES: COc1cc(C(=O)O)ccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] |
| 010 | 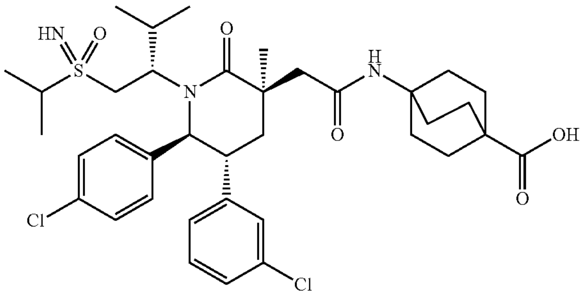 [SMILES: CC(C)[C@@H](CS(=N)(=O)C(C)C)N1C(=O)[C@@](C)(CC(=O)NC23CCC(C(=O)O)(CC2)CC3)C[C@H](c2cccc(Cl)c2)[C@H]1c1ccc(Cl)cc1] |
| 011 | 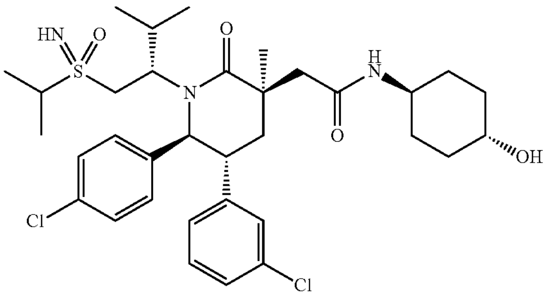 [SMILES: CC(C)[C@@H](CS(=N)(=O)C(C)C)N1C(=O)[C@@](C)(CC(=O)N[C@H]2CC[C@H](O)CC2)C[C@H](c2cccc(Cl)c2)[C@H]1c1ccc(Cl)cc1] |
| 012 | 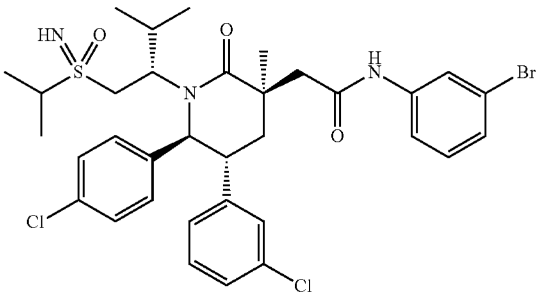 [SMILES: CC(C)[C@@H](CS(=N)(=O)C(C)C)N1C(=O)[C@@](C)(CC(=O)Nc2cccc(Br)c2)C[C@H](c2cccc(Cl)c2)[C@H]1c1ccc(Cl)cc1] |

TABLE A-continued
| number | structure |
|---|---|
| 013 | 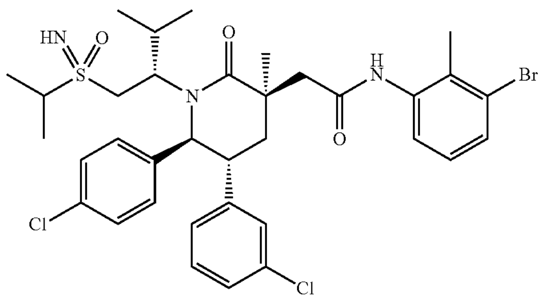 [SMILES: Cc1c(Br)cccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] |
| 014 | 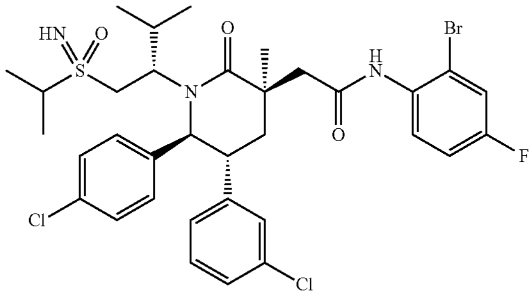 [SMILES: CC(C)[C@@H](CS(=N)(=O)C(C)C)N1C(=O)[C@@](C)(CC(=O)Nc2ccc(F)cc2Br)C[C@H](c2cccc(Cl)c2)[C@H]1c1ccc(Cl)cc1] |
| 015 | 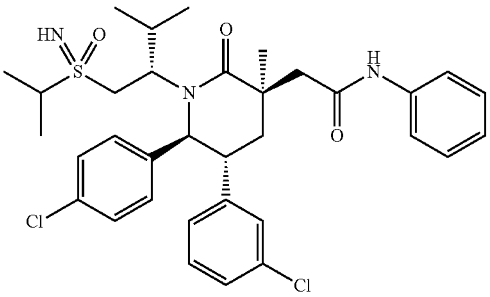 [SMILES: CC(C)[C@@H](CS(=N)(=O)C(C)C)N1C(=O)[C@@](C)(CC(=O)Nc2ccccc2)C[C@H](c2cccc(Cl)c2)[C@H]1c1ccc(Cl)cc1] |
| 016 | 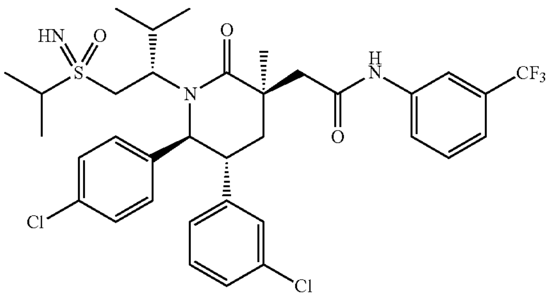 [SMILES: CC(C)[C@@H](CS(=N)(=O)C(C)C)N1C(=O)[C@@](C)(CC(=O)Nc2cccc(C(F)(F)F)c2)C[C@H](c2cccc(Cl)c2)[C@H]1c1ccc(Cl)cc1] |
| 017 | 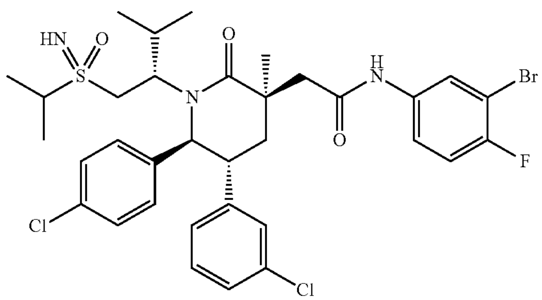 [SMILES: CC(C)[C@@H](CS(=N)(=O)C(C)C)N1C(=O)[C@@](C)(CC(=O)Nc2ccc(F)c(Br)c2)C[C@H](c2cccc(Cl)c2)[C@H]1c1ccc(Cl)cc1] |

TABLE A-continued
| number | structure |
|---|---|
| 018 | 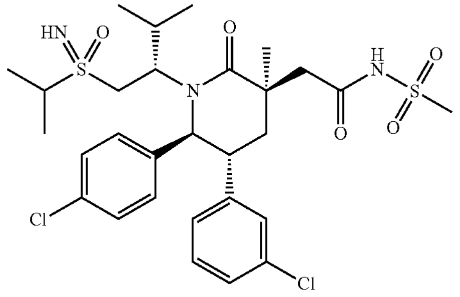 (R configuration and S configuration) |
| 019 | 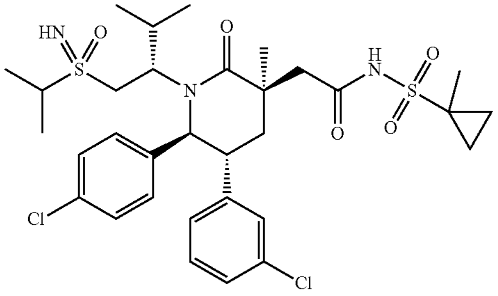 (R configuration and S configuration) |
| 020 | 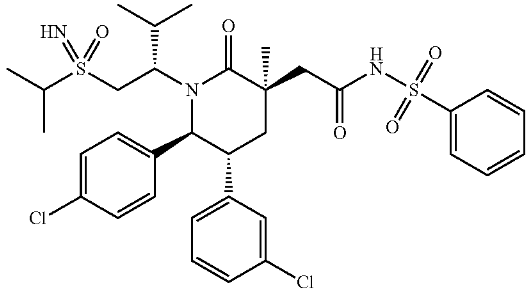 [SMILES: CC(C)[C@@H](CS(=N)(=O)C(C)C)N1C(=O)[C@@](C)(CC(=O)NS(=O)(=O)c2ccccc2)C[C@H](c2cccc(Cl)c2)[C@H]1c1ccc(Cl)cc1] |
| 021 | 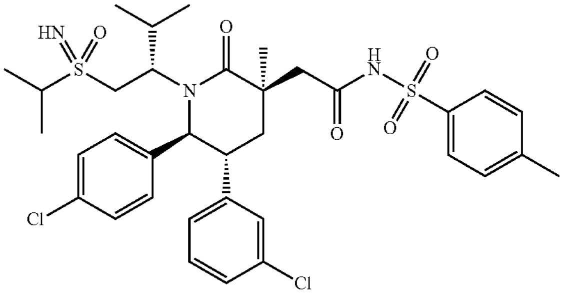 [SMILES: Cc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] |
| 022 | 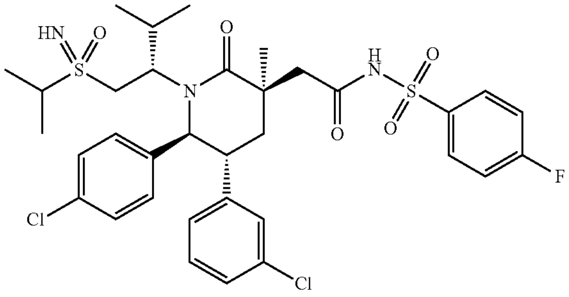 [SMILES: CC(C)[C@@H](CS(=N)(=O)C(C)C)N1C(=O)[C@@](C)(CC(=O)NS(=O)(=O)c2ccc(F)cc2)C[C@H](c2cccc(Cl)c2)[C@H]1c1ccc(Cl)cc1] |

TABLE A-continued
| number | structure |
|---|---|
| 023 | 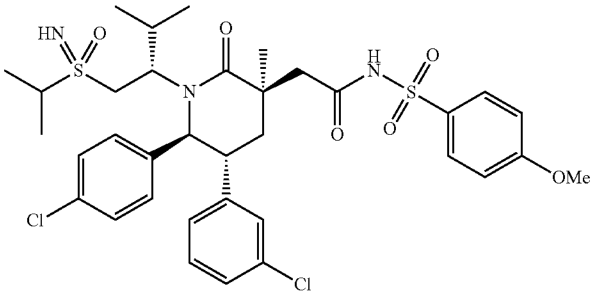 [SMILES: COc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] |
| 024 | 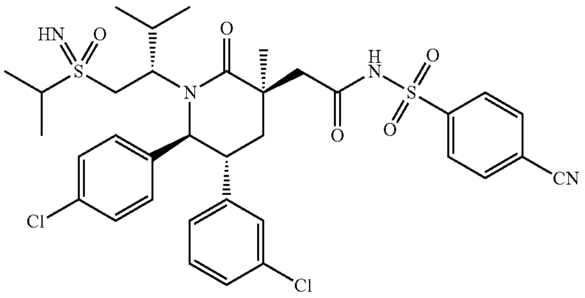 [SMILES: CC(C)[C@@H](CS(=N)(=O)C(C)C)N1C(=O)[C@@](C)(CC(=O)NS(=O)(=O)c2ccc(C#N)cc2)C[C@H](c2cccc(Cl)c2)[C@H]1c1ccc(Cl)cc1] |
| 025 | 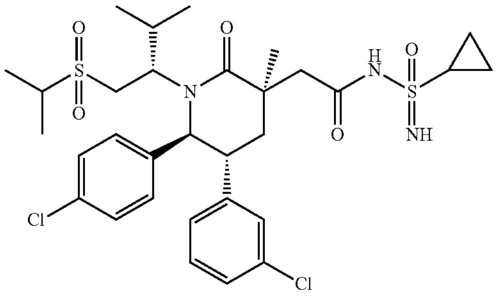 [SMILES: CC(C)[C@@H](CS(=O)(=O)C(C)C)N1C(=O)[C@@](C)(CC(=O)NS(=N)(=O)C2CC2)C[C@H](c2cccc(Cl)c2)[C@H]1c1ccc(Cl)cc1] |
| 028A | 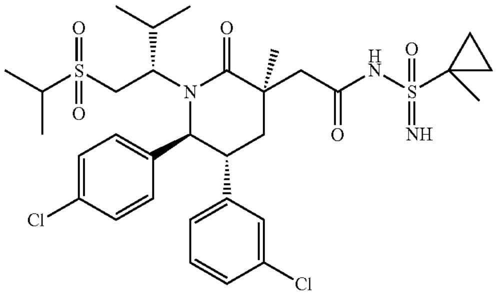<br>peak 1 isomer in HPLC |
| 028B | 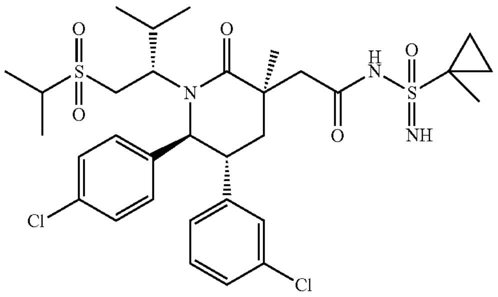<br>peak 2 isomer in HPLC |

TABLE A-continued
| number | structure |
|---|---|
| 029 | 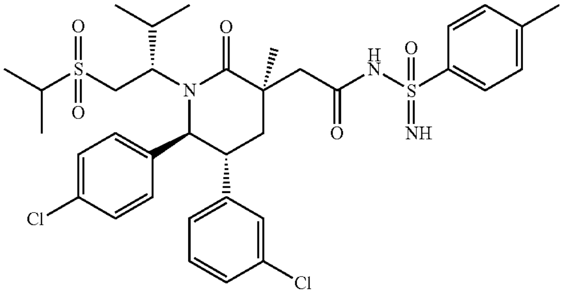 [SMILES: Cc1ccc(S(=N)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1] |
| 030 | 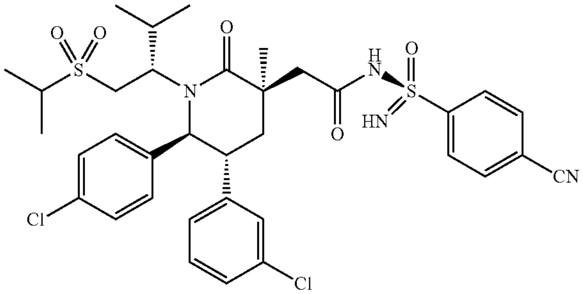 [SMILES: CC(C)[C@@H](CS(=O)(=O)C(C)C)N1C(=O)[C@@](C)(CC(=O)N[S@@](=N)(=O)c2ccc(C#N)cc2)C[C@H](c2cccc(Cl)c2)[C@H]1c1ccc(Cl)cc1] |
| 031 | 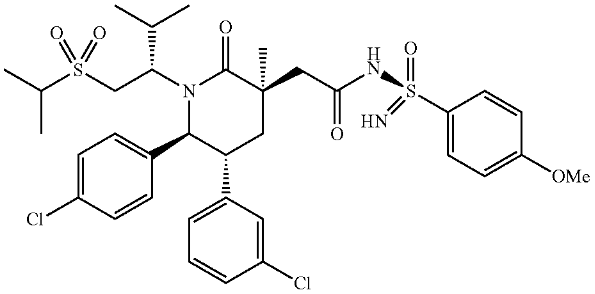 [SMILES: COc1ccc([S@](=N)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1] |
| 034 | 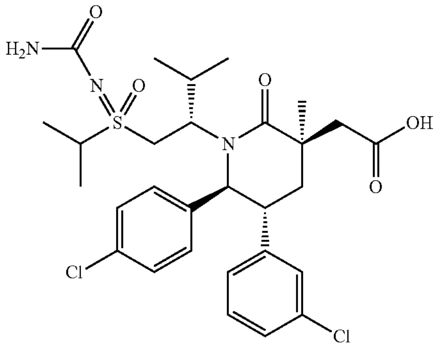 |
| 035 | 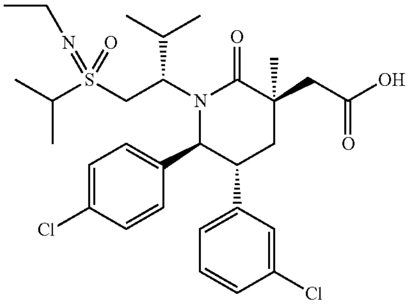 [SMILES: CCN=S(=O)(C[C@H](C(C)C)N1C(=O)[C@@](C)(CC(=O)O)C[C@H](c2cccc(Cl)c2)[C@H]1c1ccc(Cl)cc1)C(C)C] |

TABLE A-continued
| number | structure |
| --- | --- |
| 039 | 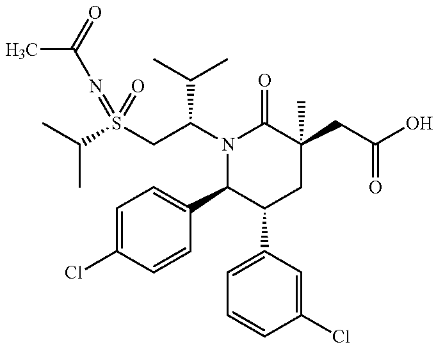 [SMILES: CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] |
| 040 | 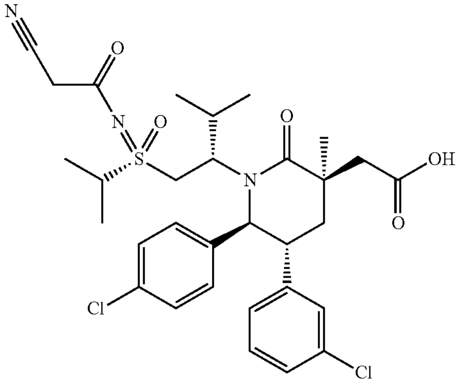 [SMILES: CC(C)[C@@H](C[S@](=O)(=NC(=O)CC#N)C(C)C)N1C(=O)[C@@](C)(CC(=O)O)C[C@H](c2cccc(Cl)c2)[C@H]1c1ccc(Cl)cc1] |
| 041 | 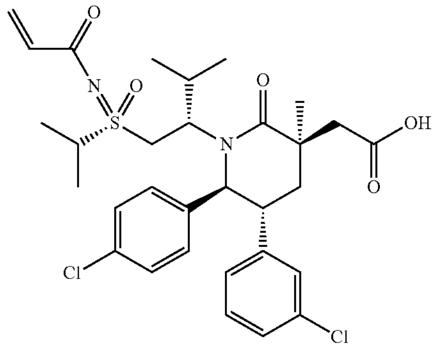 [SMILES: C=CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] |
| 042 | 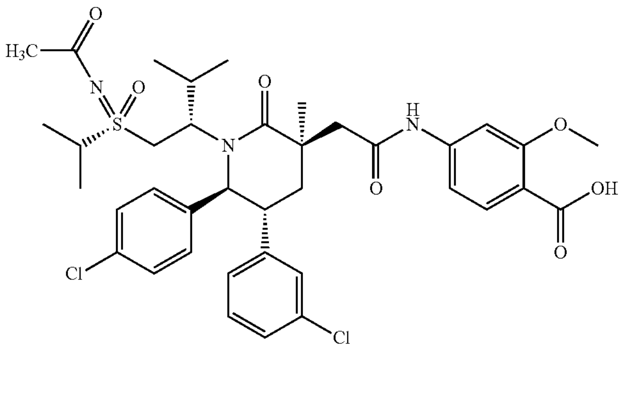 [SMILES: COc1cc(NC(=O)C[C@@]2(C)C[C@H](c3cccc(Cl)c3)[C@@H](c3ccc(Cl)cc3)N([C@H](C[S@](=O)(=NC(C)=O)C(C)C)C(C)C)C2=O)ccc1C(=O)O] |

TABLE A-continued
| number | structure |
| --- | --- |
| 043 | 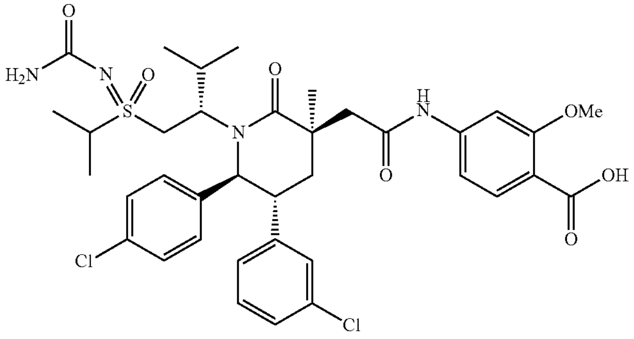 [SMILES: COc1cc(NC(=O)C[C@@]2(C)C[C@H](c3cccc(Cl)c3)[C@@H](c3ccc(Cl)cc3)N([C@H](CS(=O)(=NC(N)=O)C(C)C)C(C)C)C2=O)ccc1C(=O)O] |
| 045 | 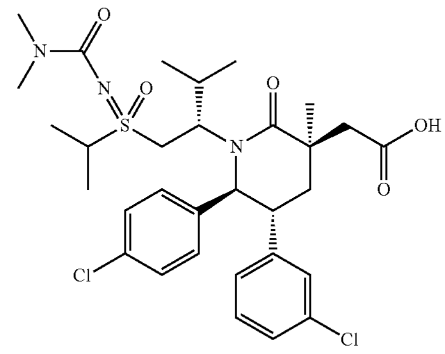 [SMILES: CC(C)[C@@H](CS(=O)(=NC(=O)N(C)C)C(C)C)N1C(=O)[C@@](C)(CC(=O)O)C[C@H](c2cccc(Cl)c2)[C@H]1c1ccc(Cl)cc1] |
| 046 | 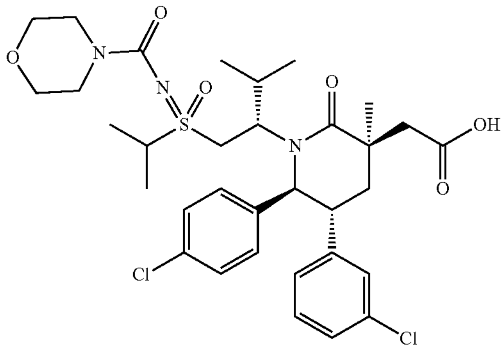 [SMILES: CC(C)[C@@H](CS(=O)(=NC(=O)N1CCOCC1)C(C)C)N1C(=O)[C@@](C)(CC(=O)O)C[C@H](c2cccc(Cl)c2)[C@H]1c1ccc(Cl)cc1] |
| 047 | 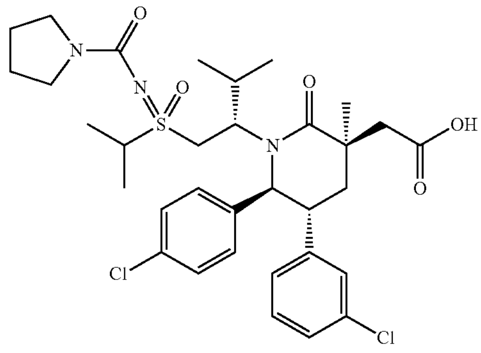 [SMILES: CC(C)[C@@H](CS(=O)(=NC(=O)N1CCCC1)C(C)C)N1C(=O)[C@@](C)(CC(=O)O)C[C@H](c2cccc(Cl)c2)[C@H]1c1ccc(Cl)cc1] |

TABLE A-continued
| number | structure |
|---|---|
| 048 | 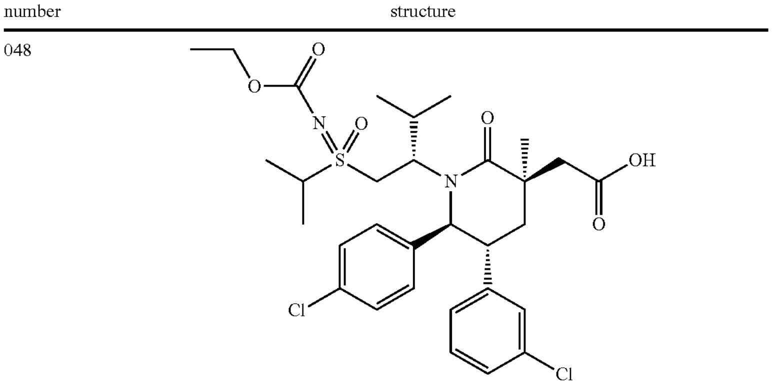 |
| 049 | 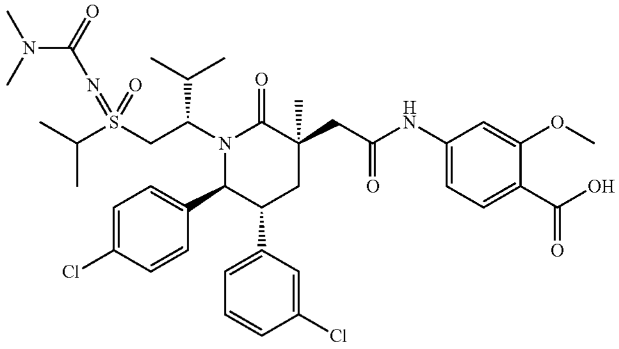 |
| 050 | 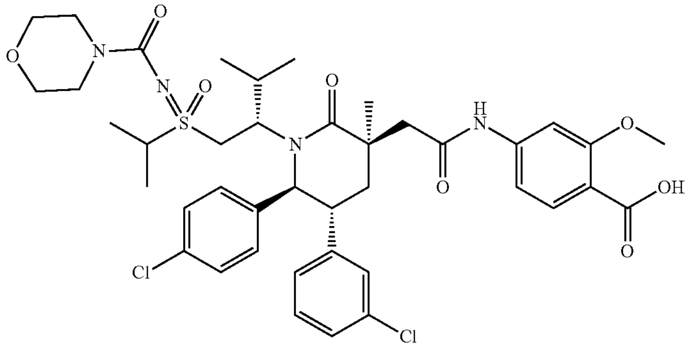 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCOCC3)C(C)C)C(C)C)C2=O)ccc1C(=O)O] |
| 051 | 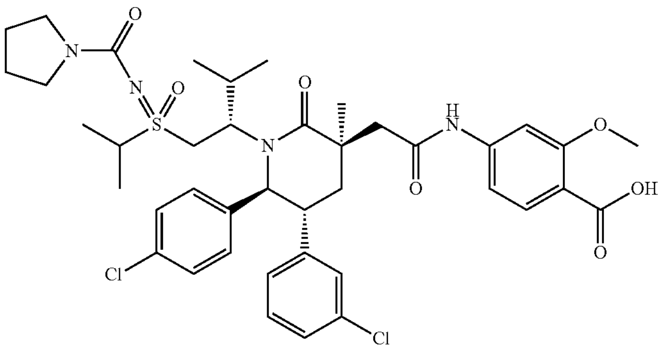 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCCC3)C(C)C)C(C)C)C2=O)ccc1C(=O)O] |

TABLE A-continued
| number | structure |
| --- | --- |
| 052 | 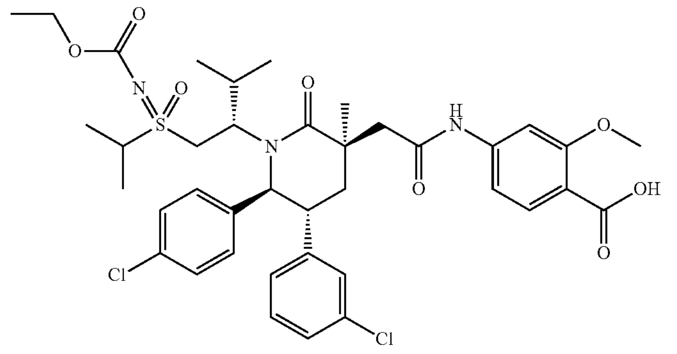 [SMILES: CCOC(=O)N=S(=O)(C[C@H](C(C)C)N1C(=O)[C@@](C)(CC(=O)Nc2ccc(C(=O)O)c(OC)c2)C[C@H](c2cccc(Cl)c2)[C@H]1c1ccc(Cl)cc1)C(C)C] |
| 053 | 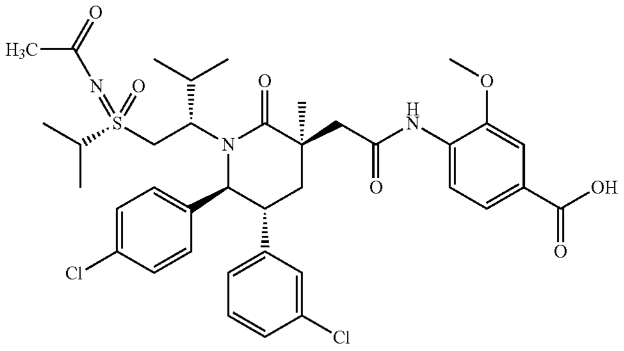 |
| 054 | 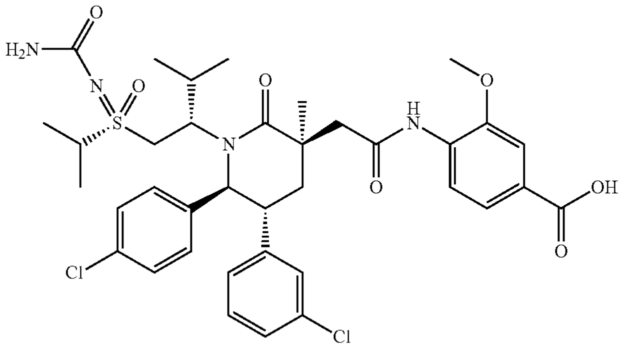 [SMILES: COc1cc(C(=O)O)ccc1NC(=O)C[C@@]1(C)C[C@H](c2cccc(Cl)c2)[C@@H](c2ccc(Cl)cc2)N([C@H](C[S@](=O)(=NC(C)=O)C(C)C)C(C)C)C1=O] |
In a preferred embodiment, the "isomer" refer to optically active isomers of which the chiral center is
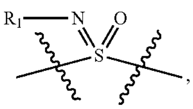
, or
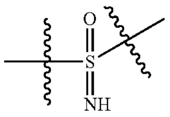
.
In the second aspect of the present invention, a method for preparing the compound of Formula I of the first aspect of the invention is provided, wherein the method comprises or is through step 1, step 2 or step 3:
Step (1):
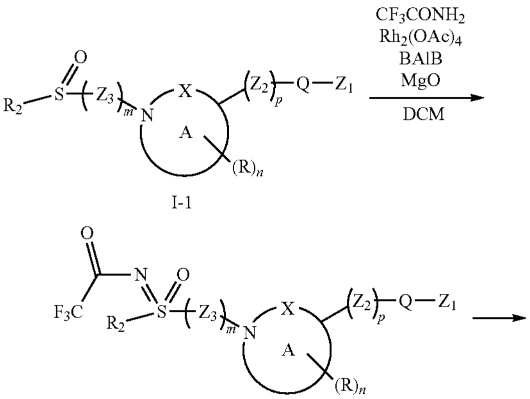
I-1
I-2

-continued

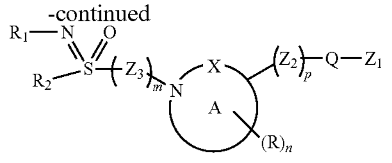

I-3

Step (2):

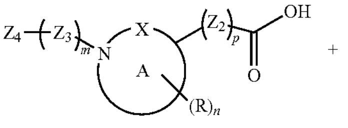

I-4

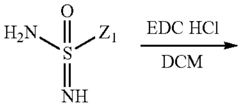

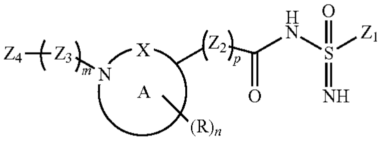

I-5

Step (3):

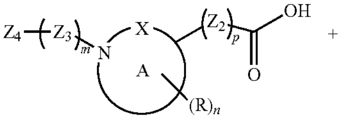

I-4

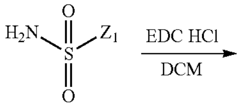

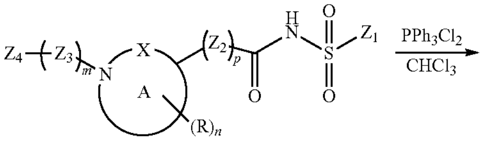

I-6

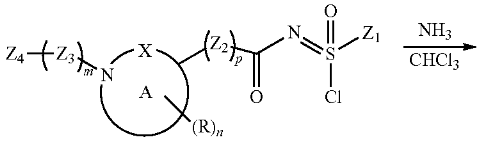

I-7

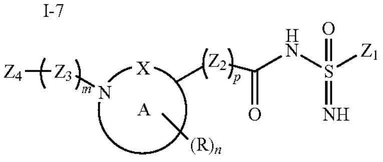

I-5

Wherein, each group is defined as described in the first aspect of the present invention.

In the third aspect of the present invention, a pharmaceutical composition is provided, which comprising (1) the compound, or stereoisomers or tautomers thereof, or pharmaceutically acceptable salts, hydrates or solvates thereof according to the first aspect of the present invention; (2) a pharmaceutically acceptable carrier.

In the fourth aspect of the present invention, a use of the compound, or stereoisomers or tautomers thereof, or pharmaceutically acceptable salts, hydrates or solvates thereof according to the first aspect of the present invention, or the pharmaceutical composition according to the third aspect of the present invention is provided, which is for preparing pharmaceutical compositions for preventing and/or treating diseases related to the activity or expression of MDM2.

In a preferred embodiment, the pharmaceutical composition also includes a second therapeutic agent, which is selected from the group consisting of small molecule anticancer drugs, antibodies, ADCs, cellular immune-therapeutic agents, or combinations thereof.

In a preferred embodiment, the pharmaceutical composition is used for the treatment of diseases selected from the group consisting of bladder cancer, breast cancer, colon cancer, rectal cancer, kidney cancer, liver cancer, lung cancer (small cell lung cancer and non-small cell lung cancer), esophageal cancer, gallbladder cancer, ovarian cancer, pancreatic cancer, gastric cancer, cervical cancer, thyroid cancer, prostate cancer and skin cancer (including squamous cell carcinoma); lymphatic lineage hematopoietic system tumors (including leukemia, acute lymphocytic leukemia, chronic myeloid leukemia, acute lymphoblastic leukemia, B-cell lymphoma, T-cell lymphoma, Hodgkin's lymphoma, non Hodgkin's lymphoma, hair cell lymphoma and Burkitt's lymphoma), bone marrow lineage hematopoietic system tumors (including acute and chronic myeloid leukemia, myelodysplastic syndrome and promyelocytic leukemia); mesenchymal neoplasms (including fibrosarcoma and rhabdomyosarcoma and other sarcomas, such as soft tissue sarcoma and osteosarcoma); central and peripheral nervous system tumors (including astrocytoma, neuroblastoma, glioma and neurosarcoma); other tumors (including melanoma, seminoma, teratoma, osteosarcoma, xerodermapigmentosum, keratoacanthoma, follicular thyroid cancer and Kaposi's sarcoma), endometrial cancer, head and neck cancer, glioblastoma, malignant ascites, hematopoietic system cancer, thyroid hyperplasia (especially grave's disease), cyst, asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis, Huntington's disease, inflammatory disease, hypoxia, ulcer, viral infection, bacterial infection and bacterial septicemia.

In a preferred embodiment, the diseases thereof are wild-type gene p53 tumors.

In a preferred embodiment, the diseases thereof are wild-type gene p53 tumors and CDKN2A mutant cancers.

In the fifth aspect of the present invention, an MDM2 inhibitor comprising the compound, or stereoisomers or tautomers thereof, or pharmaceutically acceptable salts, hydrates or solvates thereof according to the first aspect of the present invention is provided.

In the sixth aspect of the present invention, a method to inhibit MDM2 activity in vitro by contacting MDM2 protein with the compound, or stereoisomers or tautomers thereof, or pharmaceutically acceptable salts, hydrates or solvates thereof according to the first aspect of the present invention is provided.

In a preferred embodiment, the method thereof is non-therapeutic and non-diagnostic.

The seventh aspect of the present invention provides a method to treat tumor, which comprises: administrating to a subject in need thereof with the compound, or stereoisomers or tautomers thereof, or pharmaceutically acceptable salts, hydrates or solvates thereof according to the first aspect of the present invention, or pharmaceutical composition thereof according to the third aspect of the present invention.

In a preferred embodiment, the method thereof also includes companion diagnosing the subject thereof to identify whether or not the subject is suitable for administration of the compound or pharmaceutical composition of the invention.

It should be understood that, in the present invention, each of the technical features specifically described above and below (such as those in the examples) can be combined with each other, thereby constituting new or preferred technical solutions which need not be specified again herein.

EMBODIMENTS FOR CARRYING OUT THE INVENTION

The inventor discovered an MDM2 inhibitor with excellent inhibitory effect after long-term and in-depth research. The inventor completed the present invention on this basis.

Terms

As used herein, the term "alkyl" includes straight or branched alkyl groups. For example, $C_1$-$C_8$ alkyl refers to straight or branched alkyls having 1-8 carbon atoms, such as methyl, ethyl, propyl, isopropyl, butyl, isobutyl, tert-butyl, and the like.

As used herein, the term "alkenyl" includes straight or branched alkenyl groups. For example, $C_2$-$C_6$ alkenyl refers to straight or branched alkenyl groups having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "$C_2$-$C_6$ alkynyl" refers to a straight or branched alkynyl having 2-6 carbon atoms, such as ethynyl, propynyl, butynyl, and the like.

As used herein, the term "$C_3$-$C_{10}$ cycloalkyl" refers to cycloalkyl group having 3 to 10 carbon atoms. It may be a monocyclic ring, such as cyclopropyl, cyclobutyl, cyclopentyl, cyclohexyl, and the like. It may also be of bicyclic form, such as bridged or spiro ring form.

As used herein, the term "$C_1$-$C_8$ alkylamino" refers to an amine group substituted by $C_1$-$C_8$ alkyl, which may be monosubstituted or di-substituted; for example, methylamino, ethylamino, propylamine, isopropylamino, butylamino, isobutylamino, tert-butylamino, dimethylamino, diethylamino, dipropylamino, diisopropylamino, dibutylamino, diisobutylamino, di(tert-butyl)amine, and the like.

As used herein, the term "$C_1$-$C_8$ alkoxy" refers to straight or branched alkoxy groups having 1-8 carbon atoms; for example, methoxy, ethoxy, propoxy, isopropoxy, butoxy, isobutoxy, tert-butoxy, and the like.

As used herein, the term "3-10 membered heterocycloalkyl having 1-3 heteroatoms selected from N, S and O" refers to a saturated or partially saturated cyclic group comprising 3-10 atoms, in which 1-3 atoms are selected from N, S and O heteroatom. It may be a monocyclic ring or bicyclic form, such as bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, the term "$C_6$-$C_{10}$ aryl" refers to an aryl group having 6 to 10 carbon atoms, such as phenyl, naphthyl, and the like.

As used herein, the term "5-10 membered heterocycloalkyl having 1-3 heteroatoms selected from N, S and O" refers to a cyclic group aromatic group comprising 5-10 atoms, in which 1-3 atoms are selected from heteroatoms N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified as "substituted or unsubstituted", all the groups described in the present invention may be substituted with a substituent selected from the group consisting of halogen, nitrile, nitro, hydroxyl, amino, $C_1$-$C_6$ alkyl-amine, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_2$-$C_6$ haloalkenyl, $C_2$-$C_6$ haloalkynyl, $C_1$-$C_6$ haloalkoxy, allyl, benzyl, $C_6$-$C_{12}$ aryl, $C_1$-$C_6$ alkoxy-$C_1$-$C_6$ alkyl, $C_1$-$C_6$ alkoxy-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, $C_1$, Br, and I. More preferably, the halogen or halogen atom is selected from F, Cl and Br. "Halogenated" means substitution by an atom selected from the group consisting of F, Cl, Br, and I.

Unless otherwise specified, the structural formula described herein is intended to include all isomeric forms (such as enantiomeric, diastereomeric, and geometric isomers (or conformational isomers)): for example, R, S configuration having an asymmetrical center, (Z), (E) isomers of double bonds, etc. Therefore, the single stereochemical isomer or enantiomer, diastereomer or geometric isomer (or conformer) of the compound of the invention, or mixtures thereof all fall within the scope of the invention.

As used herein, the term "tautomer" means that structural isomers having different energies can exceed the low energy barrier and thereby transform between each other. For example, proton tautomers (proton shift) include interconversion by proton transfer, such as 1H-carbazole and 2H-carbazole. Valence tautomers include interconversion through some bonding electron recombination.

As used herein, the term "solvate" refers to a complex of specific ratio formed by a compound of the invention coordinating to a solvent molecule.

As used herein, the term "hydrate" refers to a complex formed by the coordination of a compound of the invention with water.

Active Ingredients

As used herein, "compound of the invention" refers to the compound according to formula I and various crystal forms of the compound of formula I, or the pharmaceutically acceptable salts, hydrate or solvates thereof.

I

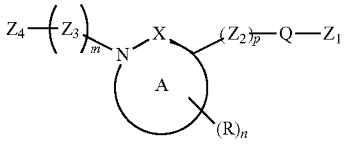

wherein,

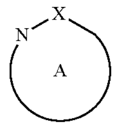

is selected from the group consisting of 5-10 membered heterocyclic with 1-3 N and 0-2 heteroatoms selected from S and O;

X is independently C═0 or S═$(O)_2$;

n is 1, 2, 3 or 4;

each R is selected independently from the group consisting of H, cyano, halogen, substituted or unsubstituted $C_1$-$C_6$ alkyl, substituted or unsubstituted $C_1$-$C_6$ alkoxy, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O;

$Z_1$ is selected from the group consisting of H, substituted or unsubstituted $C_1$-$C_6$ alkyl, substituted or unsubstituted $C_1$-$C_6$ alkoxy, substituted or unsubstituted $C_3$-$C_8$ cycloalkyl (including single, fused or bridged ring form), substituted or unsubstituted $C_6$-$C_{10}$ aryl;

Q is selected from the group consisting of

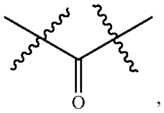
,
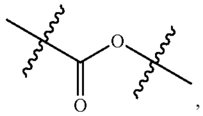
,
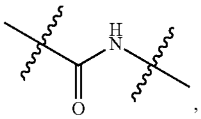
,
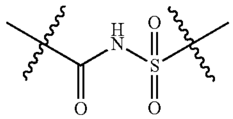
or
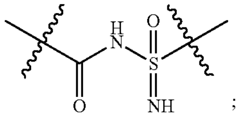
;

m and p are selected independently from the group consisting of 1, 2, 3 or 4;

Each $Z_2$ and $Z_3$ is selected independently from the group consisting of none, substituted or unsubstituted $C_1$-$C_7$ alkylidene $NR_1$, O, S, C═O, S═$(O)_2$;

$Z_4$ is selected from

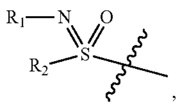
,
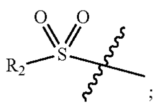
;

wherein $R_1$ is selected from the group consisting of H, substituted or unsubstituted $C_1$-$C_6$ alkyl, substituted or unsubstituted $C_6$-$C_{10}$ aryl, CN, —C(═O)—NRdRe, —C(═O)-substituted or unsubstituted $C_1$-$C_6$ alkoxy, —C(═O)-substituted or unsubstituted $C_1$-$C_6$ alkyl, —C(═O)-substituted or unsubstituted $C_3$-$C_{10}$ cycloalkyl, —C(═O)— substituted or unsubstituted $C_2$-$C_6$ alkenyl, —C(═O)-substituted or unsubstituted $C_2$-$C_6$ alkynyl;

Rd and Re are independently selected from the group consisting of H, substituted or unsubstituted $C_1$-$C_6$ alkyl, substituted or unsubstituted $C_3$-$C_{10}$ cycloalkyl, substituted or unsubstituted $C_6$-$C_{10}$ aryl; the Rd and Re herein form a 4-8 membered heterocyclic with adjacent N, while the heterocyclic contains 1-2 N and 0-2 S or O.

$R_2$ is selected from the group consisting of substituted or unsubstituted $C_1$-$C_6$ alkyl, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O.

Unless otherwise specified, "substituted" refers to being substituted by one or more (for example, 2, 3, 4, etc.) substituents selected from the group consisting of halogen, $C_1$-$C_6$ alkyl, halogenated $C_1$-$C_6$ alkyl, $C_1$-$C_6$ alkoxy, halogenated $C_1$-$C_6$ alkoxy, $C_3$-$C_8$ cycloalkyl, halogenated $C_3$-$C_8$ cycloalkyl, oxo, —CN, hydroxy, —$NH_2$, carboxy, unsubstituted or substituted group selected from the group consisting of $C_6$-$C_{10}$ aryl, halogenated $C_6$-$C_{10}$ aryl, 5-10 membered heteroaryl with 1-3 heteroatoms selected from N, S and O; halogenated 5-10 membered heteroaryl with 1-3 heteroatoms selected from N, S and O; and the substituted is substituted by substituents selected from the group consisting of halogen, $C_1$-$C_6$ alkoxy;

with the proviso that, when $Z_4$ is

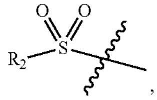
, then Q is

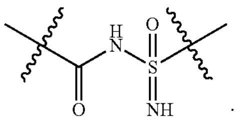 [SMILES: *C(=O)NS(*)(=N)=O]
.

As used herein, "pharmaceutically acceptable salts" refers to the salt formed by the compound of the invention and acid or base, which is suitable for drug use. Pharmaceutically acceptable salts include inorganic and organic salts. A preferred type of salt is the salt formed by the compound of the invention and acid. The acids suitable for forming salt include but are not limited to: inorganic acids such as hydrochloric acid, hydrobromic acid, hydrofluoric acid, sulfuric acid, nitric acid, phosphoric acid; organic acids such as formic acid, acetic acid, propionic acid, oxalic acid, malonic acid, succinic acid, fumaric acid, maleic acid, lactate, malic acid, tartaric acid, citric acid, picric acid, mesulfonic acid, benzosulfonic acid, benzenesulfonic acid, acidic amino acids such as aspartic acid, glutamic acid. The cations suitable for forming salt include: cations of alkali metal and alkaline earth metal, such as sodium ion, lithium ion, potassium ion, calcium ion, magnesium ion, etc., as well as nontoxic ammonium, quaternary ammonium and amine cations, including (but not limited to) ammonium, tetramethylammonium, tetraethyl ammonium, methylamine, dimethylamine, trimethylamine, triethylamine, ethylamine, etc..

In a preferred embodiment,

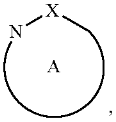
, m, n, p, $Z_1$, $Z_2$, $Z_3$, $Z_4$, Q, R are independently selected from the groups or values presented in both table A and table B.

A preferred type of compounds thereof is as presented in table A and table B.

Pharmaceutical Composition and Administration Mode

Since the compound herein has excellent MDM2 inhibitory activity, the compound of the present invention and various crystal forms thereof, pharmaceutically acceptable inorganic or organic salts, hydrates or solvates thereof, and pharmaceutical composition containing the compound according to the present invention as main active ingredient can be used to treat (stabilize, reduce or heal) cancers. Cancers that can be treated with compound herein include (but is not limited to): bladder cancer, breast cancer, colon cancer, rectal cancer, kidney cancer, liver cancer, lung cancer (small cell lung cancer and non-small cell lung cancer), esophageal cancer, gallbladder cancer, ovarian cancer, pancreatic cancer, gastric cancer, cervical cancer, thyroid cancer, prostate cancer and skin cancer (including squamous cell carcinoma); lymphatic lineage hematopoietic system tumors (including leukemia, acute lymphocytic leukemia, chronic myeloid leukemia, acute lymphoblastic leukemia, B-cell lymphoma, T-cell lymphoma, Hodgkin's lymphoma, non Hodgkin's lymphoma, hair cell lymphoma and Burkitt's lymphoma), bone marrow lineage hematopoietic system tumors (including acute and chronic myeloid leukemia, myelodysplastic syndrome and promyelocytic leukemia); mesenchymal neoplasms (including fibrosarcoma and rhabdomyosarcoma and other sarcomas, such as soft tissue sarcoma and osteosarcoma); central and peripheral nervous system tumors (including astrocytoma, neuroblastoma, glioma and neurosarcoma); other tumors (including melanoma, seminoma, teratoma, osteosarcoma, xerodermapigmentosum, keratoacanthoma, follicular thyroid cancer and Kaposi's sarcoma). Other cancer can be treated by the compound of the present invention includes endometrial cancer, head and neck cancer, glioblastoma, malignant ascites, hematopoietic system cancer Cancers that can be treated with compound herein include soft tissue sarcoma, bone cancer (such as osteosarcoma), breast cancer, bladder cancer, Li-Fraumeni syndrome, brain tumor, rhabdomyosarcoma, adrenocortical cancer, colorectal cancer, non-small cell lung cancer, and acute myeloid leukemia (AML).

The pharmaceutical composition of the invention comprises the compound of the present invention in a safe and effective dosage range and a pharmaceutically acceptable excipient or carrier. The term "safe and effective dosage" means that the amount of compound is sufficient to significantly improve the condition without causing serious side effects. Generally, the pharmaceutical composition contains 1-2000 mg compound of the invention per dose, preferably, 10-200 mg compound of the invention per dose. Preferably, the "one dose" is one capsule or one tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical composition of the present invention, and the representative administration mode includes (but is not limited to): oral, parenteral (intravenous, intramuscular or subcutaneous) administration.

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The compounds of the present invention can be administrated alone, or in combination with any other pharmaceutically acceptable compounds (such as chemical anticancer drugs).

In the case of co-administration, the pharmaceutical composition can also include one or more (2, 3, 4, or more) other pharmaceutically acceptable compounds (such as chemical anticancer drugs). One or more (2, 3, 4, or more) other pharmaceutically acceptable compounds (e.g., chemical anticancer drugs) may be used simultaneously, separately or sequentially with the compound of the present invention so as to prevent and/or treat cancer or cancer related diseases.

When the pharmaceutical composition is used, a safe and effective amount of compound of the present invention is administered to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The compounds of the present invention can be administrated alone, or in combination with any other pharmaceutically acceptable compounds (such as chemical anticancer agents).

In the case of co-administration, the pharmaceutical composition can also include one or more (2, 3, 4, or more) other pharmaceutically acceptable compounds (such as chemical anticancer agents). One or more (2, 3, 4, or more) other pharmaceutically acceptable compounds (e.g., chemical anticancer drugs) may be used simultaneously, separately or sequentially with the compound of the present invention so as to prevent and/or treat cancer or cancer related diseases.

When the pharmaceutical composition is used, a safe and effective amount of compound of the present invention is administered to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The Main Advantages of the Present Invention Include:

(1) The compounds of the present invention are novel in structure and have an excellent MDM2 inhibitory effect. In the present invention, the existing sulfone compounds were transformed into thioimines in order to reduce the binding rate of plasma protein, increase the amount of free drugs and make it easy to transport to organs and tissues as well as keeping the inhibitory to MDM2 activity or expression amount.

(2) The compounds of the invention are low toxicity to normal cells.

(3) The compound of the invention has good druggability. Compared with the existing compounds, the compound of the invention has better solubility and has shown good in vivo bioavailability. In addition, compared with the existing compounds, the compound of the invention can be prepared into pharmaceutically acceptable salt easily, which is benefit for further preparation.

(4) The compound and pharmaceutical composition with the compound according to the present invention can be used as main active ingredient to treat cancer related diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Compounds in each embodiment are prepared by the following way:

Example 1

Synthesis of 2-((3R,5R,6S)-5-(3-chlorophenyl)-6-(4-chlorophenyl)-3-methyl-1-((2S)-3-methyl-1-(propyl-2-sulfonamido)butyl-2-)-2-oxo-piperidine-3-yl)aceticacid

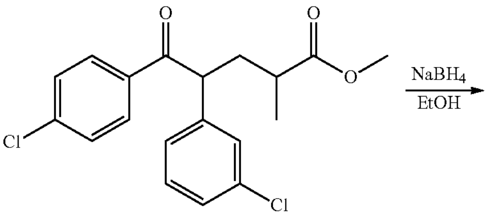

1

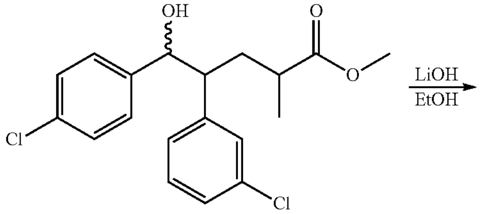

2

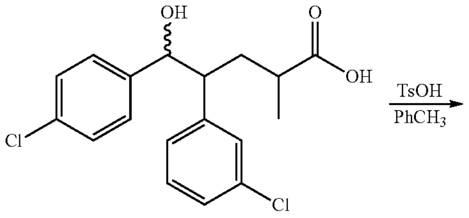

3

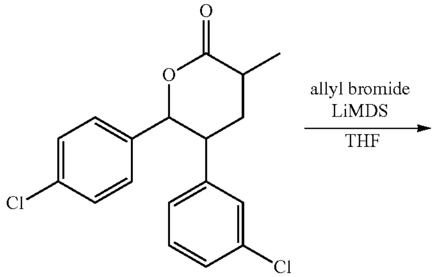

4

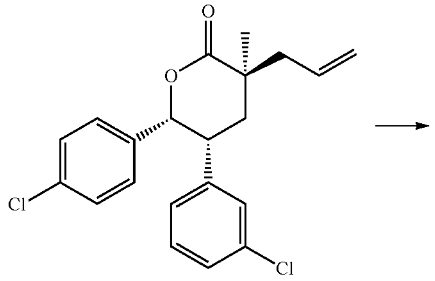

5

-continued
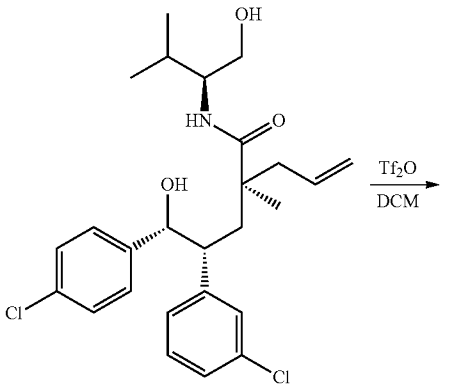
6
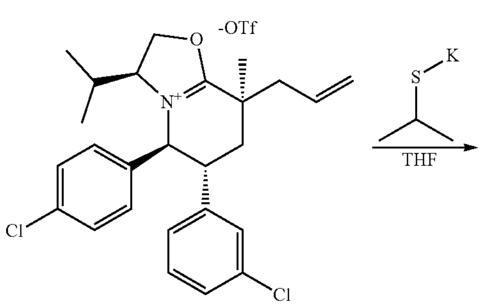
7
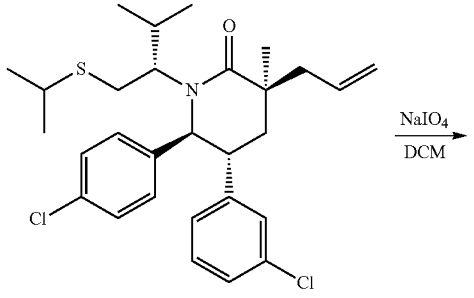
8
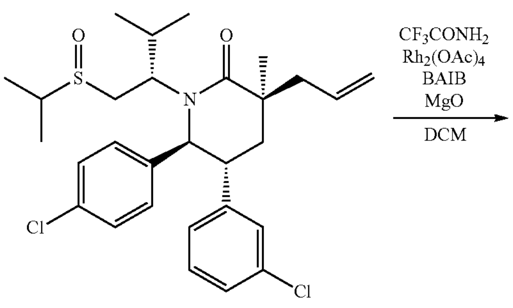
9
-continued
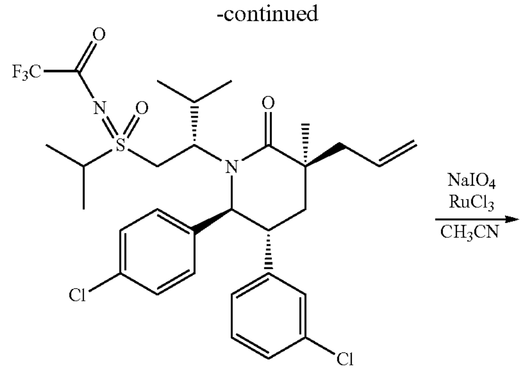
10
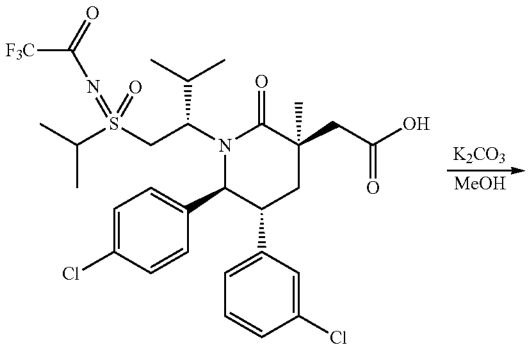
11
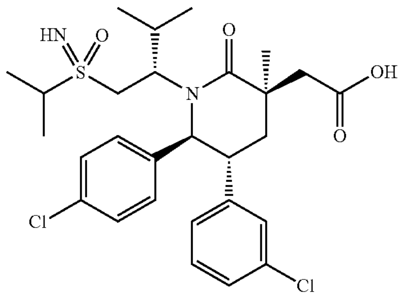
001 & 002
Step I: Methyl4-(3-chlorophenyl)-5-(4-chlorophenyl)-5-hydroxy-2-methylvalerate
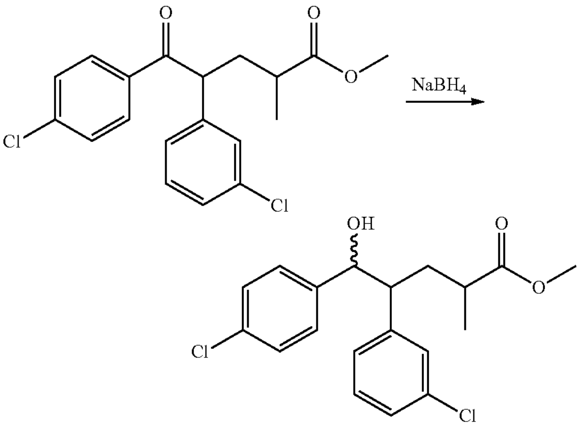

Methyl 4-(3-chlorophenyl)-5-(4-chlorophenyl)-2-methyl-5-oxovanoate (36.5 g) was dissolved in ethanol (300 ml) and cooled to 0-5° C. $NaBH_4$(2.85 g) was added to the mixture in batches and then reacted at 0-10° C. for 2 hours. TLC showed that the reaction was completed. Acetic acid (~8 ml) was added dropwise until no hydrogen released. The resulting solution was concentrated under vacuum, and ethyl acetate(300 ml) was added to the residue and washed with water and saturated sodium bicarbonate solution successively, and dried over anhydrous magnesium sulfate. Methyl 4-(3-chlorophenyl)-5-(4-chlorophenyl)-5-hydroxy-2-methyl valerate (37g) was provided by concentration.

Step 2: 4-(3-chlorophenyl)-5-(4-chlorophenyl)-5-hydroxy-2-methylvaleric acid

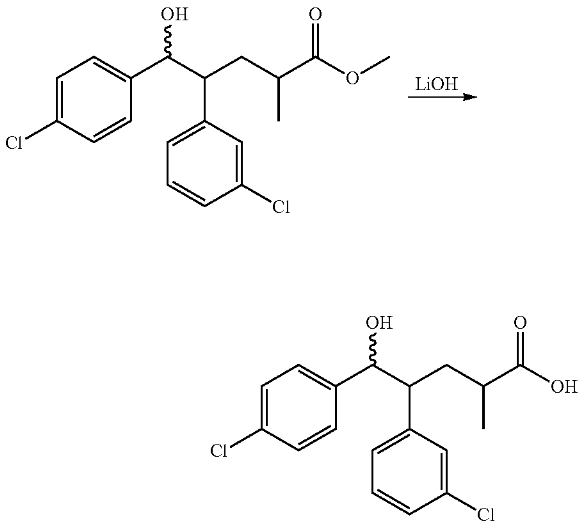

To a solution of methyl 4-(3-chlorophenyl)-5-(4-chlorophenyl)-5-hydroxy-2-methylvalerate (37 g) in ethanol (300 ml) was added 100 ml aqueous solution of $LiOH.H_2O$ (8.4 g). The mixture was reacted at 20° C. for 18 hours. TLC showed that the reaction was completed. 4N HCl was added dropwise to adjust the pH<1. The mixture was concentrated under vacuum. The residue was extracted twice with toluene (250 mlx2) at 50° C. and was washed with water to afford 4-(3-chlorophenyl)-5-(4-chlorophenyl)-5-hydroxy-2-methylvaleric acid in toluene which was used directly in the next step.

Step 3: 5-(3-chlorophenyl)-6-(4-chlorophenyl)-3-methyltetrahydro-2H-pyran-2-one

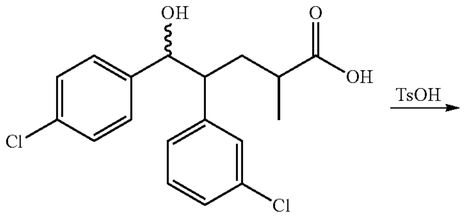

-continued

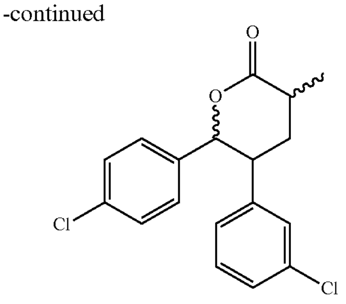

To toluene solution of 4-(3-chlorophenyl)-5-(4-chlorophenyl)-5-hydroxy-2-methylvaleric acid was added $TsOH.H_2O$ (1.0 g). The mixture was heated to reflux for 2 hours. TLC showed that the reaction was completed. The mixture was cooled, washed with saturated sodium bicarbonate solution and dried over anhydrous magnesium sulfate. Tolune solution was concentrated to afford 37.7 g crude product, and purified with column chromatography to afford 5-(3-chlorophenyl)-6-(4-chlorophenyl)-3-methyltetrahydro-2H-pyran-2-one.

Step 4: (+) (3S,5R,6R)-3-allyl-5-(3-chlorophenyl)-6-(4-chlorophenyl)-3-methyltetrahydro-2 h-pyran-2-one

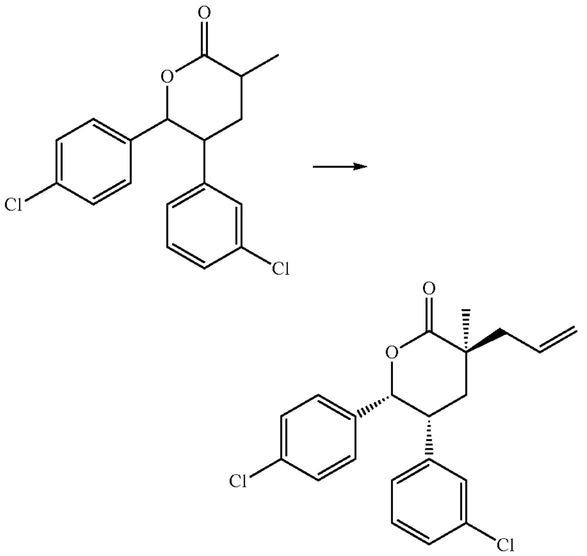

5-(3-chlorophenyl)-6-(4-chlorophenyl)-3-methyltetrahydro-2 h-pyran-2-one (6.7 g) and bromopropene (7.26 g) were added to THF and cooled to −50° C. LiHMDS (26 ml, 1M in THF) was added dropwise, then the mixture was warmed up to 0° C. and stirred for 1 hour. TLC showed the reaction was completed. Saturated ammonium chloride solution was added to the mixture, and extracted with ethyl acetate. The residue was separated with column chromatography to yield 6.0 g product. Because isomers were hard to purify with column chromatography, the 6.0 g product was added into 50 ml N-heptane/toluene (10:1) and heated and refluxed to dissolve. After slowly cooled to room temperature, the mixture was precipitated to provide 2.8 g solid (±)(3S,5R,6R)-3-allyl-5-(3-chlorophenyl)-6-(4-chlorophenyl)-3-methyltetrahydro-2H-pyran-2-one.

$^1$HNMR($CDCl_3$, 400 MHz): 7.22-7.11 (m, 4H), 6.873 (d, 1H, J=1.9 Hz), 6.745 (d, 1H, J=7.8 Hz), 6.58-6.54 (m, 2H), 5.804 (m, 1H), 5.677 (d, 1H, J=5.1 Hz), 5.157 (d, 1H, J=10.2 Hz), 5.125 (dd, 1H, J=1.6, 15.3 Hz), 3.787 (dt, 1H, J=4.5, 12.2 Hz), 2.598 (dd, 1H, J=7.9, 14.1 Hz), 2.488 (dd, 1H, J=7.1, 13.7 Hz), 1.954 (t, 1H, J=14.0 Hz), 1.897 (dd, 1H, J=4.5, 14.0 Hz), 1.389 (s, 3H).

Step 5: 2-((2R,3R)-2-(3-chlorophenyl)-3-(4-chlorophenyl)-3-hydroxypropyl)-N-((S)-1-hydroxy-3-methylbutyl-2)-2-methylpenten-4-amide

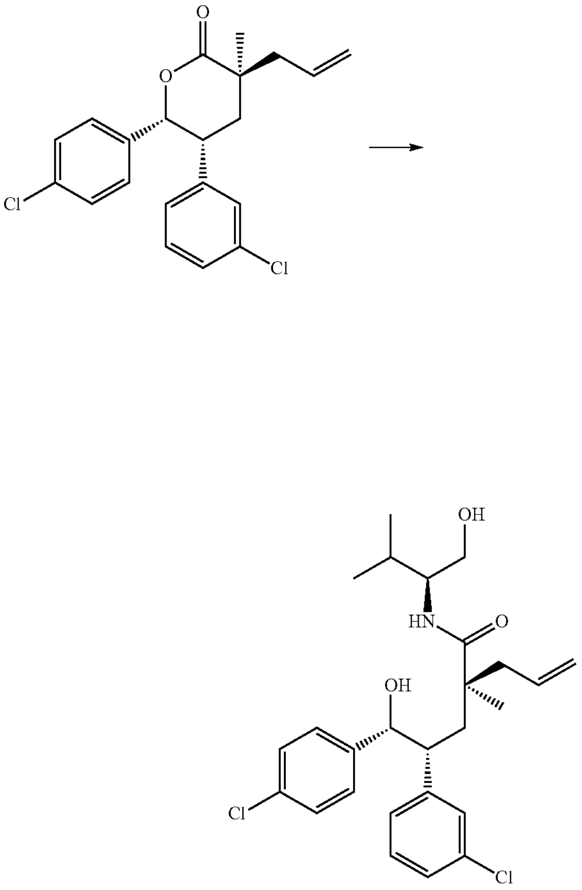

To a solution of (+)(3S,5R,6R)-3-allyl-5-(3-chlorophenyl)-6-(4-chlorophenyl)-3-methyltetrahydro-2H-pyran-2-one in tolune (1 ml) was added L-Valinol (0.825 g). The mixture was heated to 100° C. and reacted for 5 hours. TLC showed that the reaction was completed. The mixture was cooled and ethyl acetate was added. The mixture was washed with 1 N HCl and saturated sodium bicarbonate solution and dried over anhydrous magnesium sulfate. The solution was concentrated to afford 1.48 g 2-((2R,3R)-2-(3-chlorophenyl)-3-(4-chlorophenyl)-3-hydroxypropyl)-N-((S)-1-hydroxy-3-methylbutyl-2)-2-methylpenten-4-amide.

Step 6: Trifluoromethanesulfonic acid (3S,5S,6R,8S)-8-allyl-6-(3-chlorophenyl)-5-(4-chlorophenyl)-3-isopropyl-8-methyl-2,3,5,6,7,8-hexahydroxazolo [3,2-a]-4-pyridinium salt

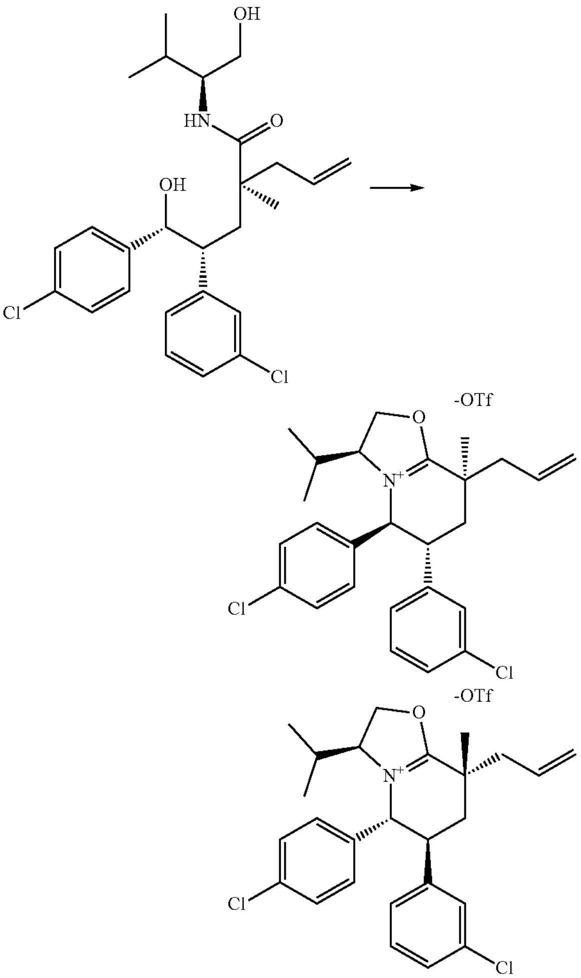

To a solution of 2-((2R,3R)-2-(3-chlorophenyl)-3-(4-chlorophenyl)-3-hydroxypropyl)-N-((S)-1-hydroxy-3-methylbutyl-2)-2-methylpenten-4-amide (63.6 g) in DCM (640 ml) was added 2,6-lutidine (57 g). After cooled to −78° C., $Tf_2O$ (97.6 g) was added dropwise into the mixture. The mixture was warmed to room temperature and reacted overnight. The resulting solution was washed with 0.5M TfOH (200 ml) and then extracted with ethyl acetate (500 ml×2). The organic phase was concentrated and dissolved in DCM (400 mL), purified with column chromatography.

The parameters were:
silica gel: 120 g;
each sample; 10 g;
mobile phase: A: heptane, B: acetone;

| Time(min) | Ratio of mobile phases |
|---|---|
| 0-5 | 25% |
| 5-15 | 25%-35% |
| 15-30 | 35% |
| 30-35 | 25% |

The isomer of low polarity was trifluoromethanesulfonic acid (3S,5S,6R,8S)-8-allyl-6-(3-chlorophenyl)-5-(4-chlorophenyl)-3-isopropyl-8-methyl-2,3,5,6,7,8-hexahydroxazolo [3,2-a]-4-pyridinium salt (27.4 g, 34.8%).

$^1$HNMR (d6-DMSO, 400 MHz): 8.15-7.10 (m, 8H), 5.812 (m, 1H), 5.346 (dd, 1H, J=1.2, 16.8 Hz), 5.238 (dd, 1H, J=1.5, 10.1 Hz), 5.173 (d, 1H, J=11.3 Hz), 5.003 (dd, 1H, J=5.5, 10.2 Hz), 4.870 (t, 1H, J=10.2 Hz), 4.323 (m, 1H), 4.057 (ddd, 1H, 3.1, 13.7, 10.6 Hz), 2.812 (dd, 1H, J=7.1, 13.7 Hz), 2.717 (dd, 1H, J=7.4, 13.7 Hz), 2.316 (t, 1H, 13.7 Hz), 1.993 (dd, 1H, J=13.7, 3.5 Hz), 1.303 (s, 3H), 0.579 (d, 3H, J=6.7 Hz), 0.524 (d, 3H, J=7.0 Hz), 0.428 (m, 1H).

The isomer of high polarity was trifluoromethanesulfonic acid (3S,5R,6S,8R)-8-allyl-6-(3-chlorophenyl)-5-(4-chlorophenyl)-3-isopropyl-8-methyl-2,3,5,6,7,8-hexahydroxazolo [3,2-a]-4-pyridinium salt (22.8 g, 28.9%).

$^1$HNMR (d6-DMSO, 400 MHz): 7.50-7.05 (m, 8H), 5.902 (m, 1H), 5.290 (dd, 1H, J=1.6, 17.2 Hz), 5.230 (dd, 1H, J=2.4, 10.2 Hz), 5.140 (d, 1H, J=10.2 Hz), 5.084 (dd, 1H, J=3.9, 10.2 Hz), 4.927 (t, 1H, J=10.2 Hz), 3.878 (m, 1H), 3.423 (m, 1H), 2.733 (dd, 1H, J=8.3, 14.1 Hz), 2.657 (dd, 1H, J=6.7, 13.7 Hz), 2.334 (t, 1H, 13.7 Hz), 2.005 (dd, 1H, J=13.7, 2.7 Hz), 1.334 (s, 3H), 0.884 (d, 3H, J=6.6 Hz), 0.662 (d, 3H, J=6.6 Hz).

Step 7: (3S,5R,6S)-3-allyl-5-(3-chlorophenyl)-6-(4-chlorophenyl)-1-(S)-1-(isopropylmercaptol)-3-methyl-butyl-2)-3-methylpiperidine-2-one

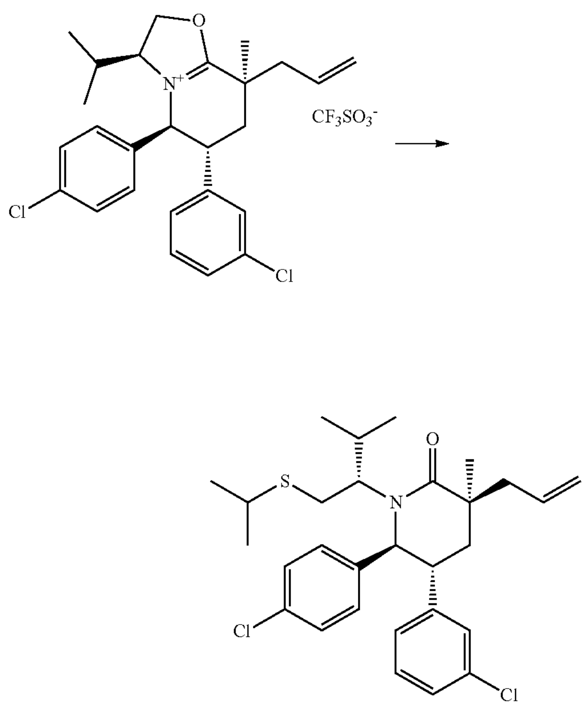

Isopropyl mercaptan(10.4 g) was added into potassium tert-butyl alcohol (82.2 ml 1M THF) under $N_2$, and cooled to keep the temperature under 30° C. The mixture was then stirred for 10 min. Trifluoromethanesulfonic acid (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]-4-pyridinium salt (17.8 g) in DMF (80 ml) was added and warmed to 50° C. to react for 3 hours. TLC showed that the reaction was completed. The mixture was poured into water (600 ml) and then extracted with ethyl acetate (200 ml×3), and washed with water. The mixture was concentrated and purified with column chromatography to yield 13.5 g oily (3S,5R,6S)-3-allyl-5-(3-chlorophenyl)-6-(4-chlorophenyl)-1-((S)-1-(isopropylmercapto)-3-methylbutyl-2)-3-methylpiperidine-2-one.

Step 8: (3S,5R,6S)-3-allyl-5-(3-chlorophenyl)-6-(4-chlorophenyl)-1-((S)-1-(isopropylsulfoxide)-3-methylbutyl-2)-3-methylpiperidine-2-one

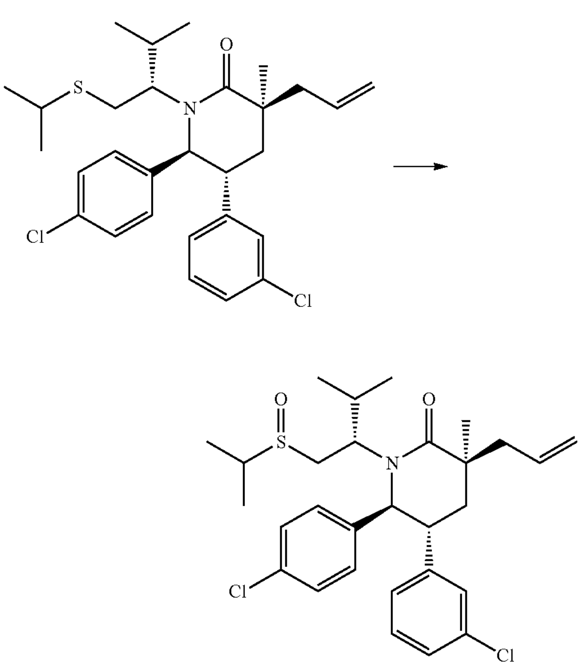

To a solution of (3S,5R,6S)-3-allyl-5-(3-chlorophenyl)-6-(4-chlorophenyl)-1-((S)-1-(isopropylmercapto)-3-methylbutyl-2)-3-methylpiperidine-2-one (2.03 g) in MeOH (25 ml) was added 30% $H_2O_2$ (0.6 ml). The mixture was reacted at 20-25° C. for 2 days. Sodium thiosulfate solution was added to quench the reaction. The mixture was then extracted with ethyl acetate and dried over anhydrous magnesium sulfate. The organic phase was concentrated after filtration and was purified with column chromatography to yield 1.99 g (3S,5R,6S)-3-allyl-5-(3-chlorophenyl)-6-(4-chlorophenyl)-1-((S)-1-(isopropylsulfoxide)-3-methylbutyl-2)-3-methylpiperidine-2-one as the mixture of two isomers, yield 95%.

$^1$HNMR($CDCl_3$, 400 MHz): 7.27-7.00 (m, 7H), 6.978 (d, 1H, J=6.8 Hz), 5.898 (m, 1H), 5.260 (d, 1H, J=16.8 Hz), 5.180 (dd, 1H, J=1.2, 10.0 Hz), 4.860 (d, 1H, J=8.4 Hz), 3.620 (t, 1H, J=10.5 Hz), 3.541 (ddd, 1H, J=2.3, 11.0, 13.3 Hz), 3.017 (m, 2H), 2.860 (dd, 1H, J=2.7, 12.9 Hz), 2.741 (dd, 1H, J=8.2, 14.1 Hz), 2.716 (dd, 1H, J=2.8, 13.3 Hz), 2.585 (dd, 1H, J=6.7, 13.7 Hz), 2.188 (m, 1H), 2.101 (t, 1H, J=13.7 Hz), 1.922 (dd, 1H, J=2.8, 13.7 Hz), 1.343 (d, 3H, J=7.0 Hz), 1.277 (d, 3H, J=7.0 Hz), 1.199 (s, 3H), 0.863 (t, 1H, J=6.6 Hz), 0.675 (d, 3H, J=6.7 Hz), 0.481 (d, 3H, J=7.0 Hz).

Step 9: 2,2,2-trifluoroacetic N-(((S)-2-((3S,5R,6S)-3-allyl-5-(3-chlorophenyl)-6-(4-chlorophenyl)-3-methyl-2-oxo-piperidin-1-yl)-3-methylbutyl)(isopropyl)(oxo)-16-sulfonamidine)

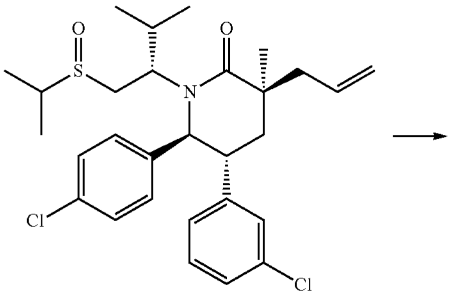

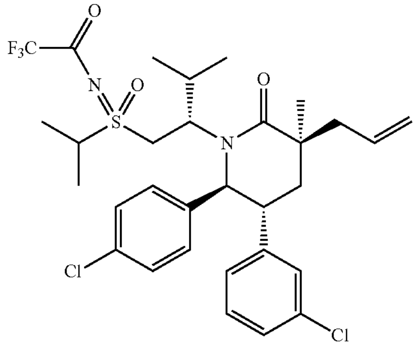

To a solution of (3S,5R,6S)-3-allyl-5-(3-chlorophenyl)-6-(4-chlorophenyl)-1-((S)-1-(isopropylsulfoxide)-3-methylbutyl-2)-3-methylpiperidine-2-one (336 mg) and trifluoroacetamide (142.4 mg) in DCM (4 ml) was added MgO (126.5 mg), $Rh_2(OAc)_4$ (6.9 mg) and $PhI(OAc)_2$ (303.7 mg). The mixture was then stirred overnight at room temperature, then filtrated, and the solid was washed with DCM. The eluent was concentrated and purified by column chromatography with N-heptane/ethyl acetate (2:1) as the eluent to afford 58 mg 2,2,2-trifluoroacetic N-(((S)-2-((3S,5R,6S)-3-allyl-5-(3-chlorophenyl)-6-(4-chlorophenyl)-3-methyl-2-oxo-piperidin-1-yl)-3-methylbutyl)(isopropyl)(oxy)-16-sulfonamidine) as the mixture of two isomers, yield 14%.

$^1$HNMR($CDCl_3$, 400 MHz): 7.3-7.1 (m, 6H), 6.932 (s, 1H), 6.860 (t, 1H, J=3.2 Hz), 5.904 (m, 1H), 5.239 (m, 2H), 4.959 (d, 1H, J=10.8 Hz), 4.450 (dd, 1H, J=7.6, 15.2 Hz), 4.135 (m, 1H), 3.368 (m, 2H), 3.186 (ddd, 1H, J=1.6, 7.6, 9.2 Hz), 2.658 (m, 2H), 2.390 (m, 1H), 2.229 (t, 1H, J=13.6 Hz), 1.898 (dd, 1H, J=3.2, 14.0 Hz), 1.522 (d, 3H, J=7.0 Hz), 1.484 (d, 3H, J=7.0 Hz), 1.282 (t, 1H, J=7.2 Hz), 1.256 (s, 3H), 0.684 (d, 3H, J=6.8 Hz), 0.620 (d, 3H, J=7.2 Hz).

Step 10: 2-((3R,5R,6S)-5-(3-chlorophenyl)-6-(4-chlorophenyl)-3-methyl-1-(2S)-3-methyl-1-(N-(2,2,2-trifluoroacetyl)-2-propylsulfonamidine)butyl-2-)-2-oxopiperdine-3-yl)aceticacid

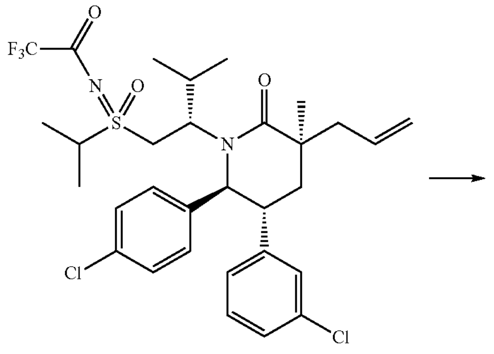

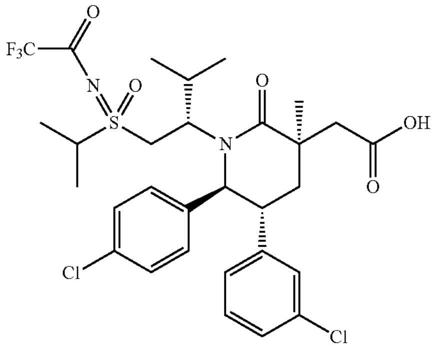

2,2,2-trifluoroaceticn-(((S)-2-((3S,5R,6S)-3-allyl-5-(3-chlorophenyl)-6-(4-chlorophenyl)-3-methyl-2-oxopiperidin-1-yl)-3-methylbutyl)(isopropyl)(oxy)-16-sulfonamidine) (150 mg) and ruthenium trichloride (7.3 mg) were dissolved in DCM/$H_2O$ (5 ml/5 ml), then tetrabutylammonium hydrogen sulfate (15.8 mg) and sodium periodate (300 mg) were added and stirred overnight. After filtration, the filtrate was extracted with DCM. The solution was concentrated to dry and purified by column chromatography with N-heptane/ethyl acetate (1:1) as the eluent to afford 120 mg 2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)acetic acid as the mixture of two isomers, yield 77.6%.

$^1$H NMR (400 MHz, $CD_3OD$) δ 7.27 (br, 4H), 7.19-6.89 (m, 4H), 5.00 (dd, 1H, J=20.4, 11.0 Hz), 4.44 (ddd, 1H, J=28.6, 15.1, 9.2 Hz), 4.08 (m, 1H), 3.71-3.48 (m, 2H), 3.39-3.17 (m, 2H), 3.05-2.92 (m, 1H), 2.67-2.55 (m, 1H), 2.34-1.93 (m, 4H), 1.51 (d, 3H, J=7.1 Hz), 1.47 (d, 3H, J=7.1 Hz), 1.46 (s, 3H), 1.35 (d, 3H, J=3.2 Hz), 0.47 (d, 3H, J=7.0 Hz).

Step 11: 2-((3R,5R,6S)-5-(3-chlorophenyl)-6-(4-chlorophenyl)-3-methyl-1-((2S)-3-methyl-1-(2-propylsulfonamido)butyl-2-)-2-oxo-piperidine-3-yl) acetic acid

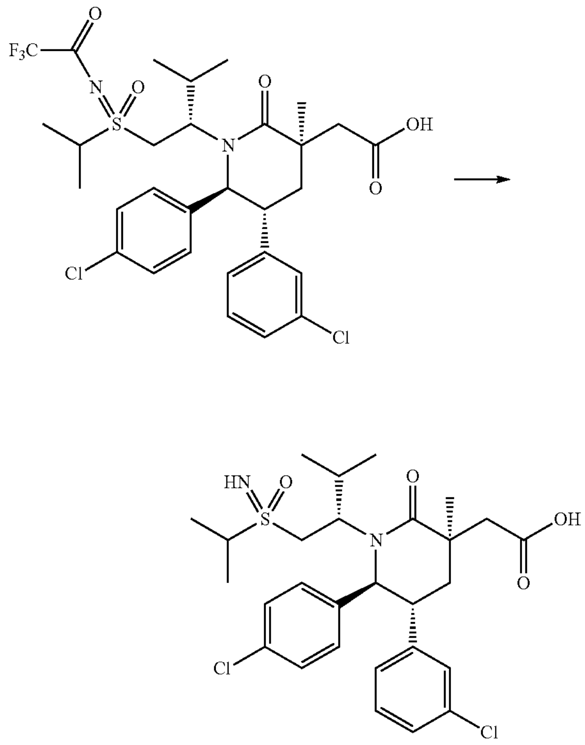

To a solution of 2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)acetic acid (100 mg) in MeOH (2.0 ml) was added potassium carbonate (417 mg). The mixture was stirred at room temperature for 2 hours. Water and ethyl acetate were added into the mixture and adjusted to pH=6 with 3NHCl. After separation, the solution was dried and concentrated and then purified with column chromatography with N-heptane/ethyl acetate (1:1-0:1) as eluent. The yield of high polarity isomer was 31 mg and the yield of low polarity isomer was 18 mg, and total yield was 57%.

High polarity compound 001: $^1$H NMR (400 MHz, $CDCl_3$) δ 7.22 (br, 4H), 7.10-6.91 (m, 3H), 6.84 (dd, 1H, J=5.4, 3.3 Hz), 5.38 (d, 1H, J=11.0 Hz), 4.12-3.97 (m, 1H), 3.40-3.20 (m, 2H), 3.13 (m, 1H), 2.94-2.72 (m, 2H), 2.37 (t, 1H, J=13.7 Hz), 2.19 (m, 1H), 1.91 (dd, 1H, J=13.8, 3.0 Hz), 1.57 (d, 1H, J=6.8 Hz), 1.41 (s, 3H), 1.37 (d, 3H, J=7.1 Hz), 1.35 (d, 3H, J=7.1 Hz), 1.30-1.13 (m, 3H), 0.61 (d, 2H, J=6.6 Hz), 0.44 (d, 2H, J=6.8 Hz).

Low polarity compound 002: $^1$H NMR (400 MHz, $CDCl_3$) δ 7.24 (br, 4H), 7.09-6.95 (m, 3H), 6.86 (dd, 1H, J=5.4, 3.1 Hz), 5.30 (d, 1H, J=11.0 Hz), 3.99 (dd, 1H, J=13.6, 10.4 Hz), 3.46 (t, 1H, J=8.6 Hz), 3.30 (ddd, 1H, J=14.0, 10.9, 3.1 Hz), 3.13 (m, 1H), 2.99-2.76 (m, 3H), 2.37 (t, 1H, J=13.7 Hz), 2.12 (dt, 1H, J=14.9, 6.9 Hz), 1.90 (dd, 1H, J=13.8, 3.0 Hz), 1.43-1.34 (m, 6H), 0.61 (d, 3H, J=6.6 Hz), 0.42 (d, 3H, J=6.9 Hz).

Example 2

Synthesis of 2-((3R,5R,6S)-5-(3-chlorophenyl)-6-(4-chlorophenyl)-3-methyl-1-((2S)-3-methyl-1-(N-methylpropyl-2-sulfonamido)butyl-2-)-2-oxo-piperidine-3-yl) acetic acid

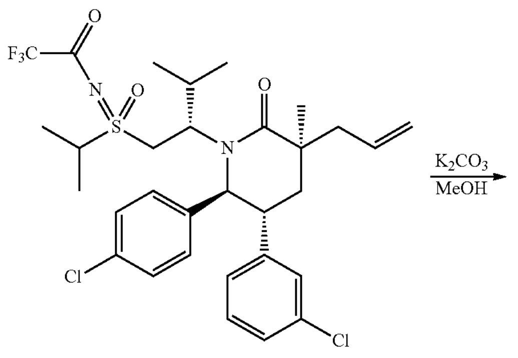

10

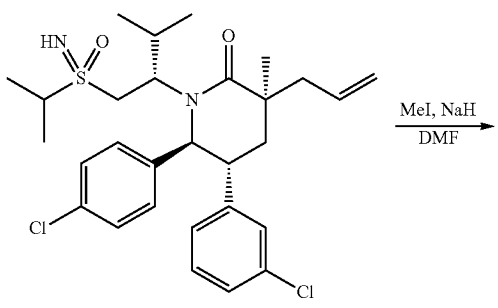

12

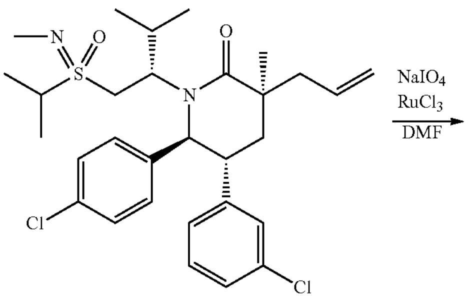

13

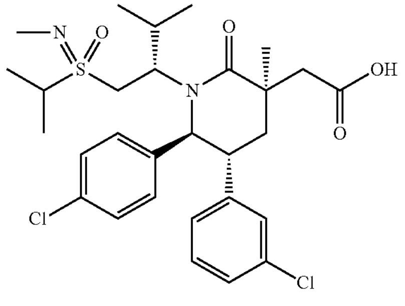

003 & 004

Step 1: (3S,5R,6S)-3-allyl-5-(3-chlorophenyl)-6-(4-chlorophenyl)-3-methyl-1-((2S)-3-methyl-1-(2-propylsulfonamido)butyl-2-)piperidine-2-one

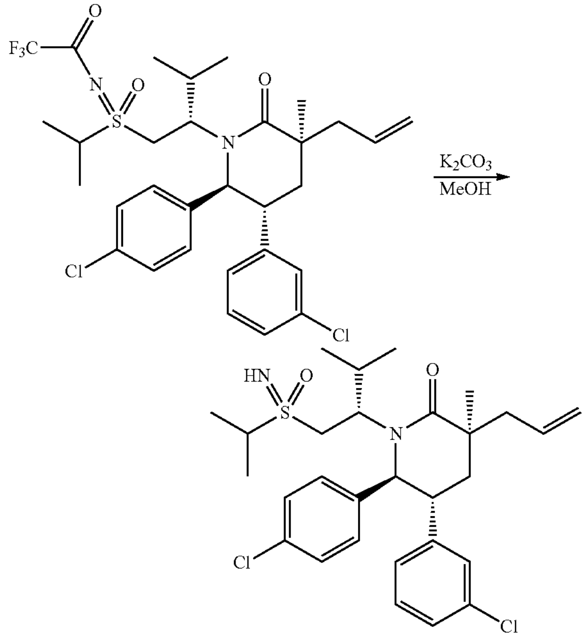

To a solution of 2,2,2-trifluoroaceticn-(((S)-2-((3S,5R, 6S)-3-allyl-5-(3-chlorophenyl)-6-(4-chlorophenyl)-3-methyl-2-oxo-piperidin-1-yl)-3-methylbutyl)(isopropyl)(oxy)-16-sulfonamidine) (512 mg) in MeOH (15 ml) was added potassium carbonate (600 mg), and stirred at room temperature overnight. Water and ethyl acetate were added to separate. The solution was dried and concentrated and then purified with column chromatography with N-heptane/ethyl acetate (1:1-0:1) as eluent to afford 352 mg (3S,5R, 6S)-3-allyl-5-(3-chlorophenyl)-6-(4-chlorophenyl)-3-methyl-1-((2S)-3-methyl-1-(2-propylsulfonamido)butyl-2-)piperidine-2-one as a mixture of two isomers, yield 80%.

1H NMR (400 MHz, $CDCl_3$) δ 7.27 (br, 4H), 7.16-6.97 (m, 3H), 6.97-6.83 (m, 1H), 5.90 (ddt, 1H, J=17.3, 10.1, 7.4 Hz), 5.36 (d, 1H, J=10.9 Hz), 5.31-5.15 (m, 2H), 4.25-4.01 (m, 1H), 3.37 (ddt, 2H, J=13.8, 10.3, 6.1 Hz), 3.28-3.06 (m, 1H), 3.04-2.84 (m, 1H), 2.66 (m, 2H), 2.26 (m, 2H), 1.82 (dd, 1H, J=13.5, 3.2 Hz), 1.67 (s, 2H), 1.40 (d, J=7.0, 3H), 1.37 (d, J=7.0, 3H), 1.22 (s, 3H), 0.66 (d, 3H, J=6.7 Hz), 0.53 (d, 3H, J=6.8 Hz).

Step 2: (3S,5R,6S)-3-allyl-5-(3-chlorophenyl)-6-(4-chlorophenyl)-3-methyl-1-((2S)-3-methyl-1-(N-methyl-2-propylsulfonamido)butyl-2-)piperidine-2-one

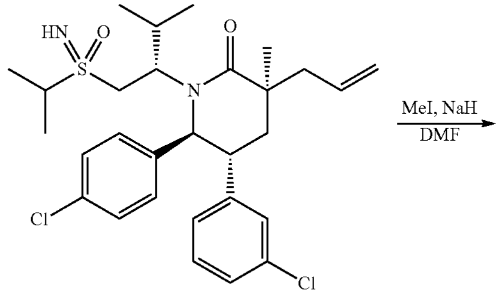

-continued

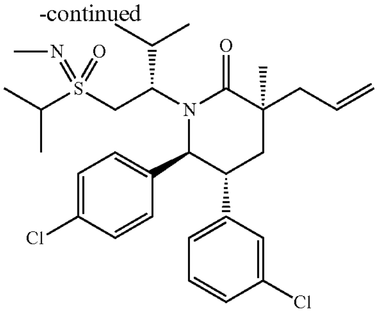

(3S,5R,6S)-3-allyl-5-(3-chlorophenyl)-6-(4-chlorophenyl)-3-methyl-1-((2S)-3-methyl-1-(2-propylsulfonamido) butyl-2-)piperidin-2-one (350 mg) in DMF (7 ml) was cooled to 0° C. and 60% sodium hydride (38 mg) was added. The mixture was stirred for 15 min and iodomethane (180 mg) was added, the mixture was warmed to room temperature to react overnight. Iced water was poured into the mixture and extracted with ethyl acetate. The organic phase was dried over anhydrous sodium sulfate and concentrated. The residue was purified with column chromatography to yield (3S,5R,6S)-3-allyl-5-(3-chlorophenyl)-6-(4-chlorophenyl)-3-methyl-1-((2S)-3-methyl-1-(N-methyl-2-propylsulfonamido)butyl-2-)piperidine-2-one.

Step 3: 2-((3R,5R,6S)-5-(3-chlorophenyl)-6-(4-chlorophenyl)-3-methyl-1-((2S)-3-methyl-1-(N-methyl-2-propylsulfonamido)butyl-2-)-2-oxo-piperidine-3-yl)acetic acid

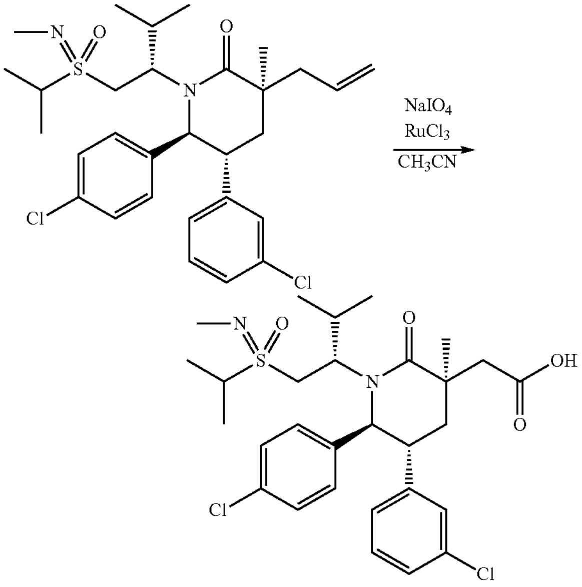

To a solution of (3S,5R,6S)-3-allyl-5-(3-chlorophenyl)-6-(4-chlorophenyl)-3-methyl-1-((2S)-3-methyl-1-(N-methyl-2-propylsulfonamido)butyl-2-)piperidine-2-one (141.6 mg) and ruthenium trichloride (7.8 mg) in the mixture of acetonitrile/water (5 ml/5 ml) was added sodium periodate (322 mg), stirred at room temperature overnight and filtered. The filtrate was extracted with DCM, and the solution was dried and concentrated. The residue was purified with column chromatography with N-heptane/ethyl acetate (1:1) as eluent to afford two isomers of 2-((3R,5R,6S)-5-(3-chlorophenyl)-6-(4-chlorophenyl)-3-methyl-1-((2S)-3-methyl-1-(N-methyl-2-propylsulfonamido)butyl-2-)-2-oxo-piperidine-3-yl)acetic acid.

Low polarity isomer 003, 47.5 mg (yield 32%).

1H NMR (400 MHz, $CDCl_3$) δ 7.59-7.19 (m, 3H), 7.18-7.02 (m, 4H), 6.85 (d, J=7.4 Hz, 1H), 5.24 (d, J=10.9 Hz, 1H), 3.90 (dd, J=13.5, 10.6 Hz, 1H), 3.51-3.24 (m, 4H), 3.03 (d, J=15.0 Hz, 1H), 2.98 (s, 3H), 2.88-2.75 (m, 1H), 2.57 (t, J=13.8 Hz, 1H), 2.20 (dq, J=13.6, 7.2, 6.6 Hz, 2H), 2.00-1.83 (m, 2H), 1.57-1.40 (m, 10H), 1.35-1.25 (m, 3H), 0.90 (t, J=6.7 Hz, 1H), 0.66 (d, J=6.2 Hz, 3H), 0.45 (d, J=6.9 Hz, 2H).

high polarity isomer 004, 40 mg (yield 28%).

1H NMR (400 MHz, $CDCl_3$) δ 7.59-7.19 (m, 3H), 7.15-6.93 (m, 5H), 6.83 (d, J=7.3 Hz, 1H), 5.31 (d, J=11.0 Hz, 1H), 3.97 (m, 1H), 3.42 (m, 1H), 3.28 (m, 3H), 3.04 (d, J=14.7 Hz, 1H), 2.97 (s, 3H), 2.80 (d, J=15.5 Hz, 2H), 2.32 (t, J=13.7 Hz, 1H), 2.26-2.16 (m, 1H), 1.91 (t, J=14.5 Hz, 1H), 1.48 (d, J=6.8 Hz, 3H), 1.43 (d, J=6.8 Hz, 3H), 0.90 (t, J=6.7 Hz, 1H), 0.66 (d, J=6.6 Hz, 3H), 0.50 (d, J=7.0 Hz, 3H).

Example 3

Synthesis of 2-((3R,5R,6S)-5-(3-chlorophenyl)-6-(4-chlorophenyl)-1-(2S)-1-(N-cyanopropyl-2-sulfonamido)-3-methylbut-2)-3-methyl-2-oxo-piperidinyl-3-)acetic acid

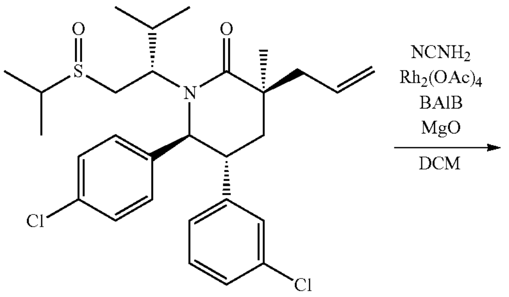

9

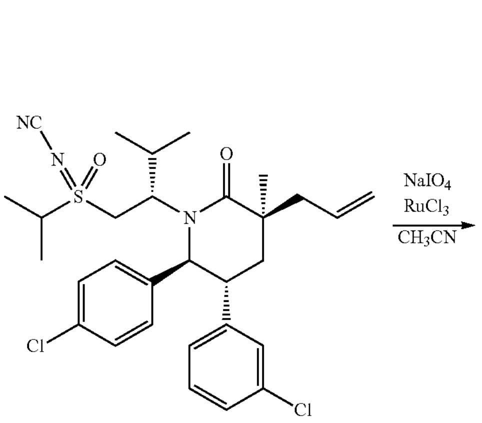

14

-continued

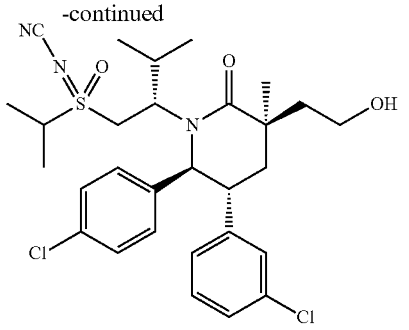

005 & 006

Step 1: Synthesis of N-(((S)-2-((3S,5R,6S)-3-allyl-5-(3-chlorophenyl)-6-(4-chlorophenyl)-3-methyl-2-oxo-piperidin-1-yl)-3-methylbutyl)(isopropyl)(oxy)-16-thio)cyanamide

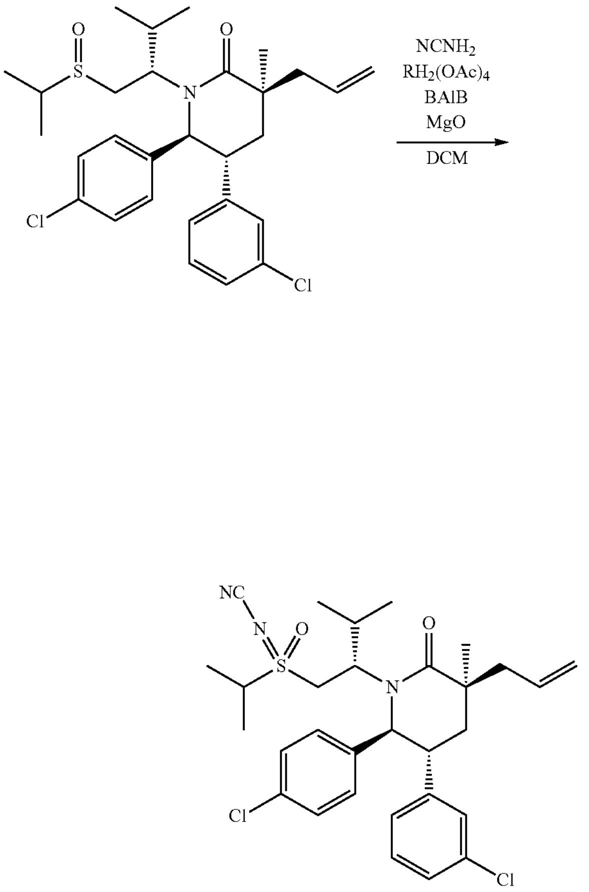

The target compound was prepared according to step 9 of example 1 by replacing trifluoroacetamide with N-(((S)-2-((3S,5R,6S)-3-allyl-5-(3-chlorophenyl)-6-(4-chlorophenyl)-3-methyl-2-oxopiperidin-1-yl)-3-methylbutyl)(isopropyl)(oxy)-16-thio)cyanamide.

Step 2: 2-((3R,5R,6S)-5-(3-chlorophenyl)-6-(4-chlorophenyl)-1-((2S)-1-(N-cyanopropyl-2-sulfonamido)-3-methylbutyl-2-)-3-methyl-2-oxopiperidinyl-3-) acetic acid

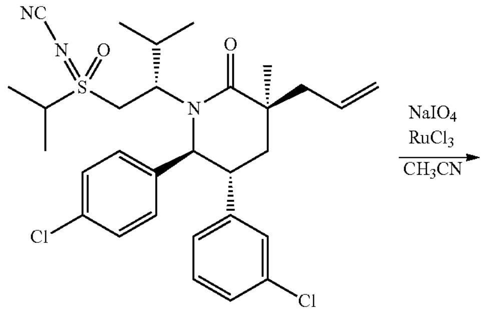

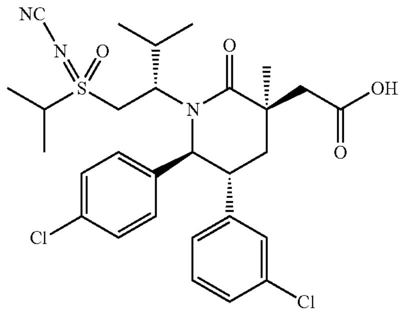

The target compound was prepared according to step 10 of example 1 by replacing 2,2,2-trifluoroacetyl N-(((S)-2-((3S,5R,6S)-3-allyl-5-(3-chlorophenyl)-6-(4-chlorophenyl)-3-methyl-2-oxopiperidin-1-yl)-3-methylbutyl)(isopropyl)(oxy)-16-sulfonamidinoamine with N-(((S)-2-((3S,5R,6S)-3-allyl-5-(3-chlorophenyl)-6-(4-chlorophenyl)-3-methyl-2-oxopiperidin-1-yl)-3-methylbutyl)(isopropyl)(oxy)-16-sulfylidene)cyanamide. A mixture of two isomers of 2-((3R,5R,6S)-5-(3-chlorophenyl)-6-(4-chlorophenyl)-1-((2S)-1-(N-cyanopropyl-2-sulfonamido)-3-methylbutyl-2-)-3-methyl-2-oxopiperidinyl-3-)acetic acid was afforded and separated by pre-HPLC to afford two isomers. Peak 1 was isomer 005: 1H NMR (400 MHz, $CDCl_3$) δ 7.59-7.19 (m, 3H), 7.19-7.04 (m, 3H), 7.04-6.94 (m, 2H), 4.98 (d, J=10.3 Hz, 1H), 4.40 (dd, J=12.5 Hz, 1H), 3.68 (m, 1H), 3.47 (t, J=8.9 Hz, 1H), 3.28 (t, J=12.0 Hz, 1H), 2.93 (dd, J=13.9, 2.0 Hz, 1H), 2.89 (m, 3H), 2.21 (m, 1H), 2.12 (q, J=6.9 Hz, 1H), 2.03 (d, J=13.4 Hz, 1H), 1.63 (d, J=6.2 Hz, 3H), 1.61 (d, J=6.2 Hz, 3H), 1.49 (s, 3H), 0.90 (t, J=6.8 Hz, 2H), 0.66 (d, J=6.6 Hz, 3H), 0.54 (d, J=6.9 Hz, 3H). LC-MS: M+1=592.2.

Peak 2 was isomer 006: 1H NMR (400 MHz, CDCl3) δ 7.59-7.19 (m, 3H), 7.19-7.04 (m, 3H), 7.04-6.94 (m, 2H), 5.01 (d, J=10.3 Hz, 1H), 4.40 (dd, J=12.5 Hz, 1H), 3.66 (tt, J=13.7, 6.8 Hz, 1H), 3.47 (t, J=8.9 Hz, 1H), 3.38 (t, J=12.0 Hz, 1H), 3.00 (dd, J=13.9, 2.0 Hz, 1H), 2.89 (m, 3H), 2.35 (m, 1H), 2.12 (q, J=6.9 Hz, 1H), 2.03 (d, J=13.4 Hz, 1H), 1.63 (d, J=6.2 Hz, 3H), 1.61 (d, J=6.2 Hz, 3H), 1.44 (s, 3H), 0.90 (t, J=6.8 Hz, 2H), 0.70 (d, J=6.6 Hz, 3H), 0.50 (d, J=6.9 Hz, 3H). LC-MS: M+1=592.2.

Example 4: Preparation of Compound 007

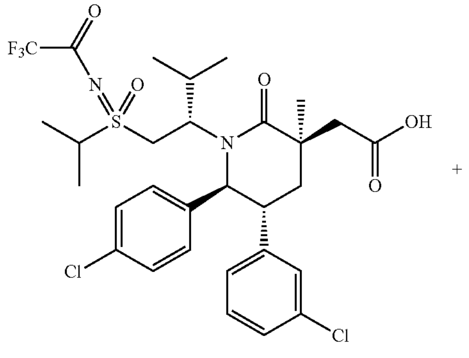

11

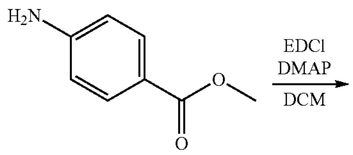

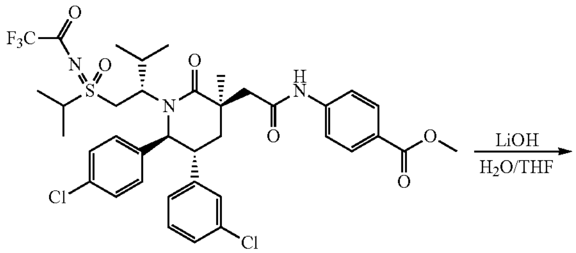

15

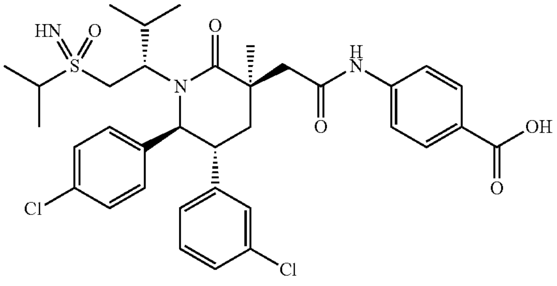

007

Step 1: Synthesis of methyl 4-(2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)acetamino) benzoate

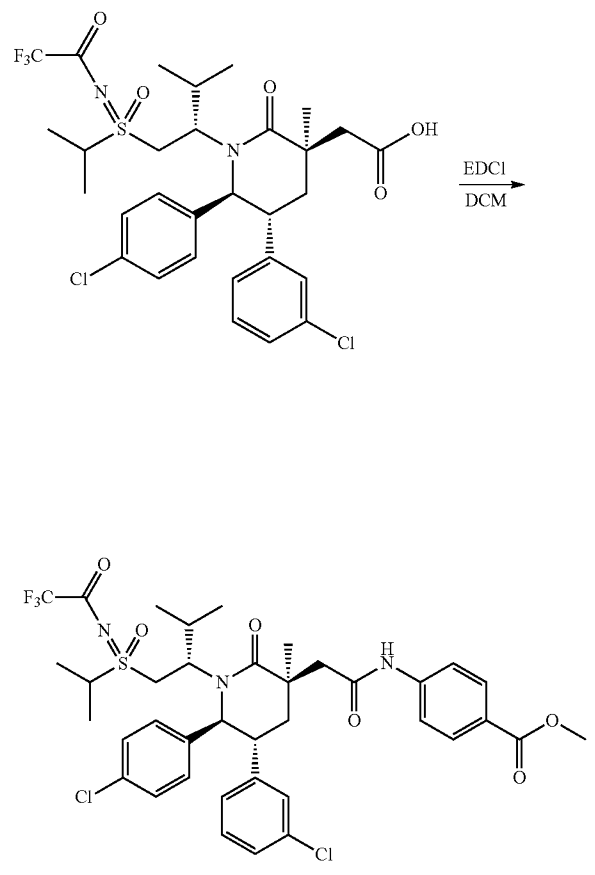

2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)aceticacid (800 mg), methyl p-aminobenzoate (219 mg), DMAP (324 mg) and EDC HCl (508.4 mg) were added successively into DCM under N2 at 0° C. The mixture was then stirred overnight at room temperature. TLC showed that the reaction was completed. $H_2O$ was added to quench the reaction under ice bath. Cold 1NHCl was used to adjust pH to 2. The resulting solution was separated and washed again with 1NHCl, $H_2O$ and saturated brine successively. The organic phase was dried over anhydrous magnesium sulfate and concentrated. The residue was purified with column chromatography to afford 600 mg (63.6%) product as white foam solid.

$^1$H NMR (400 MHz, $CDCl_3$) δ 8.84 (s, 1H), 8.07 (d, J=8.7 Hz, 2H), 7.71 (d, J=8.7 Hz, 2H), 7.27-7.06 (m, 6H), 6.97 (s, 1H), 6.91 (t, J=3.6 Hz, 1H), 4.97 (d, J=10.9 Hz, 1H), 4.56 (dd, J=13.9, 10.6 Hz, 1H), 4.14 (q, J=7.2 Hz, 1H), 3.94 (s, 3H), 3.39 (dd, J=16.4, 11.7 Hz, 3H), 2.89 (q, J=14.4 Hz, 2H), 2.38 (t, J=13.8 Hz, 1H), 2.15-1.92 (m, 2H), 1.58 (d, J=6.8 Hz, 3H), 1.53 (d, J=6.9 Hz, 3H), 1.46 (s, 3H), 0.75 (d, J=6.7 Hz, 3H), 0.36 (d, J=7.0 Hz, 3H).

Step 2: Synthesis of 4-(2-((3R,5R,6S)-5-(3-chlorophenyl)-6-(4-chlorophenyl)-3-methyl-1-((2S)-3-methyl-1-(propylsulfonamido-2-)butyl-2-)-2-oxo-piperidine-3-yl)acetamino)benzoicacid

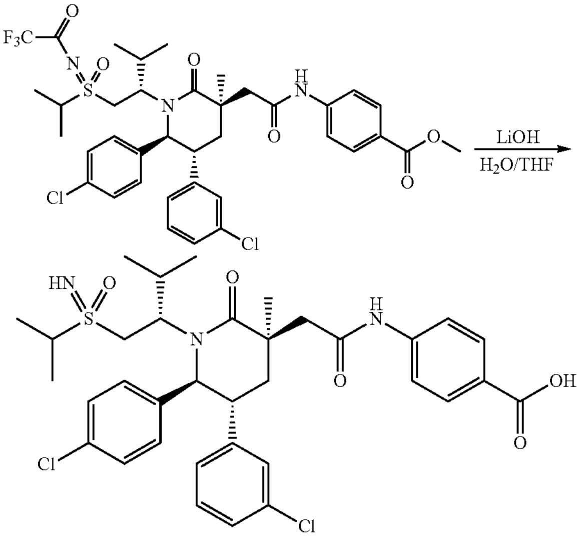

Methyl 4-(2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)acetamino)benzoate (600 mg) and $LiOH.H_2O$ (127 mg) were added into $MeOH/H_2O$/THF (2.4 ml/1.2 ml/1.2 ml) at room temperature. The mixture was stirred at room temperature. TLC showed that the reaction was completed. The mixture was concentrated to remove solvents. $H_2O$ and ethyl acetate was added to the residue, and pH was adjusted to 2 with cold 1NHCl. After separation, the aqueous phase was extracted again with ethyl acetate. The combined organic phase was washed with water and saturated brine, and dried over anhydrous magnesium sulfate. After concentration, the residue was preparative purified and lyophilized to afford 250 mg white solid, yield 48.4%.

$^1$H NMR (400 MHz, $CD_3OD$) δ 8.05 (d, J=7.5 Hz, 2H), 7.81 (d, J=8.7 Hz, 2H), 7.20 (m, 6H), 6.86 (d, J=19.2 Hz, 2H), 5.13 (s, 1H), 5.01 (s, 1H), 4.43 (s, 1H), 3.57 (m, 3H), 3.08 (d, J=13.6 Hz, 1H), 2.67 (d, J=13.9 Hz, 1H), 2.48-2.06 (m, 3H), 1.47 (d, J=38.1 Hz, 9H), 0.77 (s, 3H), 0.59 (s, 3H). LC-MS: M+1=686.2

Example 5

The target compound 008-024 was prepared by substituting methyl p-aminobenzoate with different anilines or sulfonamides under conditions similar to example 4 (see table).

Example 6

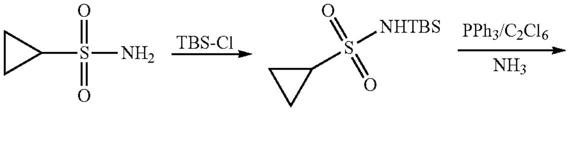

-continued

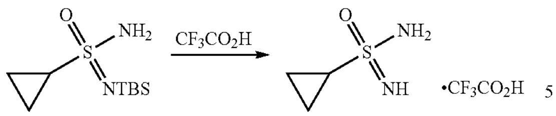

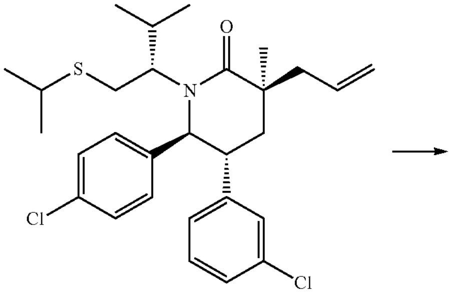

8

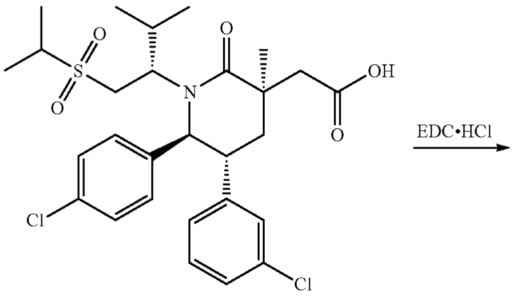

16

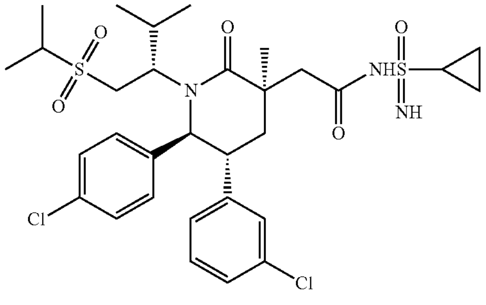

025

Step 1:

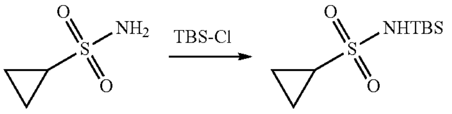

The solution of TBS-Cl (22.5 g) in tolune (75 ml) was added dropwise into a solution of cyclopropylsulfonamide (15 g) and triethylamine (19.3 g) in THF (240 ml). The mixture was then stirred for 48 h at room temperature under N2. MTBE (150 ml) was added into the reaction solution, and the mixture was stirred for 0.5 h at room temperature. The solid was strained off and washed with MTBE. The filtrate was mixed with silica gel and purified with column chromatography to afford 17.8 g (y=52%) white solid. $^1$H NMR (400 MHz, $CDCl_3$) δ 4.28 (s, 1H), 2.61-2.35 (m, 1H), 1.22-1.10 (m, 2H), 1.03-0.99 (m, 2H), 0.97 (s, 9H), 0.31 (s, 6H).

Step 2:

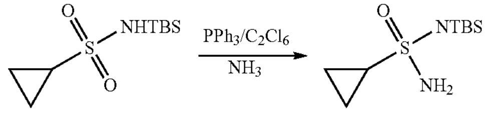

$PPh_3$ (13.4 g) and $C_2Cl_6$ (12.1 g) was added into a flask under N2 at room temperature, and replaced with vacuum for three times, then redistilled chloroform (100 ml) was added as solvent, and the mixture was warmed to 50° C. and kept for 2 h. After cooled to 0° C., anhydrous TEA was added to the reaction solution and stirred for 30 min before adding N-tert-butyldimethylsilyl cyclopropane sulfonamide (10 g) in chloroform (40 ml). The mixture was kept at the same temperature and stirred for 30 min. Finally, anhydrous ammonia was introduced into the reaction solution (about 20 min) and large amount of solid was precipitated. TLC showed that the reaction was completed. The solid was strained off and washed with MTBE. The filtrate was mixed with silica gel and purified with column chromatography to afford 9.4 g white solid (yield 94%). $^1$H NMR (400 MHz, $CDCl_3$) δ 4.50 (s, 2H), 2.59 (ddd, J=12.6, 7.8, 4.7 Hz, 1H), 1.16-1.08 (m, 1H), 1.02 (ddd, J=15.7, 6.6, 4.2 Hz, 1H), 0.96-0.91 (m, 2H), 0.89 (s, 9H), 0.11 (s, 3H), 0.11 (s, 3H).

Step 3:

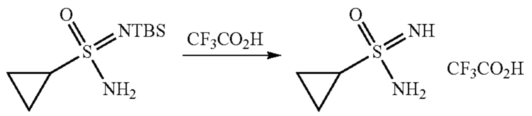

To a solution of N'-cyclopropylsulfonamidamide (8.5 g) in DCM (15 ml) was added dropwise TFA (5 ml) under $N_2$ in ice bath. The mixture was then stirred for 2 h at room temperature. TLC showed that the reaction was completed. The solution was concentrated, and the residue was dissolved in tolune and concentrated once more. The resulting residue was pulped with MTBE, filtered to afford white solid, and dried under vacuum to provide 7.5 g product (y=80%). $^1$H NMR (400 MHz, DMSO-d6) δ 8.74 (s, 3H), 3.07 (tt, J=7.8, 3.9 Hz, 1H), 1.33-1.12 (m, 4H).

Step 4:

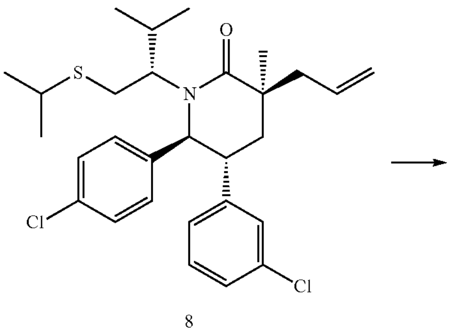

8

-continued

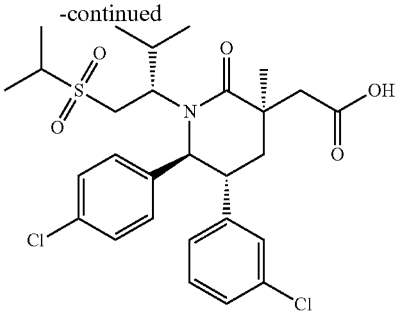

16

The target compound was prepared according to step 10 of example 1 by replacing 2,2,2-trifluoroacetyl N-(((S)-2-((3S,5R,6S)-3-allyl-5-(3-chlorophenyl)-6-(4-chlorophenyl)-3-methyl-2-oxopiperidin-1-yl)-3-methylbutyl)(isopropyl)(oxy)-16-sulfonamidine) with (3S,5R,6S)-3-allyl-5-(3-chlorophenyl)-6-(4-chlorophenyl)-1-((S)-1-(isopropylmercapto)-3-methylbutyl-2)-3-methylpiperidine-2-one to provide 2-((3R,5R,6S)-5-(3-chlorophenyl)-6-(4-chlorophenyl)-1-((S)-1-(isopropylsulfonyl)-3-methylbutyl-2-)-3-methyl-2-oxopiperdinyl-3-)acetic acid.

$^1$H NMR (400 MHz, $CD_3OD$) δ 7.30 (s, 3H), 7.18-7.07 (m, 4H), 7.03 (dt, J=7.5, 1.5 Hz, 1H), 5.13 (d, J=11.0 Hz, 1H), 4.02 (dd, J=13.9, 10.4 Hz, 1H), 3.63 (ddd, J=13.9, 11.1, 3.1 Hz, 1H), 3.12 (dd, J=13.9, 2.1 Hz, 1H), 2.90 (d, J=13.4 Hz, 1H), 2.50 (d, J=13.3 Hz, 1H), 2.28 (t, J=13.6 Hz, 1H), 2.25-2.17 (m, 1H), 2.11 (dd, J=13.6, 3.2 Hz, 1H), 1.43 (d, J=6.8 Hz, 6H), 1.37 (s, 3H), 0.68 (d, J=6.6 Hz, 3H), 0.54 (d, J=6.9 Hz, 3H).

Step 5:

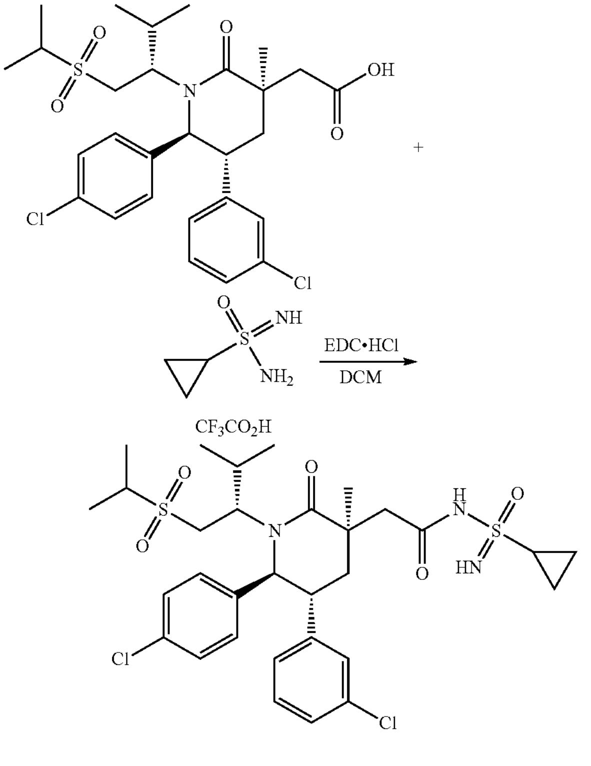

2-((3R,5R,6S)-5-(3-chlorophenyl)-6-(4-chlorophenyl)-1-((S)-1-(isopropylsulfonyl)-3-methylbutyl-2-)-3-methyl-2-oxopiperdinyl-3-)acetic acid (800 mg), cyclopropylsulfonamidine sulfonamide trifluoroacetate (705.3 mg), DMAP (736.4 mg), EDC HCl (508.4 mg) were added successively into DCM under N2 at 0° C. The mixture was then stirred for 18 h at room temperature. HPLC monitored that the starting material was consumed. The reaction solution was washed with 1N HCl, separated and extracted with DCM. The organic phase was washed with saturated brine and dried over anhydrous magnesium sulfate, and concentrated to provide 940 mg crude product as foam solid. A potion of crude product was purified by pre-HPLC to yield 28.6 mg target compound (HPLC purity: 97.6%).

$^1$H NMR (400 MHz, $CD_3OD$) δ 7.29 (br, 4H), 7.18-7.05 (m, 4H), 5.13 (d, J=11.1 Hz, 1H), 4.09-3.97 (m, 1H), 3.78-3.62 (m, 1H), 3.30 (m, 1H), 3.19-3.07 (m, 1H), 3.00 (dd, J=12.8, 2.1 Hz, 1H), 2.97-2.91 (m, 1H), 2.62-2.49 (m, 1H), 2.33-2.08 (m, 3H), 1.43 (d, J=6.8 Hz, 6H), 1.40 (s, 3H), 1.29-0.95 (m, 5H), 0.67 (d, J=6.6 Hz, 3H), 0.53 (d, J=6.9 Hz, 3H). LC-MS: M+1=670.2

Example 7

Step 1:

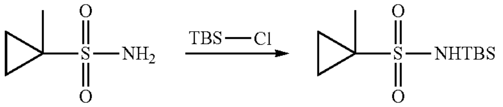

To a solution of 1-methylcyclopropyl sulfonamide (4.5 g) and triethylamine (6.74 g) in THF (80 ml) was added the solution of TBS-Cl (6.05 g) in tolune (30 ml) dropwise at room temperature under N2. The mixture was then stirred for 48 h. TLC showed that the reaction was completed. MTBE (150 ml) was added into the reaction solution. The mixture was stirred for 30 min at room temperature. The solid was strained off and washed with MTBE. The filtrate was mixed with silica gel, purified by column chromatography to afford white solid 2.9 g (y=43.9%). $^1$H NMR (400 MHz, $CDCl_3$) δ 4.08 (br, 1H), 1.55 (s, 3H), 1.38 (t, J=3.0 Hz, 2H), 0.97 (s, 9H), 0.80-0.74 (m, 2H), 0.29 (s, 6H).

Step 2

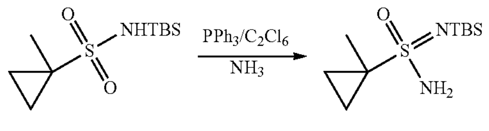

$PPh_3$ (3.65 g) and $C_2Cl_6$ (3.3 g) were added into a flask under $N_2$ at room temperature, and replaced with vacuum for three times, then redistilled chloroform (70 ml) was added as solvent, and the mixture was warmed to 50° C. and kept for 2 h. After cooled to 0° C., anhydrous TEA (4.7 g) was added to the reaction solution and stirred for 30 min. Then N-tert-butyldimethylsilyl cyclopropane sulfonamide (10 g) in chloroform (40 ml) was added. The mixture was kept at the same temperature and stirred for 30 min. Finally, anhydrous ammonia was introduced into the reaction solution (about 20 min) and large amount of solid was precipitated. TLC showed that the reaction was completed. The solid was strained off and washed with MTBE. The filtrate was mixed with silica gel and purified with column chromatography to afford 2.3 g white solid (y=79.3%).

Step 3:

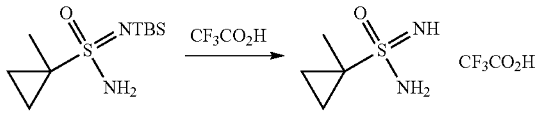

To a solution of N'-(tertbutyldimethylsilyl)-1-methylcyclopropylsulfonamidamide (2.3 g) in DCM was added TFA (5 ml). The mixture was then stirred at room temperature for 2 h. TLC showed that the reaction was completed. The reaction solution was concentrated and the residue was dissolved in tolune and concentrated once more. The resulting residue was pulped with MTBE, filtered to afford white solid, and dried to provide 1.87 g (y=81.3%) product.

Step 4

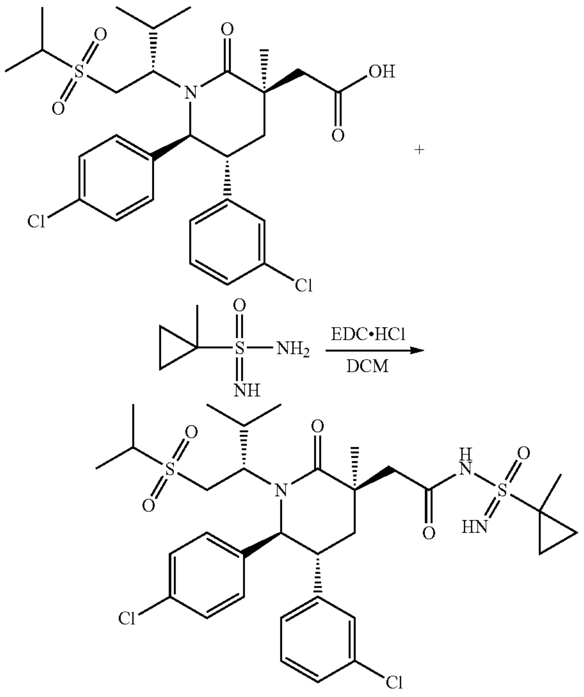

A pair of isomers was obtained under conditions similar to step 5 of example 6.

028A: $^1H$ NMR (400 MHz, $CD_3OD$) δ 7.28 (br, 3H), 7.17-7.06 (m, 5H), 5.11 (d, J=11.1 Hz, 1H), 4.03 (dd, J=13.7, 10.5 Hz, 1H), 3.73-3.64 (m, 1H), 3.30 (d, J=7.3 Hz, 2H), 3.12 (d, J=13.8 Hz, 1H), 3.04 (d, J=12.9 Hz, 1H), 2.54 (d, J=12.9 Hz, 1H), 2.27 (t, J=13.4 Hz, 1H), 2.23-2.15 (m, 2H), 1.55 (s, 4H), 1.43 (d, J=6.9 Hz, 6H), 1.39 (s, 3H), 1.00-0.84 (m, 3H), 0.68 (d, J=6.6 Hz, 3H), 0.52 (d, J=6.9 Hz, 3H). LC-MS: M+1=684.2

028B: $^1H$ NMR (400 MHz, $CD_3OD$) δ 7.23 (br, 4H), 7.16-7.12 (m, 2H), 7.09 (dd, J=6.0, 4.5 Hz, 2H), 5.11 (d, J=11.1 Hz, 1H), 4.03 (dd, J=13.7, 10.6 Hz, 1H), 3.67 (t, J=10.7 Hz, 1H), 3.30 (d, J=4.0 Hz, 2H), 3.11 (d, J=13.7 Hz, 1H), 3.01 (d, J=12.8 Hz, 1H), 2.52 (d, J=12.8 Hz, 1H), 2.30 (d, J=13.5 Hz, 1H), 2.26-2.20 (m, 1H), 2.16 (dd, J=13.5, 3.2 Hz, 1H), 1.54 (s, 3H), 1.53-1.48 (m, 1H), 1.43 (d, J=6.8 Hz, 7H), 1.38 (s, 3H), 0.97-0.83 (m, 3H), 0.68 (d, J=6.6 Hz, 3H), 0.54 (d, J=6.9 Hz, 3H). LC-MS: M+1=684.2

Example 8

Synthetic Route

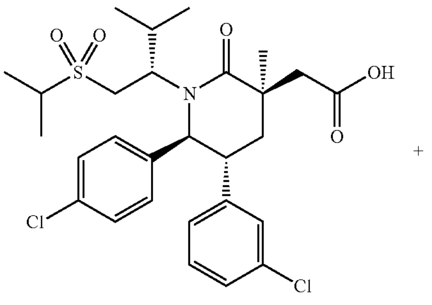

16

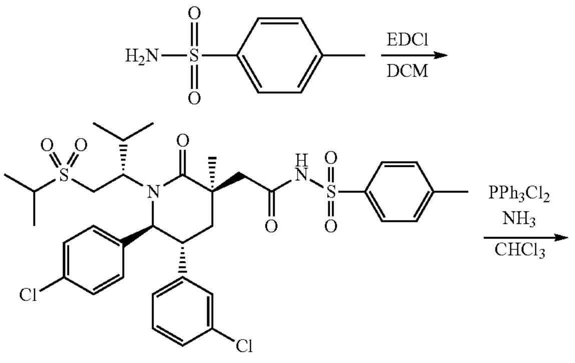

17

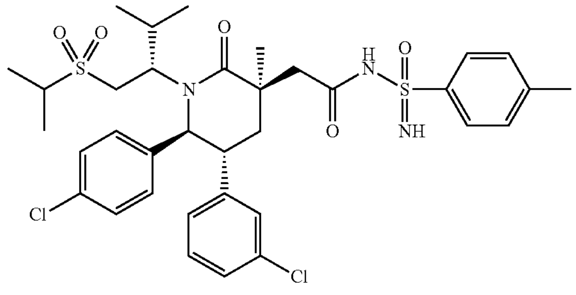 [SMILES: Cc1ccc(S(=O)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1]

029

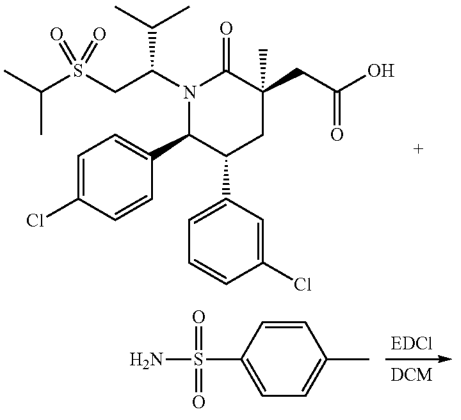

-continued

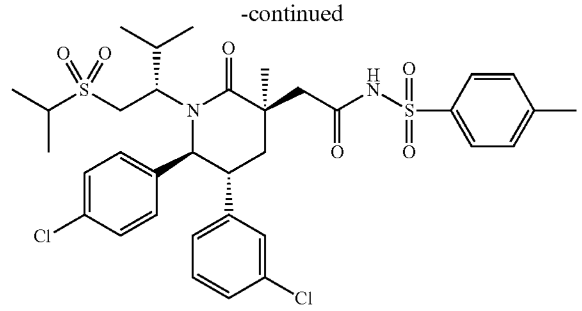

Step 1:

2-((3R,5R,6S)-5-(3-chlorophenyl)-6-(4-chlorophenyl)-1-((S)-1-(isopropylsulfonyl)-3-methylbutyl-2-)-3-methyl-2-oxopiperdinyl-3-)acetic acid (600 mg), p-toluenesulfonamide (271 mg), DMAP (284 mg) and EDC HCl (445 mg) were added successively in DCM (12 ml) under N2 at 0° C. The mixture was then stirred for 18 h at room temperature. HPLC showed that the reaction was completed. The reaction solution was washed with 1NHCl, separated, and aqueous phase was extracted with DCM. The combined organic phase was washed with saturated brine and dried over anhydrous magnesium sulfate. The solution was concentrated to provide 565 mg (y=74.3%) crude product as foam solid.

$^1$H NMR (400 MHz, $CDCl_3$) δ 10.93 (s, 1H), 8.00 (d, J=8.2 Hz, 2H), 7.40 (br, 1H), 7.35 (d, J=8.2 Hz, 2H), 7.27-7.12 (m, 3H), 7.09 (d, J=4.7 Hz, 2H), 6.97 (s, 1H), 6.93-6.84 (m, 1H), 5.12 (d, J=11.0 Hz, 1H), 4.09 (dd, J=13.6, 10.7 Hz, 1H), 3.35 (t, J=9.2 Hz, 1H), 3.26-3.11 (m, 2H), 2.88 (t, J=13.4 Hz, 2H), 2.62 (d, J=15.0 Hz, 1H), 2.46 (s, 3H), 2.39 (s, 1H), 2.31-2.21 (m, 1H), 1.87 (d, J=13.1 Hz, 1H), 1.47 (d, J=6.9 Hz, 6H), 1.31 (s, 3H), 0.71 (d, J=6.6 Hz, 3H), 0.49 (d, J=6.9 Hz, 3H).

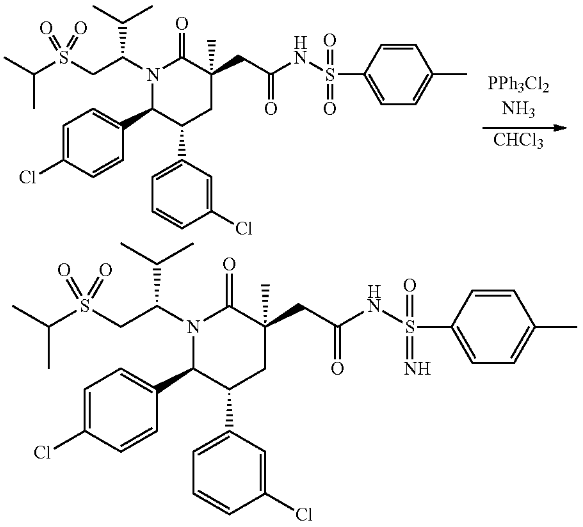

Step 2:

$PPh_3$ (250 mg) and $C_2Cl_6$ (223 mg) were added into a flask, and replaced with N2 by oil pump, then redistilled chloroform (10 ml) was added to dissolve. The mixture was heated to 50° C. for 2 h and large amount of white solid was precipitated. After cooled to 0° C., anhydrous TEA (284 mg) was added and stirred for 30 min, then 2-((3R,5R,6S)-5-(3-chlorophenyl)-6-(4-chlorophenyl)-1-((S)-1-(isopropylsulfonyl)-3-methylbutyl-2-)-3-methyl-2-oxo-piperidinyl-3-)-N-p-toluenesulfonamide (565 mg) in chloroform (10 ml) was added. The mixture was kept at the same temperature for 30 min, and anhydrous ammonia was introduced into the reaction solution for about 20 min. LCMS showed that target compound was formed. The reaction solution was diluted with DCM and washed with $H_2O$, and dried over anhydrous magnesium sulfate. The solution was concentrated and purified with pre-HPLC to afford the product as solid.

$^1$H NMR (400 MHz, $CD_3OD$) δ 7.74 (br, 1H), 7.60 (d, J=8.3 Hz, 2H), 7.33 (br, 3H), 7.15 (d, J=6.5 Hz, 2H), 7.09 (d, J=8.0 Hz, 2H), 7.01 (s, 1H), 6.94 (d, J=7.3 Hz, 1H), 5.03 (d, J=11.2 Hz, 1H), 4.04-3.93 (m, 1H), 3.63-3.52 (m, 1H), 3.31-3.25 (m, 2H), 3.09 (dd, J=13.7, 1.8 Hz, 1H), 3.00 (d, J=13.0 Hz, 1H), 2.52 (d, J=12.9 Hz, 1H), 2.33 (s, 3H), 2.18-2.08 (m, 1H), 2.01 (t, J=13.5 Hz, 1H), 1.74 (dd, J=13.7, 2.8 Hz, 1H), 1.41 (d, J=6.9 Hz, 6H), 1.23 (s, 3H), 0.65 (d, J=6.6 Hz, 3H), 0.46 (d, J=6.9 Hz, 3H). LC-MS: M+1=720.2

Example 9

Synthetic Route:

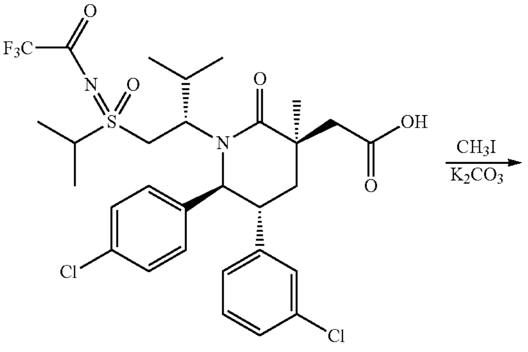

11

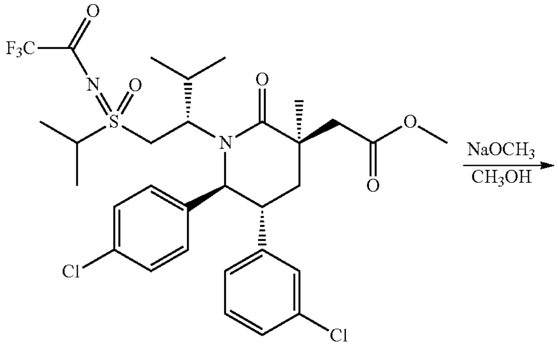

16

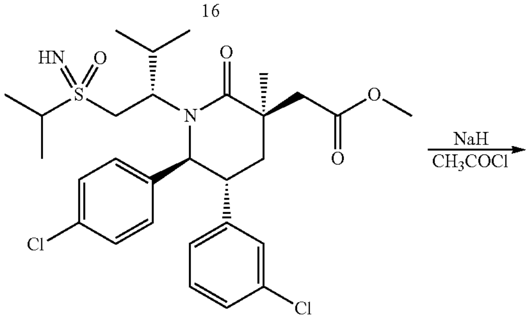

19

-continued

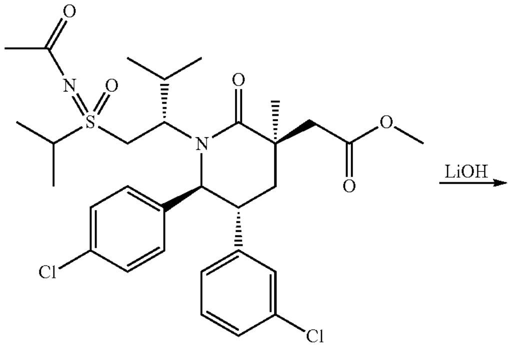

20

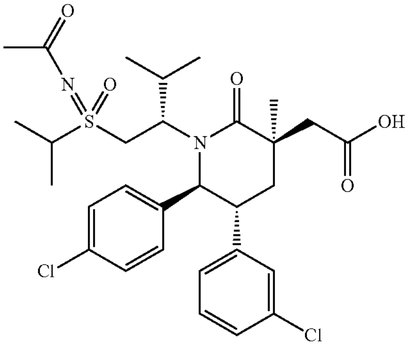

039

Step 1:

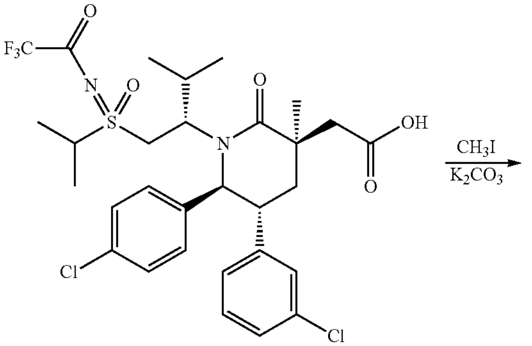

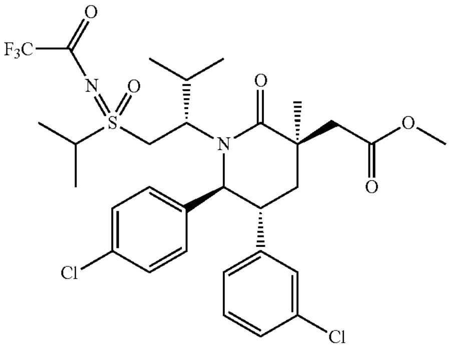

2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)aceticacid (800 mg) in acetone (10 ml) was added anhydrous potassium carbonate (333 mg), and finally methyl iodide (342 mg) was added under N2. The mixture was stirred at room temperature for 5-6 h. TLC showed that the reaction was completed. The solid was strained off and washed with ethyl acetate. The filtrate was concentrated and the residue was extracted with ethyl acetate/$H_2O$. The aqueous phase was extracted again with ethyl acetate. The combined organic phase was washed with saturated brine and dried over anhydrous magnesium sulfate. The solution was concentrated and purified with column chromatography to afford 775 mg product as white solid.

Step 2:

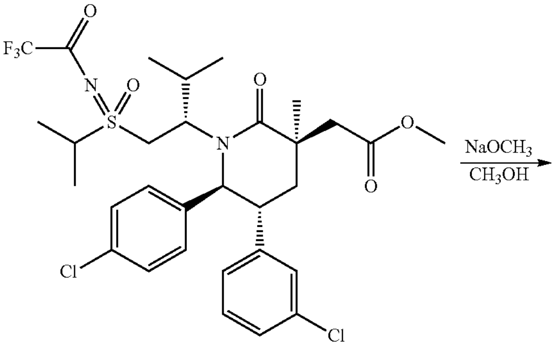

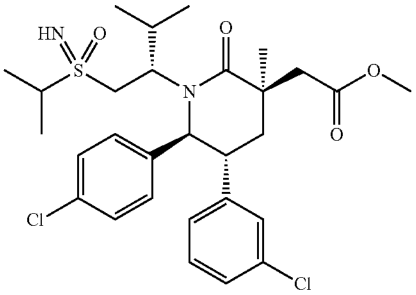

To a solution of methyl 2-((3R,5R,6S)-5-(3-chlorophenyl)-6-(4-chlorophenyl)-3-methyl-1-((2S)-3-methyl-1-(N-(2,2,2-trifluoroacetyl)-2-propylsulfonamido)butyl-2-)-2-oxo-piperidine-3-yl)acetate (775 mg) in anhydrous methanol (10 ml) was added 30% sodium methoxide in methanol (5 ml) in ice bath under N2. The mixture was stirred to reach room temperature. TLC showed that the reaction was completed. Acetic acid was used to adjust pH to 6 in ice bath. The mixture was concentrated to remove methanol and the residue was extracted with ethyl acetate/$H_2O$. The aqueous phase was extracted with ethyl acetate again and the combined ethyl acetate phase was washed with saturated brine solution and dried over anhydrous magnesium sulfate. The solution was concentrated and purified with column chromatography to afford 556 mg product as white solid (y=83.4%).

Step 3 and 4

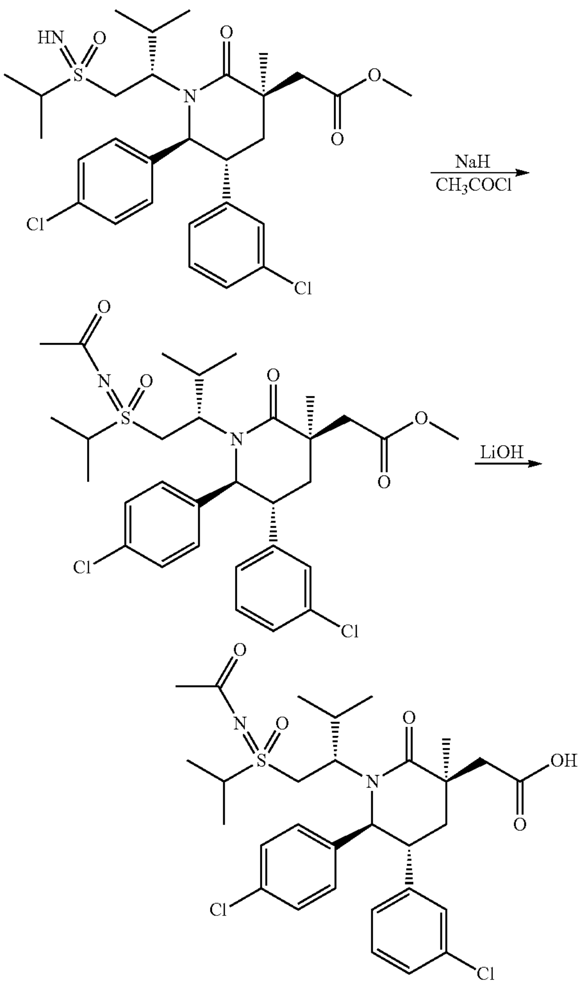

Compound 19 (200 mg) was dissolved in DCM (5 ml) under $N_2$. NaH (60%, 20.6 mg) was added to the mixture and stirred for 10 min under ice salt bath. Acetylchlorine (30 mg) was added and the mixture was warmed to room temperature and stirred for 2 h. Lithium hydroxide hydrate (42.8 mg), water (20 ml) and methanol (20 ml) were added to the mixture at 0° C. and then stirred for 2 h at room temperature. 2N HCl was added to adjust pH to 4. The methanol was removed by concentration under vacuum, and the residue was extracted with ethyl acetate. The combined organic phase was washed with saturated brine and dried over anhydrous magnesium sulfate. The solution was concentrated and purified by column chromatography to yield target product as white solid.

$^1$H NMR (400 MHz, $CD_3OD$) δ 7.51-6.97 (m, 8H), 5.13 (d, J=11.0 Hz, 1H), 4.35 (dd, J=14.1, 10.4 Hz, 1H), 4.08 (p, J=7.0 Hz, 1H), 3.61-3.52 (m, 2H), 3.32-3.29 (m, 1H), 3.00 (d, J=12.9 Hz, 1H), 2.63 (d, J=12.2 Hz, 1H), 2.30 (t, J=13.7 Hz, 1H), 2.19-2.05 (m, 2H), 2.13 (s, 3H), 1.51 (d, J=6.8 Hz, 3H), 1.46 (d, J=6.9 Hz, 3H), 1.39 (s, 3H), 0.67 (d, J=6.6 Hz, 3H), 0.51 (d, J=6.9 Hz, 3H). LC-MS: M+1=609.2

Example 10

The target compound 041 was prepared by referring to example 9, by replacing acetyl chloride with acryloyl chloride; the target compound 045 was prepared by replacing acetyl chlorine with dimethylaminoacyl chloride; the target compound 046 was prepared by replacing acetyl chloride with 4-morpholinocarbonyl chloride; the target compound 047 was prepared by replacing acetyl chloride with 1-pyrrolidine carbonyl chloride; the target compound 048 was prepared by replacing acetylchlorine with ethyl chloroformate.

Example 11

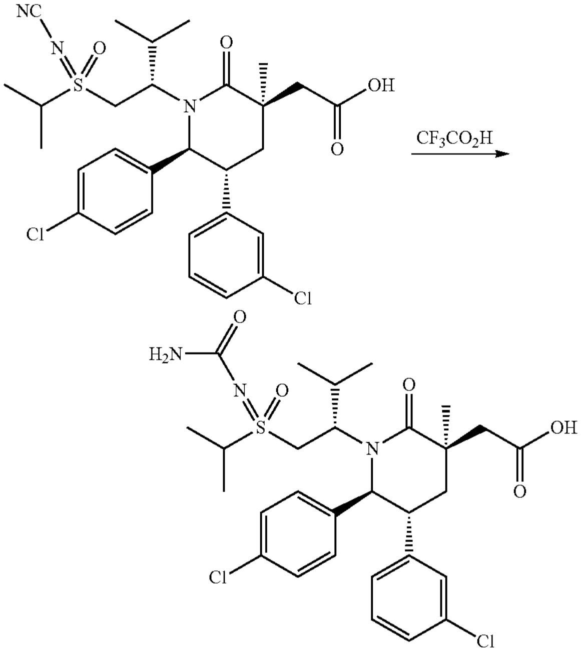

A solution of compound 006 (200 mg) in DCM/TFA (5 ml/0.3 ml) was heated to reflux for 2 h. The cooled reaction solution was adjusted to 4 by sodium bicarbonate and separated. The mixture was extracted with ethyl acetate twice. The combined organic phase was washed with saturated brine and dried over anhydrous magnesium sulfate. The solution was concentrated and purified by pre-HPLC to provide the target compound 034.

$^1$H NMR (400 MHz, $CD_3OD$) δ 7.95-6.95 (m, 10H), 5.22 (d, J=11.1 Hz, 1H), 4.25 (dd, J=13.8, 10.4 Hz, 1H), 4.05 (p, J=6.9 Hz, 1H), 3.62-3.52 (m, 1H), 3.51-3.40 (m, 2H), 3.00 (d, J=13.5 Hz, 1H), 2.63 (d, J=13.6 Hz, 1H), 2.34 (t, J=13.7 Hz, 1H), 2.15 (dt, J=14.1, 7.0 Hz, 1H), 2.05 (dd, J=13.6, 2.9 Hz, 1H), 1.48 (t, J=7.1 Hz, 6H), 1.39 (s, 3H), 0.68 (d, J=6.6 Hz, 3H), 0.50 (d, J=6.9 Hz, 3H). LC-MS: M+1=610.2

Example 12

The target compound 054 was prepared by replacing compound 11 with compound 034 by referring to example 4. $^1$H NMR (400 MHz, DMSO-d6) δ 12.82 (s, 1H), 9.61 (s, 1H), 8.27 (d, J=8.2 Hz, 1H), 7.58 (dd, J=8.4, 1.8 Hz, 1H), 7.52 (d, J=1.8 Hz, 1H), 7.50-7.06 (m, 6H), 6.96 (d, J=7.5 Hz, 1H), 6.84 (s, 1H), 5.13 (d, J=11.1 Hz, 1H), 4.08 (dd, J=14.0, 10.3 Hz, 1H), 3.94 (q, J=7.0 Hz, 1H), 3.87 (s, 3H), 3.57 (t, J=12.8 Hz, 1H), 3.47 (d, J=13.4 Hz, 1H), 3.22 (t, J=9.6 Hz, 1H), 3.11 (d, J=13.5 Hz, 1H), 2.84 (d, J=13.3 Hz, 1H), 2.18-1.98 (m, 4H), 1.37 (d, J=6.7 Hz, 3H), 1.33 (d, J=6.9 Hz, 2H), 1.29 (s, 2H), 0.55 (d, J=6.5 Hz, 3H), 0.41 (d, J=6.9 Hz, 3H). LC-MS: M+1=759.2.

Example 13

The target compound 042, 043, 049, 050, 051, 052 and 053 were prepared under conditions similar to example 4.

TABLE B

| number | Structure | Analytical data |
|---|---|---|
| 001 | 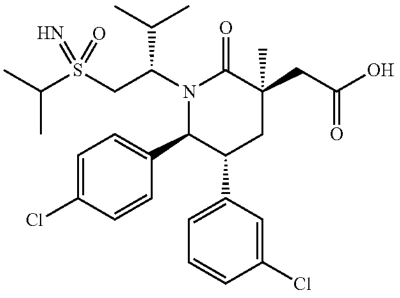 Isomer with high TLC polarity | $^1$HNMR($CDCl_3$, 400 MHz): 7.3-6.8(m, 7H), 6.838(d, 1H, J = 6.8 Hz), 5.382(d, 1H, J = 11.2 Hz), 4.055(m, 1H), 3.332(t, 1H, J = 8.4 Hz), 3.258(t, 1H, J = 8.6 Hz), 3.128(m, 1H), 2.842(m, 2H), 2.370(t, 1H, J = 13.6 Hz), 2.182(m, 1H), 1.911(dd, 1H, J = 2.0, 13.7 Hz), 1.568(d, 1H, J = 6.8 Hz), 1.423(s, 3H), 1.391(d, 3H, J = 7.0 Hz), 1.354(d, 3H, J = 7.0 Hz), 0.610(d, 3H, J = 6.3 Hz), 0.458(d, 3H, J = 7.0 Hz). LC-MS: M + 1 = 567.2 |
| 002 | 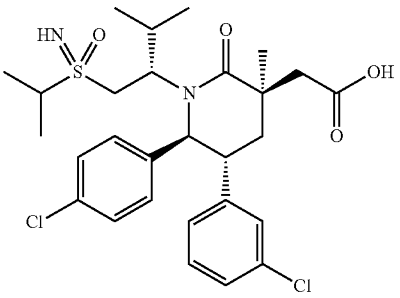 [SMILES: CC(C)[C@@H](CS(=N)(=O)C(C)C)N1C(=O)[C@@](C)(CC(=O)O)C[C@H](c2cccc(Cl)c2)[C@H]1c1ccc(Cl)cc1] Isomer with low TLC polarity | $^1$HNMR($CDCl_3$, 400 MHz): 7.3-6.8(m, 7H), 6.854(d, 1H, J = 6.4 Hz), 5.304(d, 1H, J = 10.8 Hz), 3.988(dd, 1H, J = 10.4, 13.2 Hz), 3.461(t, 1H, J = 8.4 Hz), 3.304(dt, 1H, J = 2.8, 13.6 Hz), 3.129(m, 1H), 2.943(d, 1H, J = 12.8 Hz), 2.878(d, 1H, J = 14.8 Hz), 2.799(d, 1H, J = 14.4 Hz), 2.371(t, 1H, J = 13.6 Hz), 2.123(m, 1H), 1.898(dd, 1H, J = 2.4, 13.6 Hz), 1.568(dd, 1H, J = 2.0, 6.8 Hz), 1.398(d, 3H, J = 7.0 Hz), 1.382(d, 3H, J = 7.0 Hz), 0.610(d, 3H, J = 6.7 Hz), 0.418(d, 3H, J = 7.1 Hz). LC-MS: M + 1 = 567.2 |
| 003 | 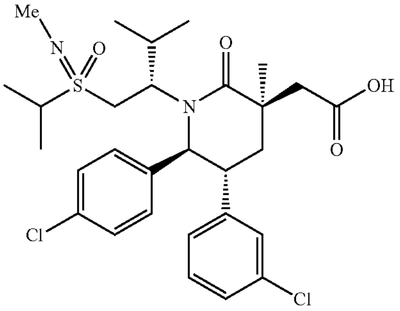 [SMILES: CN=S(=O)(C[C@H](C(C)C)N1C(=O)[C@@](C)(CC(=O)O)C[C@H](c2cccc(Cl)c2)[C@H]1c1ccc(Cl)cc1)C(C)C] Isomer with low TLC polarity | 1H NMR(400 MHz, $CDCl_3$) δ 7.59-7.19(m, 3H), 7.18-7.02(m, 4H), 6.85(d, J = 7.4 Hz, 1H), 5.24(d, J = 10.9 Hz, 1H), 3.90(dd, J = 13.5, 10.6 Hz, 1H), 3.51-3.24(m, 4H), 3.03(d, J = 15.0 Hz, 1H), 2.98(s, 3H), 2.88-2.75(m, 1H), 2.57(t, J = 13.8 Hz, 1H), 2.20(dq, J = 13.6, 7.2, 6.6 Hz, 2H), 2.00-1.83(m, 2H), 1.57-1.40(m, 10H), 1.35-1.25(m, 3H), 0.90(t, J = 6.7 Hz, 1H), 0.66(d, J = 6.2 Hz, 3H), 0.45(d, J = 6.9 Hz, 2H). LC-MS: M + 1 = 580.9 |
| 004 | 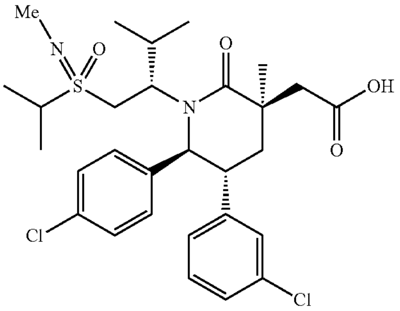 [SMILES: CN=S(=O)(C[C@H](C(C)C)N1C(=O)[C@@](C)(CC(=O)O)C[C@H](c2cccc(Cl)c2)[C@H]1c1ccc(Cl)cc1)C(C)C] Isomer with high TLC polarity | 1H NMR(400 MHz, $CDCl_3$) δ 7.59-7.19(m, 3H), 7.15-6.93(m, 5H), 6.83(d, J = 7.3 Hz, 1H), 5.31(d, J = 11.0 Hz, 1H), 3.97(m, 1H), 3.42(m, 1H), 3.28(m, 3H), 3.04(d, J = 14.7 Hz, 1H), 2.97(s, 3H), 2.80(d, J = 15.5 Hz, 2H), 2.32(t, J = 13.7 Hz, 1H), 2.26-2.16(m, 1H), 1.91(t, J = 14.5 Hz, 1H), 1.48(d, J = 6.8 Hz, 3H), 1.43(d, J = 6.8 Hz, 3H), 0.90(t, J = 6.7 Hz, 1H), 0.66(d, J = 6.6 Hz, 3H), 0.50(d, J = 7.0 Hz, 3H). LC-MS: M + 1 = 580.9 |

TABLE B-continued

| number | Structure | Analytical data |
| --- | --- | --- |
| 005 | 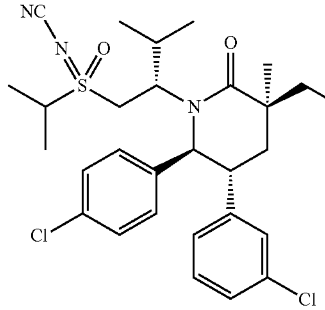 peak 1 isomer in HPLC | $^1$H NMR(400 MHz, $CDCl_3$) δ 7.59-7.19(m, 3H), 7.19-7.04(m, 3H), 7.04-6.94(m, 2H), 4.98(d, J = 10.3 Hz, 1H), 4.40(dd, J = 12.5 Hz, 1H), 3.68(m, 1H), 3.47(t, J = 8.9 Hz, 1H), 3.28(t, J = 12.0 Hz, 1H), 2.93(dd, J = 13.9, 2.0 Hz, 1H), 2.89(m, 3H), 2.21(m, 1H), 2.12(q, J = 6.9 Hz, 1H), 2.03(d, J = 13.4 Hz, 1H), 1.63(d, J = 6.2 Hz, 3H), 1.61(d, J = 6.2 Hz, 3H), 1.49(s, 3H), 0.90(t, J = 6.8 Hz, 2H), 0.66(d, J = 6.6 Hz, 3H), 0.54(d, J = 6.9 Hz, 3H). LC-MS: M + 1 = 592.2 |
| 006 | 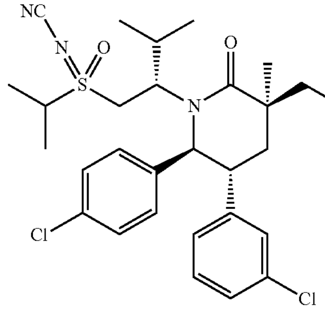 peak 2 isomer in HPLC | $^1$H NMR(400 MHz, $CDCl_3$) δ 7.59-7.19(m, 3H), 7.19-7.04(m, 3H), 7.04-6.94(m, 2H), 5.01(d, J = 10.3 Hz, 1H), 4.40(dd, J = 12.5 Hz, 1H), 3.66(tt, J = 13.7, 6.8 Hz, 1H), 3.47(t, J = 8.9 Hz, 1H), 3.38(t, J = 12.0 Hz, 1H), 3.00(dd, J = 13.9, 2.0 Hz, 1H), 2.89(m, 3H), 2.35(m, 1H), 2.12(q, J = 6.9 Hz, 1H), 2.03(d, J = 13.4 Hz, 1H), 1.63(d, J = 6.2 Hz, 3H), 1.61(d, J = 6.2 Hz, 3H), 1.44(s, 3H), 0.90(t, J = 6.8 Hz, 2H), 0.70(d, J = 6.6 Hz, 3H), 0.50(d, J = 6.9 Hz, 3H). LC-MS: M + 1 = 592.2 |
| 007 | 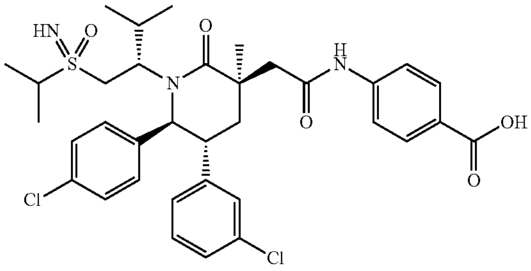 [SMILES: CC(C)[C@@H](CS(=N)(=O)C(C)C)N1C(=O)[C@@](C)(CC(=O)Nc2ccc(C(=O)O)cc2)C[C@H](c2cccc(Cl)c2)[C@H]1c1ccc(Cl)cc1] | $^1$H NMR(400 MHz, $CD_3OD$) δ 8.05(d, J = 7.5 Hz, 2H), 7.81(d, J = 8.7 Hz, 2H), 7.20(m, 6H), 6.86(d, J = 19.2 Hz, 2H), 5.13(s, 1H), 5.01(s, 1H), 4.43(s, 1H), 3.57(m, 3H), 3.08(d, J = 13.6 Hz, 1H), 2.67(d, J = 13.9 Hz, 1H), 2.48-2.06(m, 3H), 1.47(d, J = 38.1 Hz, 9H), 0.77(s, 3H), 0.59(s, 3H). LC-MS: M + 1 = 686.2 |
| 008 | 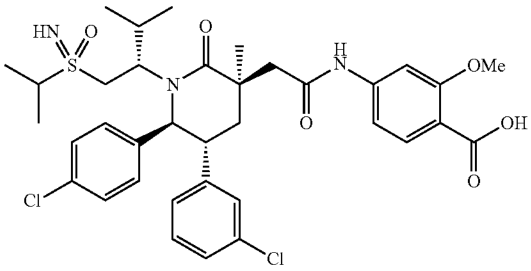 [SMILES: COc1cc(NC(=O)C[C@@]2(C)C[C@H](c3cccc(Cl)c3)[C@@H](c3ccc(Cl)cc3)N([C@H](CS(=N)(=O)C(C)C)C(C)C)C2=O)ccc1C(=O)O] | $^1$H NMR(400 MHz, $CD_3OD$) δ 7.65(d, J = 8.3 Hz, 1H), 7.59(d, J = 1.6 Hz, 1H), 7.20(m, 4H), 7.07(d, J = 4.8 Hz, 2H), 6.98(s, 1H), 6.86(t, J = 4.9 Hz, 1H), 5.36(d, J = 11.2 Hz, 1H), 4.04(dd, J = 13.8, 10.6 Hz, 1H), 3.89(s, 3H), 3.61-3.46(m, 2H), 3.26(dt, J = 13.4, 6.8 Hz, 1H), 3.12-3.00(m, 3H), 2.61(d, J = 13.3 Hz, 1H), 2.39(t, J = 13.7 Hz, 1H), 2.22(dq, J = 13.8, 7.2, 6.6 Hz, 1H), 2.14(dd, J = 13.8, 3.0 Hz, 1H), 1.50-1.37(m, 9H), 0.72(d, J = 6.6 Hz, 3H), 0.57(d, J = 6.9 Hz, 3H). LC-MS: M + 1 = 716.2 |
| 009 | 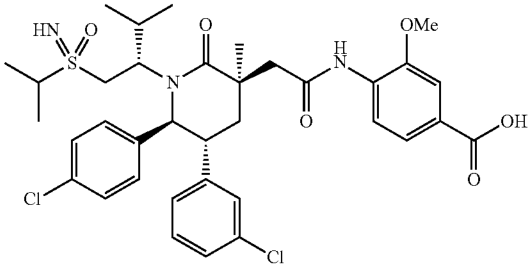 [SMILES: COc1cc(C(=O)O)ccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] | $^1$H NMR(400 MHz, $CD_3OD$) δ 8.40(d, J = 8.4 Hz, 1H), 7.79(s, 1H), 7.73(d, J = 8.4 Hz, 1H), 7.66(s, 1H), 7.09(m, 5H), 6.84(s, 2H), 5.05(d, J = 10.6 Hz, 1H), 4.57(s, 1H), 3.89(s, 3H), 3.74(s, 1H), 3.60-3.37(m, 3H), 3.11(d, J = 13.4 Hz, 1H), 2.83(d, J = 13.4 Hz, 1H), 2.33(t, J = 13.8 Hz, 1H), 2.28-2.08(m, 2H), 1.54(d, J = 6.2 Hz, 6H), 1.43(s, 3H), 0.78(d, J = 5 .7 Hz, 3H), 0.57(d, J = 5.1 Hz, 3H). LC-MS: M + 1 = 716.2 |

TABLE B-continued

| number | Structure | Analytical data |
|---|---|---|
| 010 | 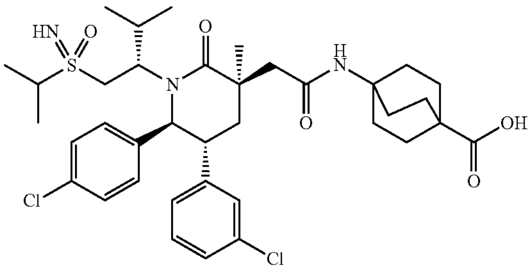 [SMILES: CC(C)[C@@H](CS(=N)(=O)C(C)C)N1C(=O)[C@@](C)(CC(=O)NC23CCC(C(=O)O)(CC2)CC3)C[C@H](c2cccc(Cl)c2)[C@H]1c1ccc(Cl)cc1] | $^1H$ NMR(400 MHz, $CD_3OD$) δ 7.68(s, 1H), 7.46-7.12(m, 5H), 7.08(s, 1H), 7.00(d, J = 6.6 Hz, 1H), 5.12(d, J = 11.1 Hz, 1H), 4.50-4.39(m, 1H), 3.58(d, J = 8.3 Hz, 2H), 3.52-3.40(m, 1H), 2.81(d, J = 13.5 Hz, 1H), 2.47(d, J = 13.6 Hz, 1H), 2.30-2.16(m, 2H), 2.06(dd, J = 13.4, 2.8 Hz, 1H), 2.01-1.87(m, 13H), 1.52(t, J = 6.0 Hz, 6H), 1.35(s, 3H), 0.75(d, J = 6.3 Hz, 3H), 0.56(d, J = 6.6 Hz, 3H). LC-MS: M + 1 = 718.2 |
| 011 | 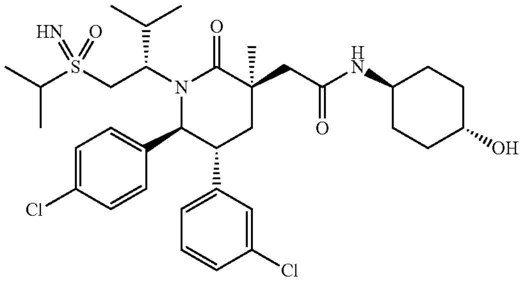 [SMILES: CC(C)[C@@H](CS(=N)(=O)C(C)C)N1C(=O)[C@@](C)(CC(=O)N[C@H]2CC[C@H](O)CC2)C[C@H](c2cccc(Cl)c2)[C@H]1c1ccc(Cl)cc1] | $^1H$ NMR(400 MHz, $CD_3OD$) δ 7.62-7.18(m, 4H), 7.15(d, J = 6.8 Hz, 2H), 7.04(s, 1H), 6.99(d, J = 4.6 Hz, 1H), 5.09(d, J = 12.9 Hz, 1H), 4.56-4.40(m, 1H), 3.75-3.62(m, 2H), 3.62-3.51(m, 2H), 3.51-3.40(m, 2H), 2.88(d, J = 13.4 Hz, 1H), 2.47(d, J = 13.4 Hz, 1H), 2.31-2.19(m, 2H), 2.07(dd, J = 13.6, 2.9 Hz, 1H), 2.01-1.89(m, 4H), 1.53(t, J = 5.9 Hz, 6H), 1.37(m, 7H), 0.75(d, J = 6.3 Hz, 3H), 0.57(d, J = 6.2 Hz, 3H). LC-MS: M + 1 = 664.2 |
| 012 | 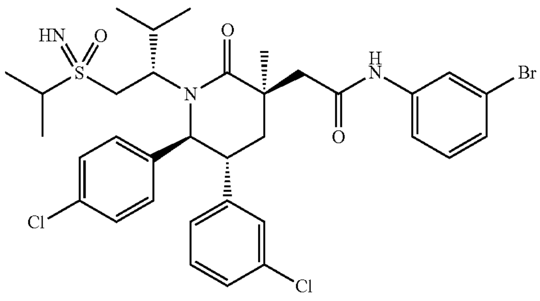 | $^1H$ NMR(400 MHz, $CD_3OD$) δ 8.12(s, 1H), 7.86(m, 1H), 7.54(d, J = 7.0 Hz, 1H), 7.49-7.10(m, 5H), 7.06(d, J = 4.9 Hz, 2H), 6.89(s, 1H), 6.83(t, J = 4.3 Hz, 1H), 5.35(d, J = 11.1 Hz, 1H), 4.04(dd, J = 13.9, 10.6 Hz, 1H), 3.54(t, J = 9.1 Hz, 1H), 3.49-3.39(m, 1H), 3.26(dt, J = 13.7, 6.9 Hz, 1H), 3.05(dd, J = 16.2, 13.8 Hz, 2H), 2.58(d, J = 13.2 Hz, 1H), 2.39(t, J = 13.8 Hz, 1H), 2.22(dq, J = 13.2, 6.4 Hz, 1H), 2.10(dd, J = 13.6, 2.7 Hz, 1H), 1.42(dd, J = 14.2, 7.1 Hz, 9H), 0.72(d, J = 6.6 Hz, 3H), 0.58(d, J = 6.9 Hz, 3H). LC-MS: M + 1 = 720.2 |
| 013 | 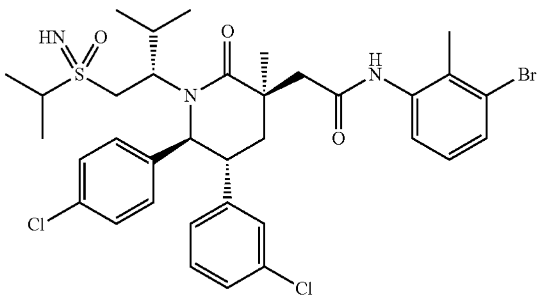 [SMILES: Cc1c(Br)cccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] | $^1H$ NMR(400 MHz, $CD_3OD$) δ 7.50(d, J = 7.5 Hz, 1H), 7.38(d, J = 7.8 Hz, 1H), 7.31(br, 4H), 7.16-7.10(m, 3H), 7.07(s, 1H), 7.01(d, J = 6.5 Hz, 1H), 5.39(d, J = 11.1 Hz, 1H), 4.16-4.02(m, 1H), 3.63(t, J = 13.2 Hz, 1H), 3.57-3.48(m, 1H), 3.30-3.22(m, 1H), 3.09(t, J = 12.0 Hz, 2H), 2.80(d, J = 13.7 Hz, 1H), 2.41(t, J = 13.6 Hz, 1H), 2.34(s, 3H), 2.19(m, 2H), 1.45(m, 9H), 0.70(d, J = 6.6 Hz, 3H), 0.54(d, J = 6.9 Hz, 3H). LCMS: M + 1 = 734.2 |
| 014 | 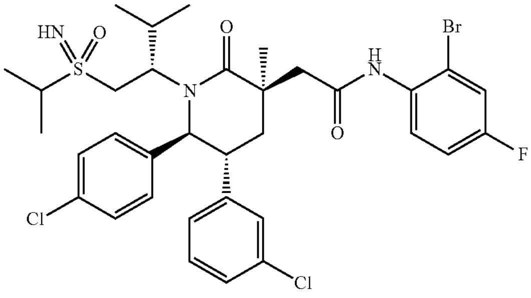 [SMILES: CC(C)[C@@H](CS(=N)(=O)C(C)C)N1C(=O)[C@@](C)(CC(=O)Nc2ccc(F)cc2Br)C[C@H](c2cccc(Cl)c2)[C@H]1c1ccc(Cl)cc1] | $^1H$ NMR(400 MHz, $CD_3OD$) δ 7.69(dd, J = 9.0, 5.6 Hz, 2H), 7.49(dd, J = 8.1, 2.8 Hz, 1H), 7.46-7.15(m, 3H), 7.13(d, J = 5.4 Hz, 2H), 7.03(s, 1H), 7.00-6.93(m, 1H), 5.12(d, J = 10.4 Hz, 1H), 4.65-4.29(m, 1H), 3.65(t, J = 11.8 Hz, 2H), 3.56-3.44(m, 1H), 3.39(d, J = 17.0 Hz, 1H), 3.15(d, J = 13.8 Hz, 1H), 2.84(d, J = 13.8 Hz, 1H), 2.34(t, J = 13.6 Hz, 1H), 2.29-2.11(m, 2H), 1.52(m, 9H), 0.76(d, J = 6.1 Hz, 3H), 0.57(d, J = 5.8 Hz, 3H). LC-MS: M + 1 = 738.0 |

TABLE B-continued

| number | Structure | Analytical data |
|---|---|---|
| 015 | 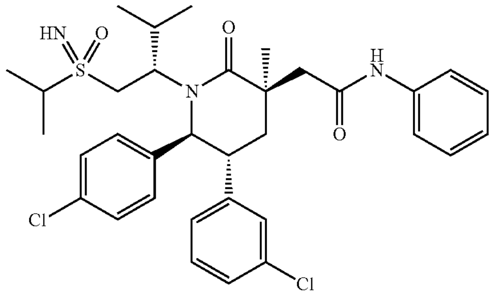 [SMILES: CC(C)[C@@H](CS(=N)(=O)C(C)C)N1C(=O)[C@@](C)(CC(=O)Nc2ccccc2)C[C@H](c2cccc(Cl)c2)[C@H]1c1ccc(Cl)cc1] | $^1$H NMR(400 MHz, $CD_3OD$) δ 7.93-7.71(m, 1H), 7.68(d, J = 8.1 Hz, 2H), 7.64-7.42(m, 1H), 7.38(t, J = 7.9 Hz, 2H), 7.35-7.20(m, 2H), 7.17(t, J = 7.4 Hz, 1H), 7.07(q, J = 8.0 Hz, 2H), 6.91(s, 1H), 6.82(d, J = 6.0 Hz, 1H), 5.11(d, J = 10.8 Hz, 1H), 4.57-4.38(m, 1H), 3.72-3.59(m, 1H), 3.59-3.43(m, 2H), 3.41-3.35(m, 1H), 3.05(d, J = 13.3 Hz, 1H), 2.62(d, J = 13.3 Hz, 1H), 2.33(t, J = 13.8 Hz, 1H), 2.29-2.22(m, 1H), 2.18(dd, J = 13.7, 3.0 Hz, 1H), 1.59-1.48(m, 6H), 1.42(s, 3H), 0.78(d, J = 5.4 Hz, 3H), 0.59(d, J = 5.5 Hz, 3H). LCMS: M + 1 = 642.2 |
| 016 | 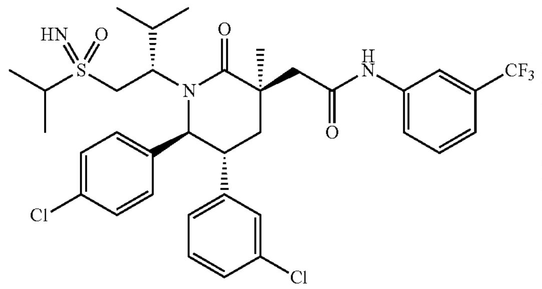 [SMILES: CC(C)[C@@H](CS(=N)(=O)C(C)C)N1C(=O)[C@@](C)(CC(=O)Nc2cccc(C(F)(F)F)c2)C[C@H](c2cccc(Cl)c2)[C@H]1c1ccc(Cl)cc1] | $^1$H NMR(400 MHz, $CD_3OD$) δ 8.21(s, 1H), 7.83(d, J = 8.4 Hz, 1H), 7.58(t, J = 7.9 Hz, 1H), 7.46(d, J = 7.7 Hz, 1H), 7.42-7.13(m, 3H), 7.07(q, J = 8.1 Hz, 3H), 6.88(s, 1H), 6.80(d, J = 7 .5 Hz, 1H), 5.15(d, J = 11.1 Hz, 1H), 4.51-4.27(m, 1H), 3.68-3.40(m, 3H), 3.29(m, 1H), 3.07(d, J = 13.3 Hz, 1H), 2.64(d, J = 13.4 Hz, 1H), 2.36(t, J = 13.8 Hz, 1H), 2.25(dt, J = 13.5, 6.6 Hz, 1H), 2.17(dd, J = 13.8, 2.8 Hz, 1H), 1.52(dd, J = 6.7, 4.7 Hz, 6H), 1.42(s, 3H), 0.77(d, J = 6.5 Hz, 3H), 0.60(d, J = 6.3 Hz, 3H). LC-MS: M + 1 = 710.2 |
| 017 | 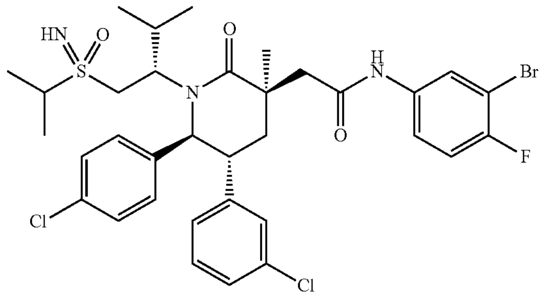 [SMILES: CC(C)[C@@H](CS(=N)(=O)C(C)C)N1C(=O)[C@@](C)(CC(=O)Nc2ccc(F)c(Br)c2)C[C@H](c2cccc(Cl)c2)[C@H]1c1ccc(Cl)cc1] | $^1$H NMR(400 MHz, $CD_3OD$) δ 8.23-8.10(m, 1H), 8.03-7.61(m, 1H), 7.56(dd, J = 11.6, 4.2 Hz, 1H), 7.52-7.26(m, 2H), 7.24(t, J = 8.7 Hz, 2H), 7.09(d, J = 4.7 Hz, 3H), 6.91-6.78(m, 2H), 5.15(d, J = 11.6 Hz, 2H), 4.51-4.27(m, 1H), 3.68-3.54(m, 1H), 3.54-3.42(m, 2H), 3.04(d, J = 13.3 Hz, 1H), 2.61(d, J = 13.4 Hz, 1H), 2.35(t, J = 13.8 Hz, 1H), 2.23(dt, J = 13.0, 6.5 Hz, 1H), 2.14(dd, J = 13.4, 2.9 Hz, 1H), 1.58-1.47(m, 6H), 1.41(s, 3H), 0.77(d, J = 6.3 Hz, 3H), 0.60(d, J = 6.6 Hz, 3H). LC-MS: M + 1 = 738.2 |
| 018 | 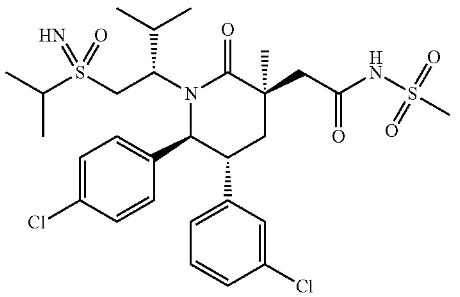 [SMILES: CC(C)[C@@H](CS(=N)(=O)C(C)C)N1C(=O)[C@@](C)(CC(=O)NS(C)(=O)=O)C[C@H](c2cccc(Cl)c2)[C@H]1c1ccc(Cl)cc1] | $^1$H NMR(400 MHz, $CD_3OD$) δ 7.56-7.17(m, 4H), 7.13(m, 3H), 7.03(d, J = 7.9 Hz, 1H), 5.13(d, J = 10.2 Hz, 1H), 4.47-4.35(m, 1H), 3.68-3.46(m, 4H), 2.97(d, J = 13.8 Hz, 1H), 2.54(d, J = 13.9 Hz, 1H), 2.33(t, J = 13.9 Hz, 1H), 2.28-2.17(m, 1H), 2.09(dd, J = 13.8, 2.9 Hz, 1H), 1.52(dd, J = 6.6, 4.9 Hz, 6H), 1.39(s, 3H), 0.75(d, J = 6.5 Hz, 3H), 0.58(d, J = 6.7 Hz, 3H). LC-MS: M + 1 = 644.2 |
| 019 | 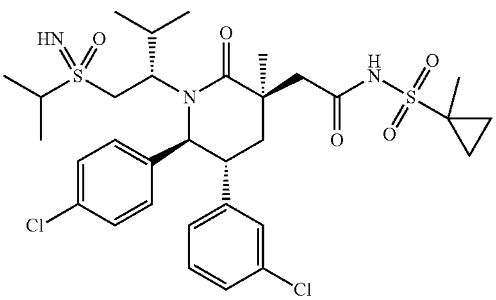 [SMILES: CC(C)[C@@H](CS(=N)(=O)C(C)C)N1C(=O)[C@@](C)(CC(=O)NS(=O)(=O)C2(C)CC2)C[C@H](c2cccc(Cl)c2)[C@H]1c1ccc(Cl)cc1] | $^1$H NMR(400 MHz, $CD_3OD$) δ 7.49-7.16(m, 4H), 7.15-7.05(m, 4H), 5.35(d, J = 11.1 Hz, 1H), 4.02(dd, J = 13.7, 10.7 Hz, 1H), 3.54(dd, J = 17.6, 9.5 Hz, 2H), 3.26(dt, J = 13.5, 6.8 Hz, 1H), 3.09-3.04(m, 1H), 3.00(d, J = 14.1 Hz, 1H), 2.56(d, J = 14.1 Hz, 1H), 2.37(t, J = 14.0 Hz, 1H), 2.24-2.16(m, 1H), 2.06(dd, J = 13.8, 3.0 Hz, 1H), 1.69(m, 1H), 1.59(m, 1H), 1.56(s, 3H), 1.43(t, J = 6.8 Hz, 6H), 1.39(s, 3H), 0.98-0.92(m, 2H), 0.70(d, J = 6.6 Hz, 3H), 0.55(d, J = 6.9 Hz, 3H). LC-MS: M + 1 = 684.2 |

TABLE B-continued

| number | Structure | Analytical data |
|---|---|---|
| 020 | 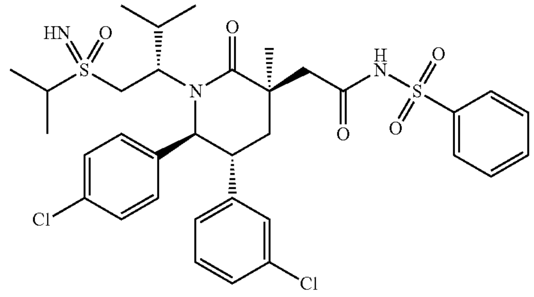 [SMILES: CC(C)[C@@H](CS(=N)(=O)C(C)C)N1C(=O)[C@@](C)(CC(=O)NS(=O)(=O)c2ccccc2)C[C@H](c2cccc(Cl)c2)[C@H]1c1ccc(Cl)cc1] | $^1$H NMR(400 MHz, $CD_3OD$) δ 8.08(d, J = 7.6 Hz, 2H), 7.73-7.67(m, 1H), 7.59(t, J = 7.7 Hz, 2H), 7.55-7.16(m, 4H), 7.13(d, J = 4.8 Hz, 2H), 7.02(s, 1H), 6.91(t, J = 4.6 Hz, 1H), 5.10(d, J = 11.1 Hz, 1H), 4.32(dd, J = 15.1, 10.3 Hz, 1H), 3.60-3.53(m, 1H), 3.51-3.43(m, 2H), 3.28(d, J = 15.3 Hz, 1H), 2.91(d, J = 14.1 Hz, 1H), 2.46(d, J = 14.3 Hz, 1H), 2.27-2.14(m, 2H), 1.87(d, J = 11.6 Hz, 1H), 1.49(dd, J = 6.5, 4.4 Hz, 6H), 1.27(s, 3H), 0.72(d, J = 6.4 Hz, 3H), 0.54(d, J = 6.7 Hz, 3H). LC-MS: M + 1 = 706.2 |
| 021 | 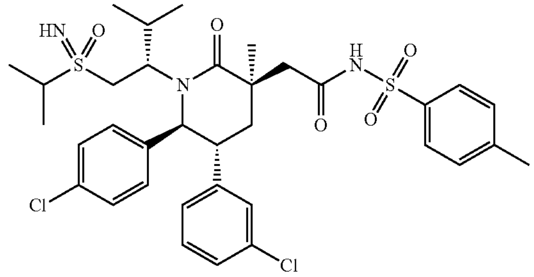 [SMILES: Cc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] | $^1$H NMR(400 MHz, $CD_3OD$) δ 7.94(d, J = 8.2 Hz, 2H), 7.74(s, 2H), 7.39(d, J = 7.9 Hz, 3H), 7.34-7.16(m, 2H), 7.13(d, J = 5.0 Hz, 2H), 7.00(s, 1H) 6 94-6.81(m, 1H), 5.06(d, J = 10.7 Hz, 1H), 4.49-4.24(m, 1H), 3.73-3.55(m, 1H), 3.54-3.37(m, 3H), 2.90(d, J = 14.2 Hz, 1H), 2.48(d, J = 6.4 Hz, 1H), 2.43(s, 3H), 2.20(t, J = 14.1 Hz, 2H), 1.84(d, J = 15.9 Hz, 1H), 1.50(dd, J = 6.5, 4.2 Hz, 6H), 1.28(s, 3H), 0.73(d, J = 6.4 Hz, 3H), 0.54(d, J = 6.7 Hz, 3H). LC-MS: M + 1 = 720.2 |
| 022 | 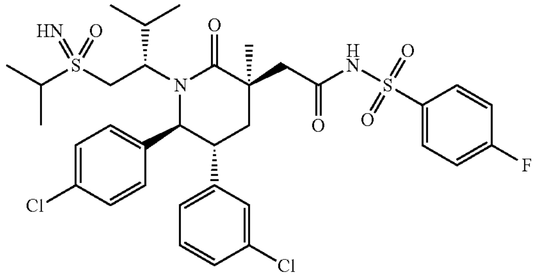 [SMILES: CC(C)[C@@H](CS(=N)(=O)C(C)C)N1C(=O)[C@@](C)(CC(=O)NS(=O)(=O)c2ccc(F)cc2)C[C@H](c2cccc(Cl)c2)[C@H]1c1ccc(Cl)cc1] | $^1$H NMR(400 MHz, $CD_3OD$) δ 8.12(dd, J = 8.9, 5.1 Hz, 2H), 7.55(d, J = 60.6 Hz, 4H), 7.31(t, J = 8.7 Hz, 2H), 7.12(d, J = 5.2 Hz, 2H), 7.06(s, 1H), 7.00-6.93(m, 1H), 5.31(d, J = 11.1 Hz, 1H), 3.98(dd, J = 13.8, 10.7 Hz, 1H), 3.52(t, J = 9.1 Hz, 1H), 3.48-3.38(m, 1H), 3.28-3.19(m, 1H), 3.04(d, J = 12.3 Hz, 1H), 2.89(d, J = 14.0 Hz, 1H), 2.46(d, J = 14.1 Hz, 1H), 2.28(t, J = 13.8 Hz, 1H), 2.16(dt, J = 14.3, 6.9 Hz, 1H), 1.83(dd, J = 13.8, 2.7 Hz, 1H), 1.41(t, J = 6.3 Hz, 6H), 1.27(s, 3H), 0.68(d, J = 6.6 Hz, 3H), 0.51(d, J = 6.9 Hz, 3H). LC-MS: M + 1 = 724.2 |
| 023 | 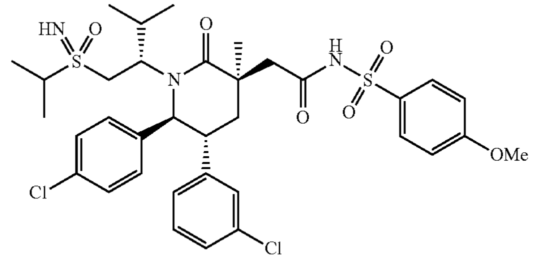 [SMILES: COc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] | $^1$H NMR(400 MHz, $CD_3OD$) δ 7.99(d, J = 8.9 Hz, 2H), 7.81-7.14(m, 4H), 7.11(d, J = 4.8 Hz, 2H), 7.06(d, J = 9.0 Hz, 3H), 6.90(t, J = 4.1 Hz, 1H), 5.29(d, J = 11.0 Hz, 1H), 3.97(dd, J = 13.8, 10.6 Hz, 1H), 3.87(s, 3H), 3.51(t, J = 9.0 Hz, 1H), 3.43-3.36(m, 1H), 3.24(dt, J = 13.6, 6.7 Hz, 1H), 3.03(d, J = 13.7 Hz, 1H), 2.89(d, J = 14.1 Hz, 1H), 2.43(d, J = 14.1 Hz, 1H), 2.25(t, J = 13.8 Hz, 1H), 2.20-2.09(m, 1H), 1.79(dd, J = 13.7, 2.6 Hz, 1H), 1.41(t, J = 6.3 Hz, 6H), 1.27(s, 3H), 0.68(d, J = 6.6 Hz, 3H), 0.52(d, J = 6.9 Hz, 3H). LC-MS: M + 1 = 736.2 |
| 024 | 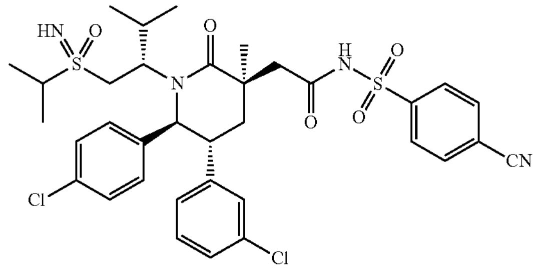 [SMILES: CC(C)[C@@H](CS(=N)(=O)C(C)C)N1C(=O)[C@@](C)(CC(=O)NS(=O)(=O)c2ccc(C#N)cc2)C[C@H](c2cccc(Cl)c2)[C@H]1c1ccc(Cl)cc1] | $^1$H NMR(400 MHz, $CD_3OD$) δ 8.23(d, J = 8.4 Hz, 2H), 7.97(d, J = 8.3 Hz, 2H), 7.66-7.18(m, 4H), 7.14(d, J = 4.7 Hz, 2H), 7.03(s, 1H), 6.98-6.89(m, 1H), 5.11(d, J = 11.4 Hz, 1H), 4.38-4.24(m, 1H), 3.62-3.52(m, 1H), 3.52-3.39(m, 3H), 3.27(d, J = 15.6 Hz, 1H), 2.90(d, J = 14.2 Hz, 1H), 2.50(d, J = 14.2 Hz, 1H), 2.25(t, J = 13.7 Hz, 1H), 2.20-2.09(m, 1H), 1.88(d, J = 12.7 Hz, 1H), 1.54-1.43(m, 6H), 1.29(s, 3H), 0.72(d, J = 6.3 Hz, 3H), 0.52(d, J = 6.8 Hz, 3H). LC-MS: M + 1 = 731.2 |

TABLE B-continued

| number | Structure | Analytical data |
|---|---|---|
| 025 | 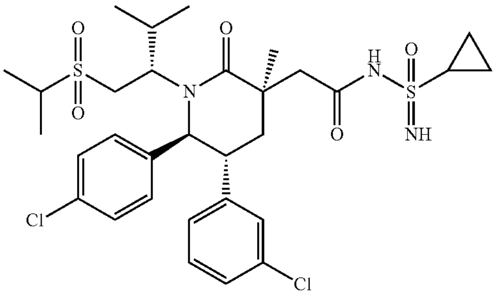 [SMILES: CC(C)[C@@H](CS(=O)(=O)C(C)C)N1C(=O)[C@@](C)(CC(=O)NS(=N)(=O)C2CC2)C[C@H](c2cccc(Cl)c2)[C@H]1c1ccc(Cl)cc1] | $^{1}$H NMR(400 MHz, $CD_3OD$) δ 7.29(br, 4H), 7.18-7.05(m, 4H), 5.13(d, J = 11.1 Hz, 1H), 4.09-3.97(m, 1H), 3.78-3.62(m, 1H), 3.30(m, 1H), 3.19-3.07(m, 1H), 3.00(dd, J = 12.8, 2.1 Hz, 1H), 2.97-2.91(m, 1H), 2.62-2.49(m, 1H), 2.33-2.08(m, 3H), 1.43(d, J = 6.8 Hz, 6H), 1.40(s, 3H), 1.29-0.95(m, 5H), 0.67(d, J = 6.6 Hz, 3H), 0.53(d, J = 6.9 Hz, 3H).<br>LC-MS: M + 1 = 670.2 |
| 028A | 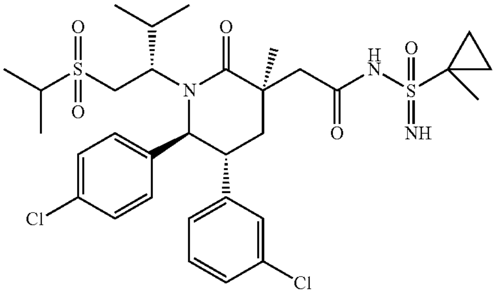 [SMILES: CC(C)[C@@H](CS(=O)(=O)C(C)C)N1C(=O)[C@@](C)(CC(=O)NS(=N)(=O)C2(C)CC2)C[C@H](c2cccc(Cl)c2)[C@H]1c1ccc(Cl)cc1] | $^{1}$H NMR(400 MHz, $CD_3OD$) δ 7.28(br, 3H),7.17-7.06(m, 5H), 5.11(d, J = 11.1 Hz, 1H), 4.03(dd, J = 13.7, 10.5 Hz, 1H), 3.73-3.64(m, 1H), 3.30(d, J = 7.3 Hz, 2H), 3.12(d, J = 13.8 Hz, 1H), 3.04(d, J = 12.9 Hz, 1H), 2.54(d, J = 12.9 Hz, 1H), 2.27(t, J = 13.4 Hz, 1H), 2.23-2.15(m, 2H), 1.55(s, 4H), 1.43(d, J = 6.9 Hz, 6H), 1.39(s, 3H), 1.00-0.84(m, 3H), 0.68(d, J = 6.6 Hz, 3H), 0.52(d, J = 6.9 Hz, 3H).<br>LC-MS: M + 1 = 684.2 |
| 028B | 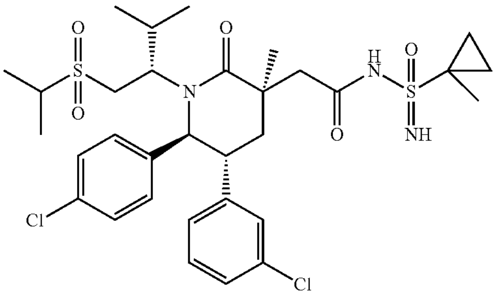 [SMILES: CC(C)[C@@H](CS(=O)(=O)C(C)C)N1C(=O)[C@@](C)(CC(=O)NS(=N)(=O)C2(C)CC2)C[C@H](c2cccc(Cl)c2)[C@H]1c1ccc(Cl)cc1] | $^{1}$H NMR(400 MHz, $CD_3OD$) δ 7.23(br, 4H), 7.16-7.12(m, 2H), 7.09(dd, J = 6.0, 4.5 Hz, 2H), 5.11(d, J = 11.1 Hz, 1H), 4.03(dd, J = 13.7, 10.6 Hz, 1H), 3.67(t, J = 10.7 Hz, 1H), 3.30(d, J = 4.0 Hz, 2H), 3.11(d, J = 13.7 Hz, 1H), 3.01(d, J = 12.8 Hz, 1H), 2.52(d, J = 12.8 Hz, 1H), 2.30(d, J = 13.5 Hz, 1H), 2.26-2.20(m, 1H), 2.16(dd, J = 13.5, 3.2 Hz, 1H), 1.54(s, 3H), 1.53-1.48(m, 1H), 1.43(d, J = 6.8 Hz, 7H), 1.38(s, 3H), 0.97-0.83(m, 3H), 0.68(d, J = 6.6 Hz, 3H), 0.54(d, J = 6.9 Hz, 3H).<br>LC-MS: M + 1 = 684.2 |
| 029 | 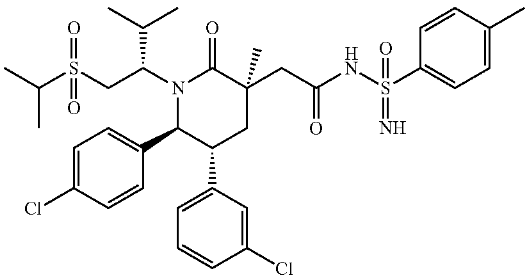 [SMILES: Cc1ccc(S(=N)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1] | $^{1}$H NMR(400 MHz, $CD_3OD$) δ 7.74(br, 1H), 7.60(d, J = 8.3 Hz, 2H), 7.33(br, 3H), 7.15(d, J = 6.5 Hz, 2H), 7.09(d, J = 8.0 Hz, 2H), 7.01(s, 1H), 6.94(d, J = 7.3 Hz, 1H), 5.03(d, J = 11.2 Hz, 1H), 4.04-3.93(m, 1H), 3.63-3.52(m, 1H), 3.31-3.25(m, 2H), 3.09(dd, J = 13.7, 1.8 Hz, 1H), 3.00(d, J = 13.0 Hz, 1H), 2.52(d, J = 12.9 Hz, 1H), 2.33(s, 3H), 2.18-2.08(m, 1H), 2.01(t, J = 13.5 Hz, 1H), 1.74(dd, J = 13.7, 2.8 Hz, 1H), 1.41(d, J = 6.9 Hz, 6H), 1.23(s, 3H), 0.65(d, J = 6.6 Hz, 3H), 0.46(d, J = 6.9 Hz, 3H).<br>LC-MS: M + 1 = 720.2 |
| 034 | 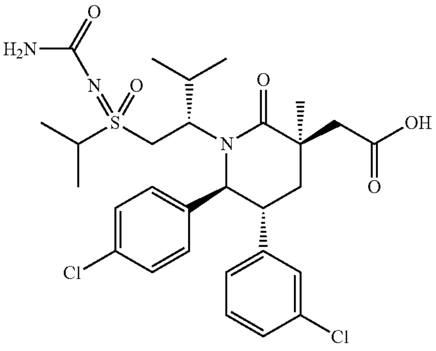 | $^{1}$H NMR(400 MHz, $CD_3OD$) δ 7.95-6.95(m, 10H), 5.22(d, J = 11.1 Hz, 1H), 4.25(dd, J = 13.8, 10.4 Hz, 1H), 4.05(p, J = 6.9 Hz, 1H), 3.62-3.52(m, 1H), 3.51-3.40(m, 2H), 3.00(d, J = 13.5 Hz, 1H), 2.63(d, J = 13.6 Hz, 1H), 2.34(t, J = 13.7 Hz, 1H), 2.15(dt, J = 14.1, 7.0 Hz, 1H), 2.05(dd, J = 13.6, 2.9 Hz, 1H), 1.48(t, J = 7.1 Hz, 6H), 1.39(s, 3H), 0.68(d, J = 6.6 Hz, 3H), 0.50(d, J = 6.9 Hz, 3H).<br>LC-MS: M + 1 = 610.2 |

TABLE B-continued

| number | Structure | Analytical data |
|---|---|---|
| 035 | 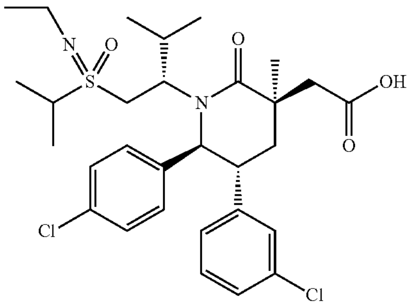 [SMILES: CCN=S(=O)(C[C@H](C(C)C)N1C(=O)[C@@](C)(CC(=O)O)C[C@H](c2cccc(Cl)c2)[C@H]1c1ccc(Cl)cc1)C(C)C] | $^1$H NMR(400 MHz, $CD_3OD$) δ 7.52-6.81(m, 8H), 5.22(d, J = 11.0 Hz, 1H), 4.01(dd, J = 13.9, 10.7 Hz, 1H), 3.61-3.47(m, 2H), 3.47-3.35(m, 2H), 3.29-3.17(m, 1H), 3.06(dd, J = 14.0, 1.9 Hz, 1H), 2.99(d, J = 13.4 Hz, 1H), 2.65(d, J = 13.5 Hz, 1H), 2.46(t, J = 13.7 Hz, 1H), 2.16(dq, J = 14.0, 6.9 Hz, 1H), 2.03(dd, J = 13.5, 3.1 Hz, 1H), 1.48(d, J = 6.9 Hz, 3H), 1.43(d, J = 7.0 Hz, 3H), 1.40(s, 3H), 1.31(t, J = 7.2 Hz, 3H), 0.69(d, J = 6.7 Hz, 3H), 0.47(d, J = 7.0 Hz, 3H). LC-MS: M + 1 = 595.2 |
| 039 | 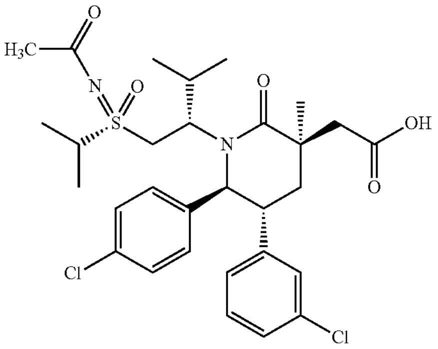 [SMILES: CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] | $^1$H NMR(400 MHz, $CD_3OD$) δ 7.51-6.97(m, 8H), 5.13(d, J = 11.0 Hz, 1H), 4.35(dd, J = 14.1, 10.4 Hz, 1H), 4.08(p, J = 7.0 Hz, 1H), 3.61-3.52(m, 2H), 3.32-3.29(m, 1H), 3.00(d, J = 12.9 Hz, 1H), 2.63(d, J = 12.2 Hz, 1H), 2.30(t, J = 13.7 Hz, 1H), 2.19-2.05(m, 2H), 2.13(s, 3H), 1.51(d, J = 6.8 Hz, 3H), 1.46(d, J = 6.9 Hz, 3H), 1.39(s, 3H), 0.67(d, J = 6.6 Hz, 3H), 0.51(d, J = 6.9 Hz, 3H). LC-MS: M + 1 = 609.2 |
| 041 | 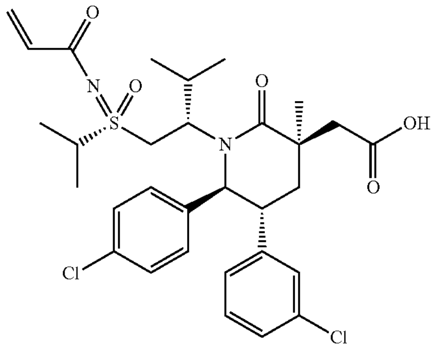 [SMILES: C=CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] | $^1$H NMR(400 MHz, $CD_3OD$) δ 7.50-6.98(m, 8H), 6.41-6.27(m, 2H), 5.85(dd, J = 9.4, 2.6 Hz, 1H), 5.14(d, J = 11.0 Hz, 1H), 4.39(dd, J = 14.0, 10.4 Hz, 1H), 4.11(p, J = 6.8 Hz, 1H), 3.64(dd, J = 13.9, 1.7 Hz, 1H), 3.55(ddd, J = 13.9, 10.8, 3.0 Hz, 1H), 3.31-3.27(m, 1H), 3.00(d, J = 13.6 Hz, 1H), 2.64(d, J = 13.6 Hz, 1H), 2.33(t, J = 13.7 Hz, 1H), 2.19-2.11(m, 1H), 2.07(dd, J = 13.7, 3.1 Hz, 1H), 1.53(d, J = 6.8 Hz, 3H), 1.46(d, J = 6.9 Hz, 3H), 1.39(s, 3H), 0.67(d, J = 6.6 Hz, 3H), 0.48(d, J = 6.9 Hz, 3H). LC-MS: M + 1 = 621.2 |
| 042 | 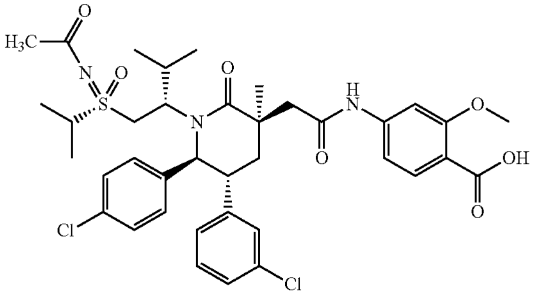 [SMILES: COc1cc(NC(=O)C[C@@]2(C)C[C@H](c3cccc(Cl)c3)[C@@H](c3ccc(Cl)cc3)N([C@H](C[S@](=O)(=NC(C)=O)C(C)C)C(C)C)C2=O)ccc1C(=O)O] | $^1$H NMR(400 MHz, $CD_3OD$) δ 7.91(d, J = 8.5 Hz, 1H), 7.72(s, 1H), 7.26(d, J = 8.6 Hz, 4H), 7.10(d, J = 6.5 Hz, 3H), 6.90(d, J = 8.2 Hz, 2H), 5.11(d, J = 10.9 Hz, 1H), 3.95(s, 3H), 3.08(d, J = 13.4 Hz, 1H), 2.65(d, J = 13.4 Hz, 1H), 2.33(t, J = 13.8 Hz, 2H), 2.20-2.15(m, 2H), 2.13(s, 3H), 1.51(d, J = 6.8 Hz, 3H), 1.46(d, J = 6.9 Hz, 3H), 1.41(s, 3H), 0.70(d, J = 6.6 Hz, 3H), 0.56(d, J = 6.9 Hz, 3H). LC-MS: M + 1 = 758.2 |

TABLE B-continued
| number | Structure | Analytical data |
|---|---|---|
| 043 | 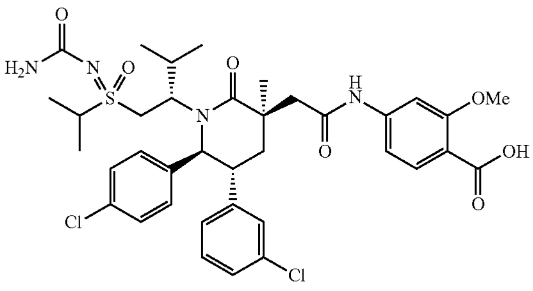 [SMILES: COc1cc(NC(=O)C[C@@]2(C)C[C@H](c3cccc(Cl)c3)[C@@H](c3ccc(Cl)cc3)N([C@H](CS(=O)(=NC(N)=O)C(C)C)C(C)C)C2=O)ccc1C(=O)O] | LC-MS: M + 1 = 759.2 |
| 045 | 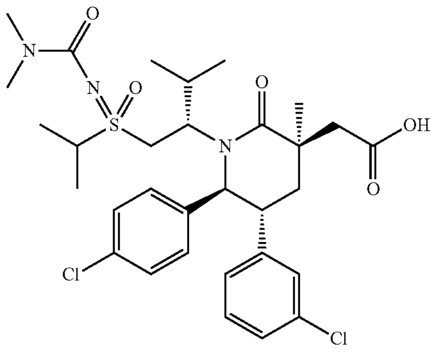 [SMILES: CC(C)[C@@H](CS(=O)(=NC(=O)N(C)C)C(C)C)N1C(=O)[C@@](C)(CC(=O)O)C[C@H](c2cccc(Cl)c2)[C@H]1c1ccc(Cl)cc1] | LC-MS: M + 1 = 638.0 |
| 046 | 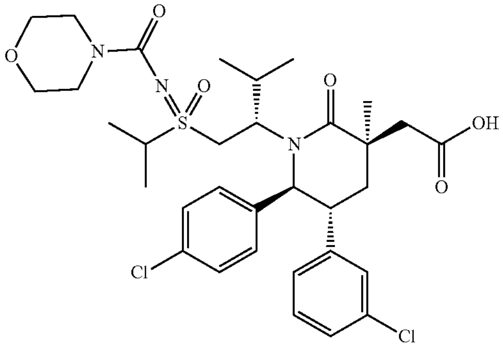 [SMILES: CC(C)[C@@H](CS(=O)(=NC(=O)N1CCOCC1)C(C)C)N1C(=O)[C@@](C)(CC(=O)O)C[C@H](c2cccc(Cl)c2)[C@H]1c1ccc(Cl)cc1] | LC-MS: M + 1 = 680.2 |
| 047 | 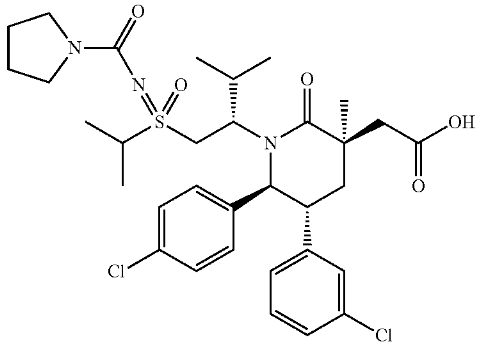 [SMILES: CC(C)[C@@H](CS(=O)(=NC(=O)N1CCCC1)C(C)C)N1C(=O)[C@@](C)(CC(=O)O)C[C@H](c2cccc(Cl)c2)[C@H]1c1ccc(Cl)cc1] | LC-MS: M + 1 = 664.2 |

TABLE B-continued
| num-ber | Structure | Analytical data |
|---|---|---|
| 048 | 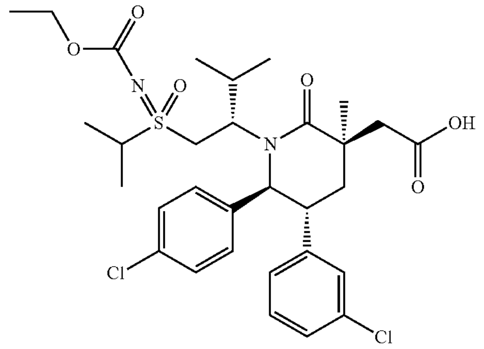 [SMILES: CCOC(=O)N=S(=O)(C[C@H](C(C)C)N1C(=O)[C@@](C)(CC(=O)O)C[C@H](c2cccc(Cl)c2)[C@H]1c1ccc(Cl)cc1)C(C)C] | LC-MS: M + 1 = 639.2 |
| 049 | 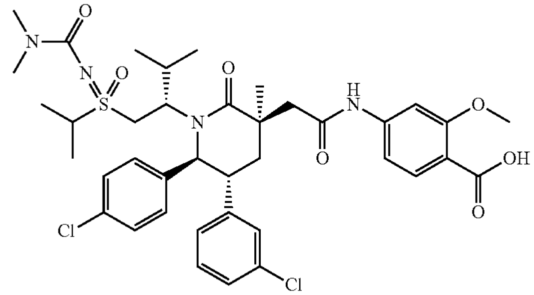 | LC-MS: M + 1 = 787.2 |
| 050 | 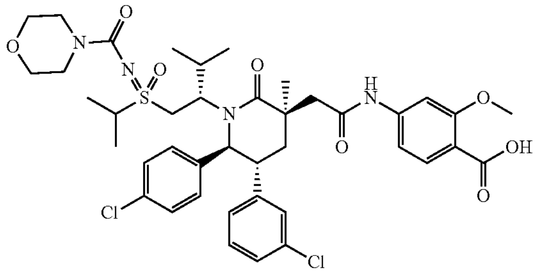 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCOCC3)C(C)C)C(C)C)C2=O)ccc1C(=O)O] | LC-MS: M + 1 = 829.3 |
| 051 | 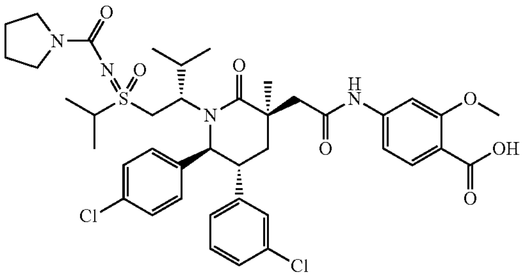 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCCC3)C(C)C)C(C)C)C2=O)ccc1C(=O)O] | LC-MS: M + 1 = 813.2 |
| 052 | 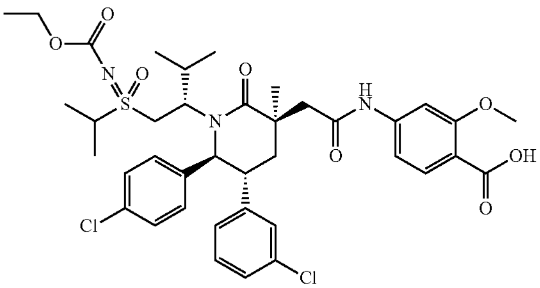 [SMILES: CCOC(=O)N=S(=O)(C[C@H](C(C)C)N1C(=O)[C@@](C)(CC(=O)Nc2ccc(C(=O)O)c(OC)c2)C[C@H](c2cccc(Cl)c2)[C@H]1c1ccc(Cl)cc1)C(C)C] | LC-MS: M + 1 = 788.2 |

TABLE B-continued

| num-ber | Structure | Analytical data |
|---|---|---|
| 053 | 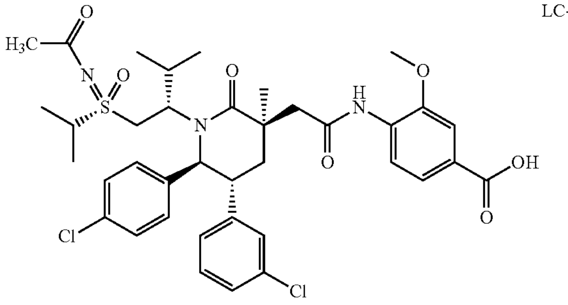 | LC-MS: M + 1 = 758.2 |
| 054 | 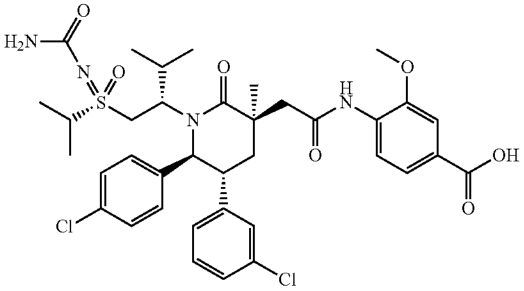 [SMILES: COc1cc(C(=O)O)ccc1NC(=O)C[C@@]1(C)C[C@H](c2cccc(Cl)c2)[C@@H](c2ccc(Cl)cc2)N([C@H](C[S@](=O)(=NC(N)=O)C(C)C)C(C)C)C1=O] | $^1H$ NMR(400 MHz, DMSO-$d_6$) δ 12.82(s, 1H), 9.61(s, 1H), 8.27(d, J = 8.2 Hz, 1H), 7.58(dd, J = 8.4, 1.8 Hz, 1H), 7.52(d, J = 1.8 Hz, 1H), 7.50-7.06(m, 6H), 6.96(d, J = 7.5 Hz, 1H), 6.84(s, 1H), 5.13(d, J = 11.1 Hz, 1H), 4.08(dd, J = 14.0, 10.3 Hz, 1H), 3.94(q, J = 7.0 Hz, 1H), 3.87(s, 3H), 3.57(t, J = 12.8 Hz, 1H), 3.47(d, J = 13.4 Hz, 1H), 3.22(t, J = 9.6 Hz, 1H), 3.11(d, J = 13.5 Hz, 1H), 2.84(d, J = 13.3 Hz, 1H), 2.18-1.98(m, 4H), 1.37(d, J = 6.7 Hz, 3H), 1.33(d, J = 6.9 Hz, 2H), 1.29(s, 2H), 0.55(d, J = 6.5 Hz, 3H), 0.41(d, J = 6.9 Hz, 3H). LC-MS: M + 1 = 759.2 |

Biological Example 1: Homogeneous Time Resolved Fluorometry (Htrf Assay)

The standard conditions for in vitro HTRF determination were as follows: 1 mM DTT, 0.1% BSA, 2.5 nM GST-hMDM2 (aa1-188), 5 nM biotinylated-p53 (aa1-83), 1.8 nM SA-XLent (cisbio; Bedford, Mass.), 0.6 nM anti GST cryptate monoclonal antibody (cisbio; Bedford, Mass.) and 200 mM KF in 1×PBS buffer (pH=7.4) was added in black 384-well costar polypropylene plate, of which the total volume was 50 uL. The amino acid residues 1-188 of human MDM2 were expressed as GST-hMDM2 fusion protein in *E. coli*. Residues 1-83 of human p53 were expressed as avitag <TM>-trxa-6×his fusion protein (biotinlabelled p53) in *E. coli*. Each protein was separated from cell homogenate by affinity chromatography.

Specifically, 10 μL GST-hMDM2 was incubated with 10 uL diluted compound in 10% DMSO for 20 minutes at room temperature. 20 μL biotinlabelled-p53 was added to the mixture of GST-hMDM2 and then incubated at room temperature for 60 min. A 10 μL detection buffer consisting of SA-XLent, anti-GST cavernous compound antibody and KF was added to the reaction solution consisting of GST-hMDM2, biotinlabelled-p53 and the compound and was placed at room temperature to achieve equilibrium and maintained for more than 4 h. The final concentration of DMSO in the reaction solution was 2%. Time resolved fluorescence were measured on a microplate multi label reader. The inhibition percentage was calculated relative to nutlin-3.

When the potency of MDM2 inhibitor increased, an improved HTRF assay (HTRF2 assay) was performed. Except for the changes of following reagent concentration, all the measuring conditions were the same as above: 0.2 nM GST-hMDM2(1-188), 0.5 nM biotinlabelled-p53 (1-83), 0.18 nM SA-XLent, and 100 mm KF.

Results are listed in the following table 1, whererin, + represents $<10$ nm; ++ represents 10-100 nm; +++ represents $>100$ nm.

TABLE 1

| HTRF analysis | |
|---|---|
| number | $IC_{50}$ nM |
| 001 | + |
| 002 | + |
| 003 | + |
| 006 | + |
| 007 | + |
| 008 | + |
| 009 | + |
| 010 | ++ |
| 011 | ++ |
| 012 | +++ |
| 013 | +++ |
| 014 | +++ |
| 015 | ++ |
| 016 | +++ |
| 017 | +++ |
| 018 | ++ |
| 019 | ++ |
| 020 | ++ |
| 021 | ++ |
| 022 | ++ |
| 023 | ++ |
| 024 | ++ |
| 025 | ++ |
| 028A | ++ |
| 028B | ++ |
| 029 | +++ |
| 034 | + |
| 035 | + |
| 039 | + |
| 041 | ++ |
| 042 | + |
| 043 | + |
| 045 | + |
| 046 | + |

TABLE 1-continued

| HTRF analysis | |
|---|---|
| number | $IC_{50}$ nM |
| 047 | + |
| 048 | + |
| 049 | + |
| 050 | + |
| 051 | + |
| 052 | + |
| 053 | + |
| 054 | + |

Biological Example 2: P21 Assay

Inhibition of the interaction between hMDM2 and p53 results in the activation of the p53 pathway via the stabilization and accumulation of p53. P53 activates the transcription of many genes, one of which is p21<WAFT/CIP1>. To evaluate the potency of hMDM2 inhibitors, quantitative reverse transcription polymerase chain reaction (QRT PCR) was used to measure the level of p21 transcripts of compound related cells relative to that of control cells treated with dimethyl sulfoxide (DMSO).

In the first day, SJSA-1 cells were inoculated into 100 μL growth medium (RPMI1640; 10 mM HEPES; 1 mM sodium pyruvate; 1× penicillin streptomycin glutamine (PSQ) and 10% FBS, all reagents were obtained from Invitrogen) at a density of $3\times10^4$ cells in 96-well cell culture plate. The cells were cultured overnight at 37° C. and 5% $CO_2$ atmosphere.

In the second day, hMDM2 inhibitor was gradient diluted in DMSO(Sigma-Aldrich; St. Louis, Mo.). 5 μl of each compound dilution were added into 245 μl filtered assay medium (RPMI1640, 10% FBS, 10 mM HEPES, 1 mM sodium pyruvate and 1×PSQ). Or the assay was conducted with the presence of 10% human serum or 10% mouse serum, or without serum. Growth medium was removed from inoculated SJSA-1 cell culture plate and replaced by 100 μL assay medium for each well. Then 100 μL culture medium containing diluted inhibitor was added into each well to a final volume 200 μL. The final concentration of the compound was in the range of 0.049 μm-50 μm by dose titration with DMSO as control. The cells were incubated at 37° C. and 5% $CO_2$ for 7 hours with the presence of inhibitor. When incubation was completed, growth medium was removed from cells and the plate was stored at −80° C.

In the third day, giagen BioRobot Universal workstation was used to purify total RNA from SJSA-1 cells treated with inhibitor and DMSO respectively. The purification procedure herein was according to RNeasy96BioRobot8000 test kit provided by Qiagen, Valencia, Calif.

To measure the level of existing p21 transcripts, QRT-PCR was introduced. The levels of p21, housekeeping genes and glyceraldehyde 3-phosphate dehydrogenase (GAPDH) were determined by the total RNA from each inhibitor- or DMSO-treated well by duplicated test. The QRT-PCR reaction was performed on the Applied Biosystems prism 7900ht instrument using the relative quantitative (ΔΔ Ct) method according to the following cycle conditions: 48° C. for 30 minutes, then 95° C. for 10 minutes, and then was 40 cycles consisting of 95° C. for 15 seconds and 60° C. for 1 minute. The data were analyzed by using Applied Biosystems SDS2.2 software, with GAPDH as inner control and DMSO treated samples as calibrators. SDS2.2 software calculated the relative quantification (RQ) or increased fold of p21 level relative to DMSO control for each treated sample. The maximum (100%) p21 induction fold was defined by the maximum value of the fitting curve of the reference compound. The p21 induction fold of each inhibitor dose tested was converted to a value representing the percentage of the maximum value. XLFit software (ID business solutions, Alameda, Calif.) was used to make dose-response curve to calculate the $IC_{50}$ transit value of each inhibitor tested.

Results are listed in the following table 2, whererin, + represents <1 μM; ++ represents 1-10 μM; +++ represents >10 μM.

TABLE 2

| cell assay (SJSA-1 cell) | |
|---|---|
| number | $IC_{50}$(μM) |
| 001 | + |
| 002 | + |
| 003 | + |
| 006 | + |
| 007 | ++ |
| 008 | + |
| 009 | ++ |
| 010 | ++ |
| 011 | ++ |
| 012 | ++ |
| 013 | ++ |
| 014 | ++ |
| 015 | ++ |
| 016 | ++ |
| 017 | ++ |
| 018 | ++ |
| 019 | ++ |
| 020 | ++ |
| 021 | ++ |
| 022 | ++ |
| 023 | + |
| 024 | ++ |
| 025 | ++ |
| 028A | + |
| 028B | ++ |
| 029 | ++ |
| 034 | + |
| 035 | + |
| 039 | + |
| 041 | + |
| 042 | + |
| 043 | + |
| 045 | + |
| 046 | + |
| 047 | + |
| 048 | + |
| 049 | + |
| 050 | + |
| 051 | + |
| 052 | + |
| 053 | + |
| 054 | + |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound according to Formula I:

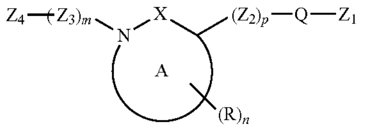

I or stereoisomers or tautomers thereof, or pharmaceutically acceptable salts, hydrates or solvates thereof, wherein,

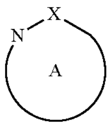

is selected from the group consisting of 5, 6 or 7 membered heterocyclic with 1-3 N and 0-2 heteroatoms selected from S and O;

X is independently C═O or S═(O)$_2$;

n is 1, 2, 3 or 4;

each R is selected independently from the group consisting of H, Cyano, halogen, substituted or unsubstituted $C_1$-$C_6$ alkyl, substituted or unsubstituted $C_1$-$C_6$ alkoxy, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O;

$Z_1$ is selected from the group consisting of H, substituted or unsubstituted $C_1$-$C_6$ alkyl, substituted or unsubstituted $C_1$-$C_6$ alkoxy, substituted or unsubstituted $C_3$-$C_8$ cycloalkyl(including single, fused or bridged ring form), substituted or unsubstituted $C_6$-$C_{10}$ aryl;

Q is selected from the group consisting of

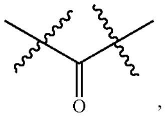

,

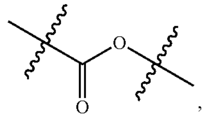

,

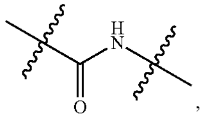

,

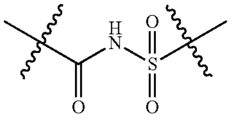

or

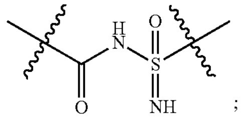

;

M and p are selected independently from the group consisting of 1, 2, 3 or 4;

Each $Z_2$ and $Z_3$ is selected independently from the group consisting of none, substituted or unsubstituted $C_1$-$C_7$ alkylidene, $NR_1$, O, S, C═O, S═(O)$_2$;

$Z_4$ is selected

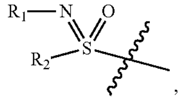

,

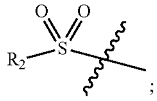

;

wherein, $R_1$ is selected from the group consisting of H, substituted or unsubstituted $C_1$-$C_6$ alkyl, substituted or unsubstituted $C_6$-$C_{10}$ aryl, CN, —C(═O)—NRdRe, —C(═O)-substituted or unsubstituted $C_1$-$C_6$ alkoxy, —C(═O)-substituted or unsubstituted $C_1$-$C_6$ alkyl, —C(═O)-substituted or unsubstituted $C_3$-$C_{10}$ cycloalkyl, —C(═O)-substituted or unsubstituted $C_2$-$C_6$ alkenyl, —C(═O)-substituted or unsubstituted $C_2$-$C_6$ alkynyl;

Rd and Re are selected independently from the group consisting of H, substituted or unsubstituted $C_1$-$C_6$ alkyl, substituted or unsubstituted $C_3$-$C_{10}$ cycloalkyl, substituted or unsubstituted $C_6$-$C_{10}$ aryl; the Rd and Re herein form a 4-10 membered heterocyclic with adjacent N, and the heterocyclic contains 1-2 N and 0-2 S or O;

$R_2$ is selected from the group consisting of substituted or unsubstituted $C_1$-$C_6$ alkyl, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, S and O;

Unless otherwise specified, "substituted" refers to being substituted by one or more (for example, 2, 3, 4, etc.) substituents selected from the group consisting of halogen, $C_1$-$C_6$ alkyl, halogenated $C_1$-$C_6$ alkyl, $C_1$-$C_6$ alkoxy, halogenated $C_1$-$C_6$ alkoxy, $C_3$-$C_8$ cycloalkyl, halogenated $C_3$-$C_8$ cycloalkyl, oxo, —CN, hydroxy, —$NH_2$, carboxy, unsubstituted or substituted group selected from the group consisting of $C_6$-$C_{10}$ aryl, halogenated $C_6$-$C_{10}$ aryl, 5-10 membered heteroaryl with 1-3 heteroatoms selected from N, S and O; halogenated 5-10 membered heteroaryl with 1-3 heteroatoms selected from N, S and O; and the substituted is substituted by substituents selected from the group consisting of halogen, $C_1$-$C_6$ alkoxy;

with the proviso that when $Z_4$ is

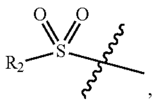

,

R, then Q is

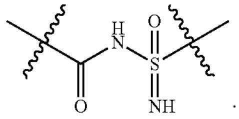 [SMILES: *C(=O)NS(*)(=N)=O]

.

2. The compound of claim 1, stereoisomers or tautomers thereof, or pharmaceutically acceptable salts, hydrates or solvates thereof, wherein the compound has a structure according to Formula II:

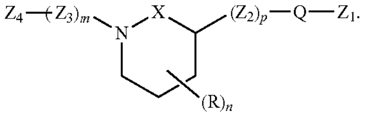

II

3. The compound of claim 1, wherein the compound has a structure according to Formula III:

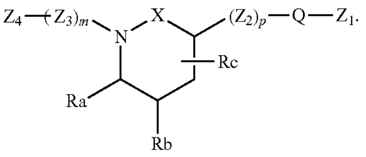

III wherein, Ra and Rb are independently selected from substituted or unsubstituted $C_6$-$C_{10}$ aryl and 5-10 membered heteroaryl with 1-3 heteroatoms selected from N, S and O;

Re is selected from the group consisting of H, CN, halogen, substituted or unsubstituted $C_1$-$C_6$ alkyl, substituted or unsubstituted $C_1$-$C_6$ alkoxy;

the remaining groups are defined as in claim 1.

4. The compound of claim 1, wherein the compound has a structure according to formula IV:

IV

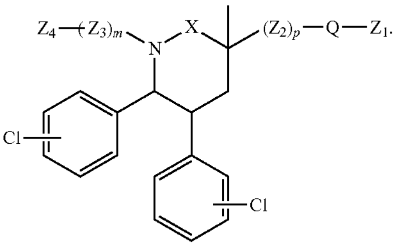

5. The compound of claim 1, wherein the compound has a structure selected from the following table:

| number | structure |
|---|---|
| 001 | 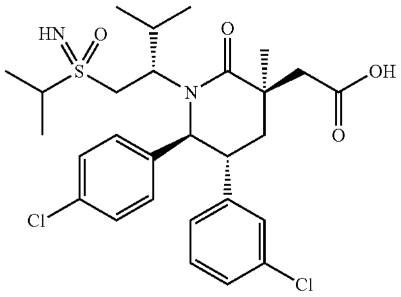 isomer with high TLC polarity |
| 002 | 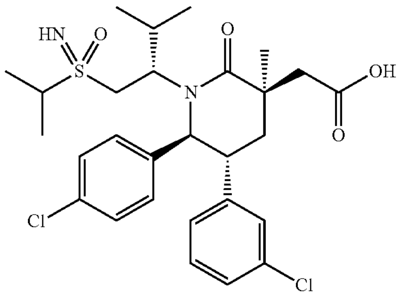 isomer with low TLC polarity |
| 003 | 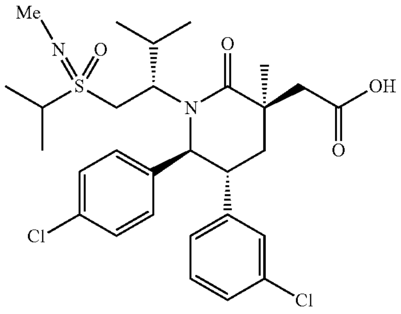 isomer with low TLC polarity |

-continued
| number | structure |
|---|---|
| 004 | 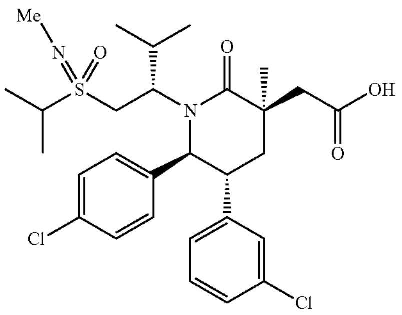<br>isomer with high TLC polarity |
| 005 | 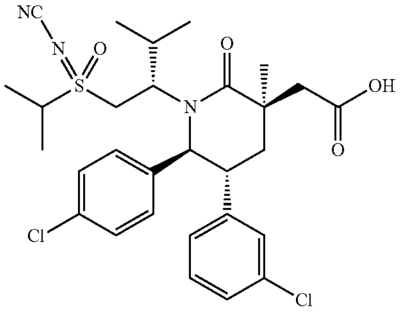<br>peak 1 isomer in HPLC |
| 006 | 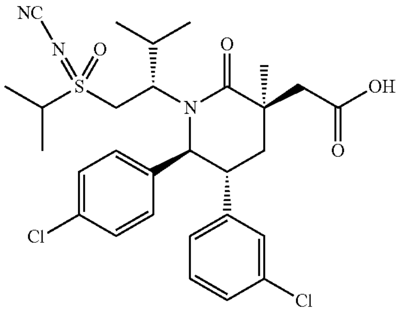<br>peak 2 isomer in HPLC |
| 007 | 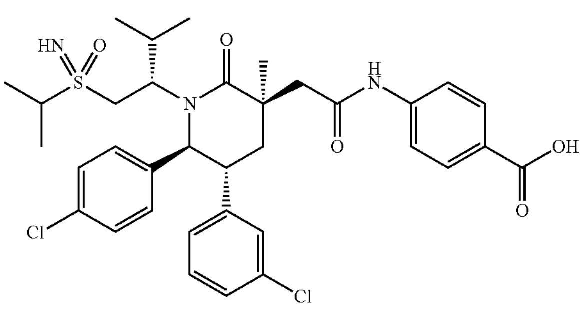 [SMILES: CC(C)[C@@H](CS(=N)(=O)C(C)C)N1C(=O)[C@@](C)(CC(=O)Nc2ccc(C(=O)O)cc2)C[C@H](c2cccc(Cl)c2)[C@H]1c1ccc(Cl)cc1] |

-continued
| number | structure |
|---|---|
| 008 | 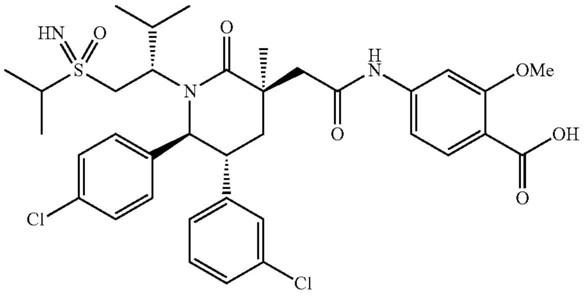 [SMILES: COc1cc(NC(=O)C[C@@]2(C)C[C@H](c3cccc(Cl)c3)[C@@H](c3ccc(Cl)cc3)N([C@H](CS(=N)(=O)C(C)C)C(C)C)C2=O)ccc1C(=O)O] |
| 009 | 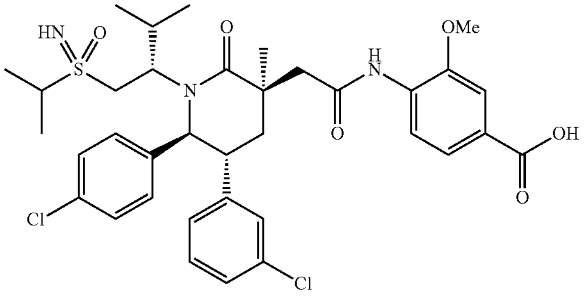 [SMILES: COc1cc(C(=O)O)ccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] |
| 010 | 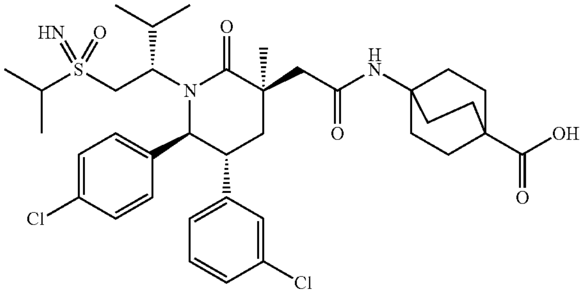 [SMILES: CC(C)[C@@H](CS(=N)(=O)C(C)C)N1C(=O)[C@@](C)(CC(=O)NC23CCC(C(=O)O)(CC2)CC3)C[C@H](c2cccc(Cl)c2)[C@H]1c1ccc(Cl)cc1] |
| 011 | 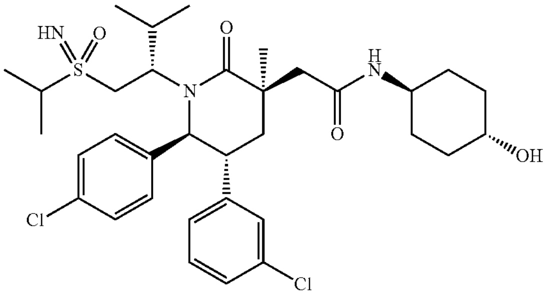 [SMILES: CC(C)[C@@H](CS(=N)(=O)C(C)C)N1C(=O)[C@@](C)(CC(=O)N[C@H]2CC[C@H](O)CC2)C[C@H](c2cccc(Cl)c2)[C@H]1c1ccc(Cl)cc1] |
| 012 | 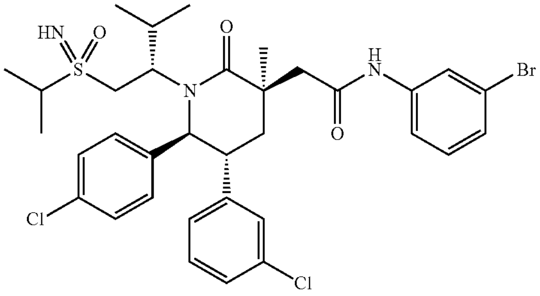 [SMILES: CC(C)[C@@H](CS(=N)(=O)C(C)C)N1C(=O)[C@@](C)(CC(=O)Nc2cccc(Br)c2)C[C@H](c2cccc(Cl)c2)[C@H]1c1ccc(Cl)cc1] |

-continued
| number | structure |
| --- | --- |
| 013 | 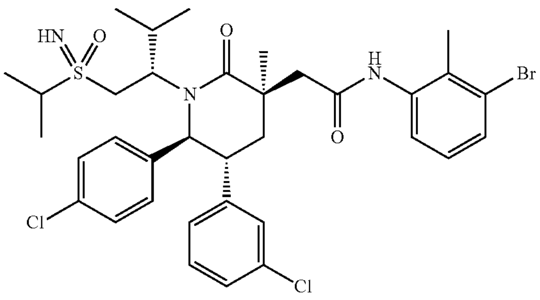 [SMILES: Cc1c(Br)cccc1NC(=O)C[C@@]1(C)C[C@H](c2cccc(Cl)c2)[C@@H](c2ccc(Cl)cc2)N([C@H](CS(=N)(=O)C(C)C)C(C)C)C1=O] |
| 014 | 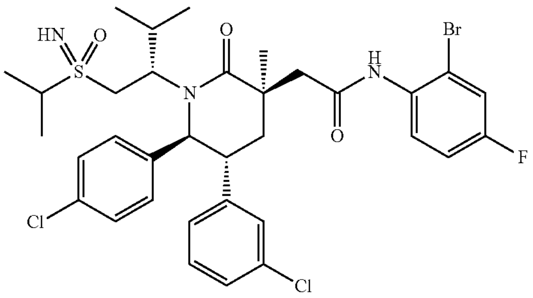 [SMILES: CC(C)[C@@H](CS(=N)(=O)C(C)C)N1C(=O)[C@@](C)(CC(=O)Nc2ccc(F)cc2Br)C[C@H](c2cccc(Cl)c2)[C@H]1c1ccc(Cl)cc1] |
| 015 | 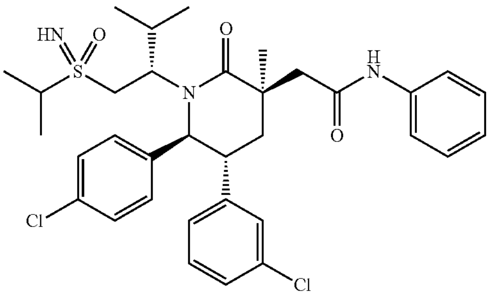 [SMILES: CC(C)[C@@H](CS(=N)(=O)C(C)C)N1C(=O)[C@@](C)(CC(=O)Nc2ccccc2)C[C@H](c2cccc(Cl)c2)[C@H]1c1ccc(Cl)cc1] |
| 016 | 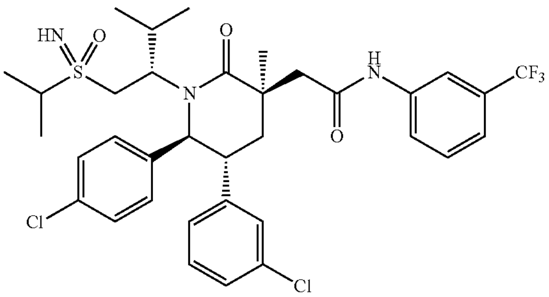 [SMILES: CC(C)[C@@H](CS(=N)(=O)C(C)C)N1C(=O)[C@@](C)(CC(=O)Nc2cccc(C(F)(F)F)c2)C[C@H](c2cccc(Cl)c2)[C@H]1c1ccc(Cl)cc1] |
| 017 | 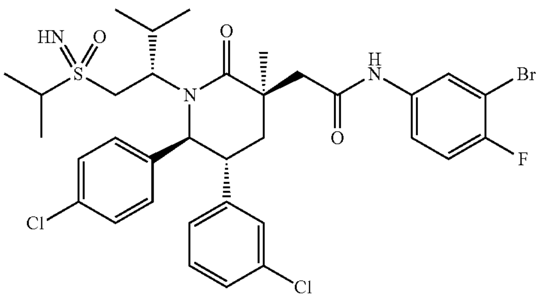 [SMILES: CC(C)[C@@H](CS(=N)(=O)C(C)C)N1C(=O)[C@@](C)(CC(=O)Nc2ccc(F)c(Br)c2)C[C@H](c2cccc(Cl)c2)[C@H]1c1ccc(Cl)cc1] |

-continued
| number | structure |
|---|---|
| 018 | 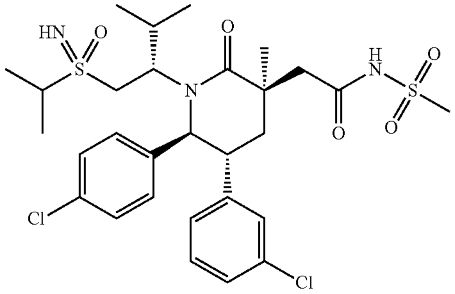<br>R configuration and S configuration |
| 019 | 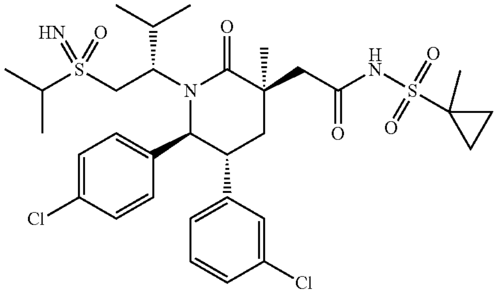<br>R configuration and S configuration |
| 020 | 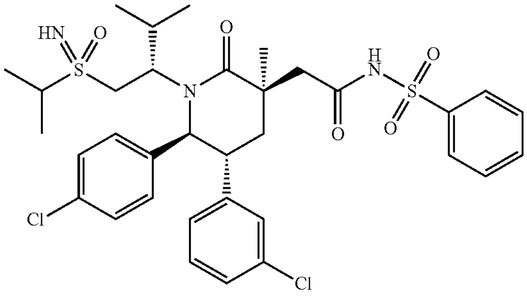 [SMILES: CC(C)[C@@H](CS(=N)(=O)C(C)C)N1C(=O)[C@@](C)(CC(=O)NS(=O)(=O)c2ccccc2)C[C@H](c2cccc(Cl)c2)[C@H]1c1ccc(Cl)cc1] |
| 021 | 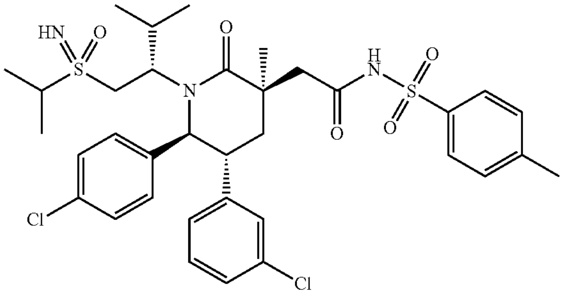 [SMILES: Cc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] |
| 022 | 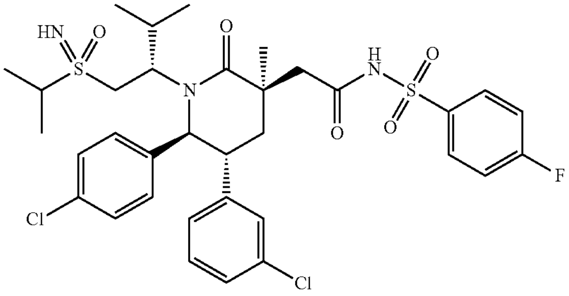 [SMILES: CC(C)[C@@H](CS(=N)(=O)C(C)C)N1C(=O)[C@@](C)(CC(=O)NS(=O)(=O)c2ccc(F)cc2)C[C@H](c2cccc(Cl)c2)[C@H]1c1ccc(Cl)cc1] |

-continued
| number | structure |
|---|---|
| 023 | 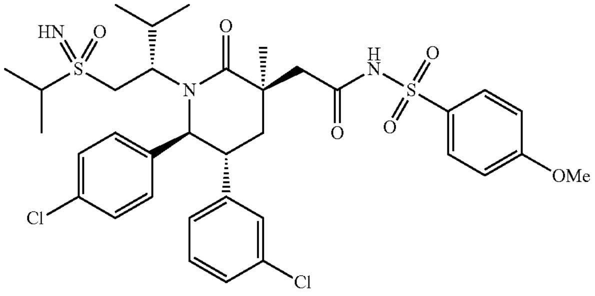 [SMILES: COc1ccc(S(=O)(=O)NC(=O)C[C@@]2(C)C[C@H](c3cccc(Cl)c3)[C@@H](c3ccc(Cl)cc3)N([C@H](CS(=N)(=O)C(C)C)C(C)C)C2=O)cc1] |
| 024 | 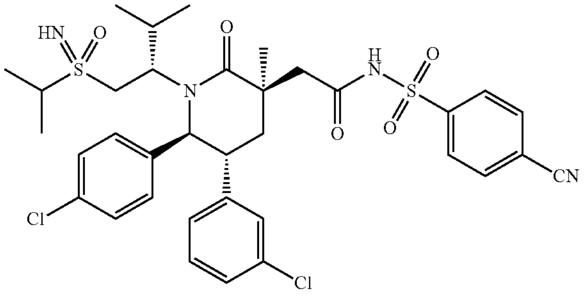 [SMILES: CC(C)[C@@H](CS(=N)(=O)C(C)C)N1C(=O)[C@@](C)(CC(=O)NS(=O)(=O)c2ccc(C#N)cc2)C[C@H](c2cccc(Cl)c2)[C@H]1c1ccc(Cl)cc1] |
| 025 | 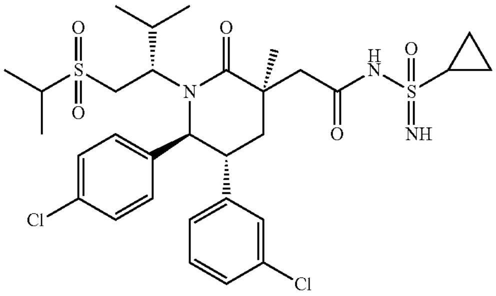 [SMILES: CC(C)[C@@H](CS(=O)(=O)C(C)C)N1C(=O)[C@@](C)(CC(=O)NS(=N)(=O)C2CC2)C[C@H](c2cccc(Cl)c2)[C@H]1c1ccc(Cl)cc1] |
| 028A | 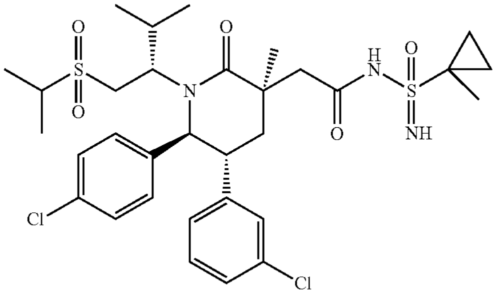 peak 1 isomer in HPLC |
| 028B | 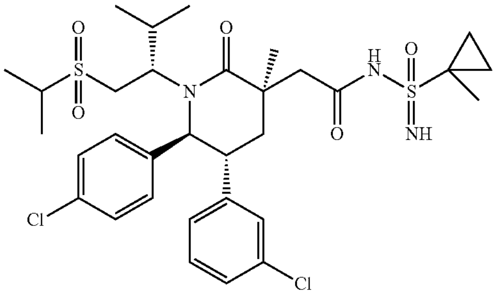 peak 2 isomer in HPLC |

-continued
| number | structure |
|---|---|
| 029 | 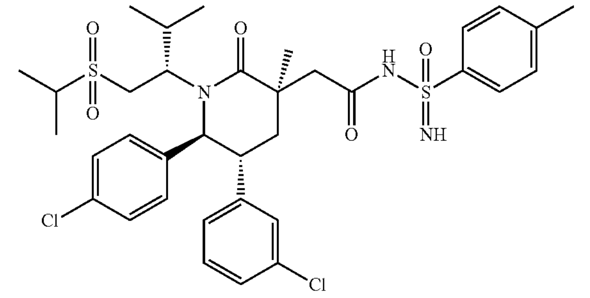 [SMILES: Cc1ccc(S(=N)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1] |
| 030 | 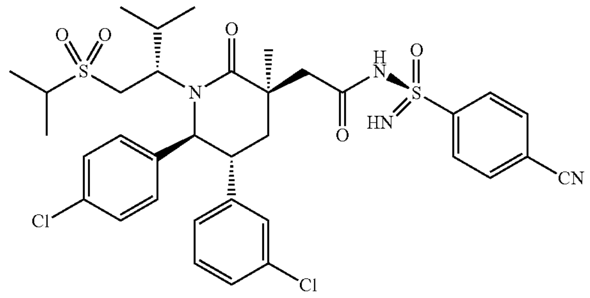 [SMILES: CC(C)[C@@H](CS(=O)(=O)C(C)C)N1C(=O)[C@@](C)(CC(=O)N[S@@](=N)(=O)c2ccc(C#N)cc2)C[C@H](c2cccc(Cl)c2)[C@H]1c1ccc(Cl)cc1] |
| 031 | 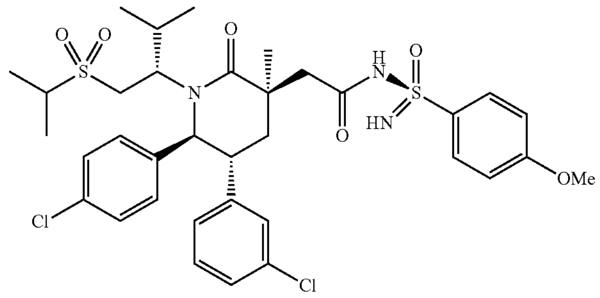 [SMILES: COc1ccc([S@](=N)(=O)NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1] |
| 034 | 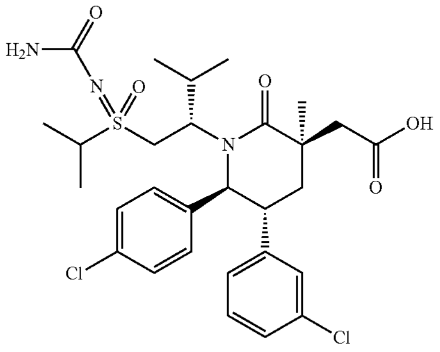 |
| 035 | 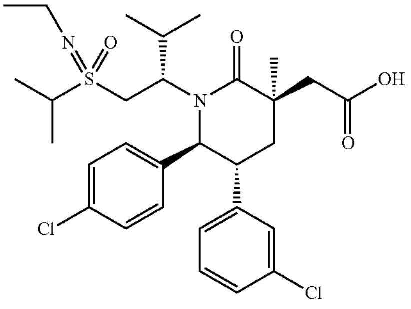 [SMILES: CCN=S(=O)(C[C@H](C(C)C)N1C(=O)[C@@](C)(CC(=O)O)C[C@H](c2cccc(Cl)c2)[C@H]1c1ccc(Cl)cc1)C(C)C] |

-continued
| number | structure |
| --- | --- |
| 039 | 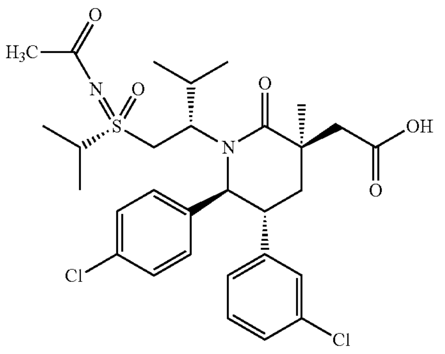 [SMILES: CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] |
| 040 | 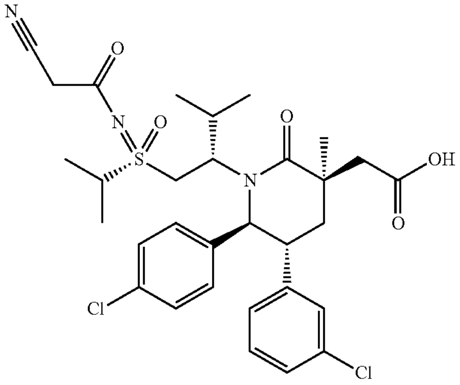 [SMILES: CC(C)[C@@H](C[S@](=O)(=NC(=O)CC#N)C(C)C)N1C(=O)[C@@](C)(CC(=O)O)C[C@H](c2cccc(Cl)c2)[C@H]1c1ccc(Cl)cc1] |
| 041 | 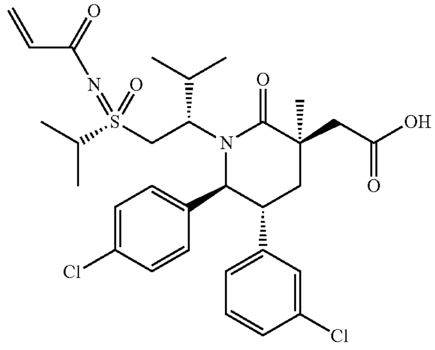 [SMILES: C=CC(=O)N=[S@@](=O)(C[C@H](C(C)C)N1C(=O)[C@@](C)(CC(=O)O)C[C@H](c2cccc(Cl)c2)[C@H]1c1ccc(Cl)cc1)C(C)C] |
| 042 | 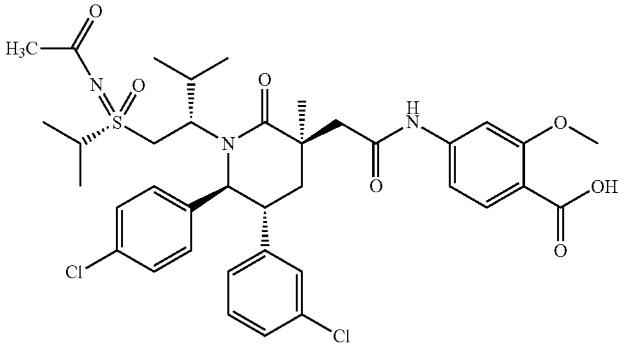 [SMILES: COc1cc(NC(=O)C[C@@]2(C)C[C@H](c3cccc(Cl)c3)[C@@H](c3ccc(Cl)cc3)N([C@H](C[S@](=O)(=NC(C)=O)C(C)C)C(C)C)C2=O)ccc1C(=O)O] |

-continued
| number | structure |
|---|---|
| 043 | 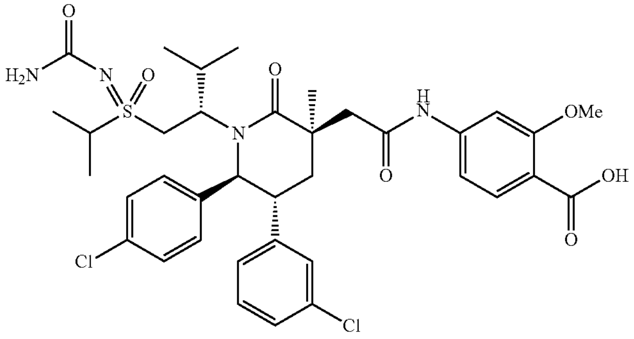 [SMILES: COc1cc(NC(=O)C[C@@]2(C)C[C@H](c3cccc(Cl)c3)[C@@H](c3ccc(Cl)cc3)N([C@H](CS(=O)(=NC(N)=O)C(C)C)C(C)C)C2=O)ccc1C(=O)O] |
| 045 | 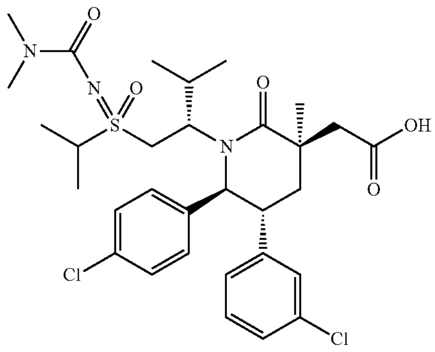 [SMILES: CC(C)[C@@H](CS(=O)(=NC(=O)N(C)C)C(C)C)N1C(=O)[C@@](C)(CC(=O)O)C[C@H](c2cccc(Cl)c2)[C@H]1c1ccc(Cl)cc1] |
| 046 | 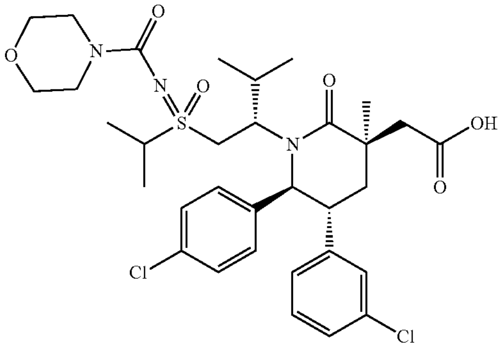 [SMILES: CC(C)[C@@H](CS(=O)(=NC(=O)N1CCOCC1)C(C)C)N1C(=O)[C@@](C)(CC(=O)O)C[C@H](c2cccc(Cl)c2)[C@H]1c1ccc(Cl)cc1] |
| 047 | 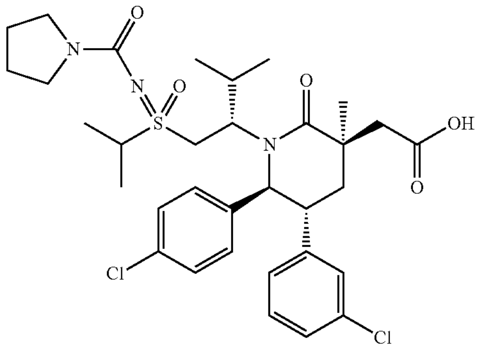 [SMILES: CC(C)[C@@H](CS(=O)(=NC(=O)N1CCCC1)C(C)C)N1C(=O)[C@@](C)(CC(=O)O)C[C@H](c2cccc(Cl)c2)[C@H]1c1ccc(Cl)cc1] |

-continued
| number | structure |
|---|---|
| 048 | 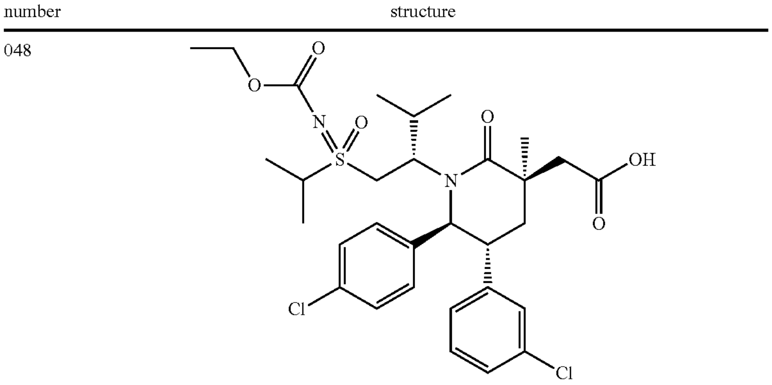 |
| 049 | 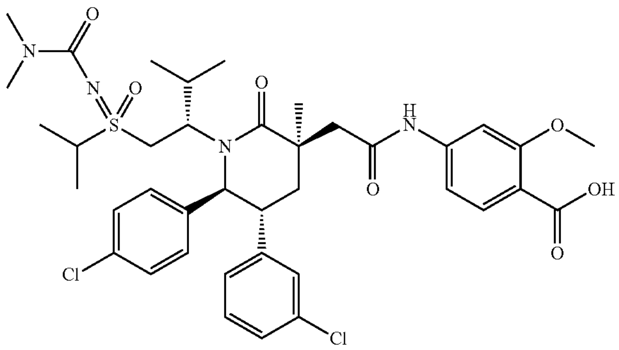 |
| 050 | 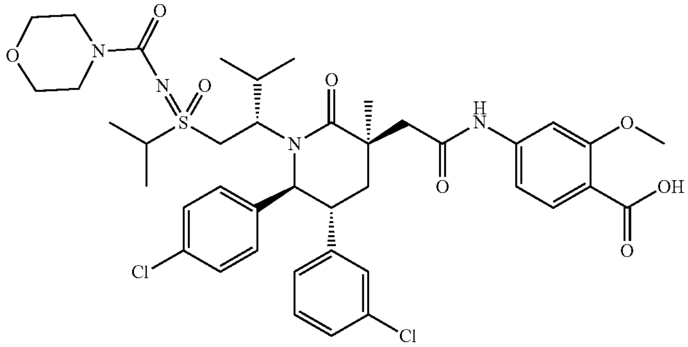 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCOCC3)C(C)C)C(C)C)C2=O)ccc1C(=O)O] |
| 051 | 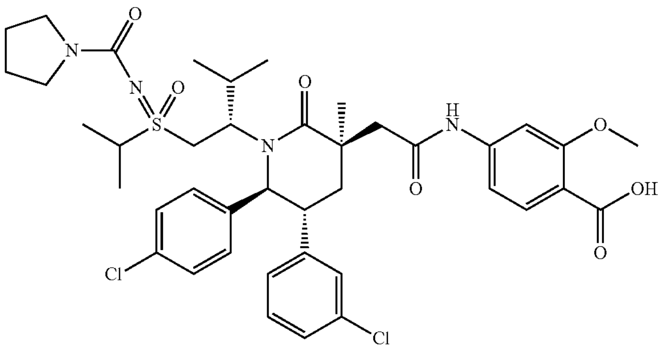 [SMILES: COc1cc(NC(=O)C[C@@]2(C)C[C@H](c3cccc(Cl)c3)[C@@H](c3ccc(Cl)cc3)N([C@H](CS(=O)(=NC(=O)N3CCCC3)C(C)C)C(C)C)C2=O)ccc1C(=O)O] |

-continued
| number | structure |
|---|---|
| 052 | 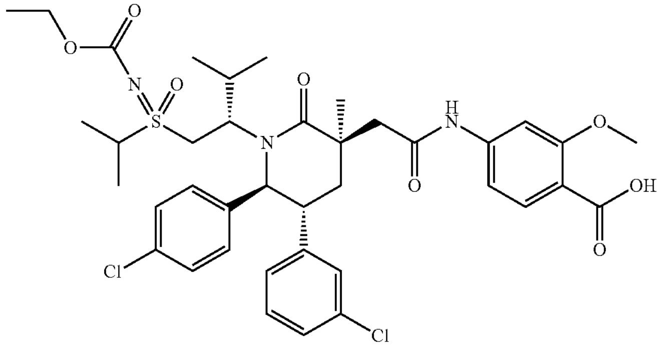 [SMILES: CCOC(=O)N=S(=O)(C[C@H](C(C)C)N1C(=O)[C@@](C)(CC(=O)Nc2ccc(C(=O)O)c(OC)c2)C[C@H](c2cccc(Cl)c2)[C@H]1c1ccc(Cl)cc1)C(C)C] |
| 053 | 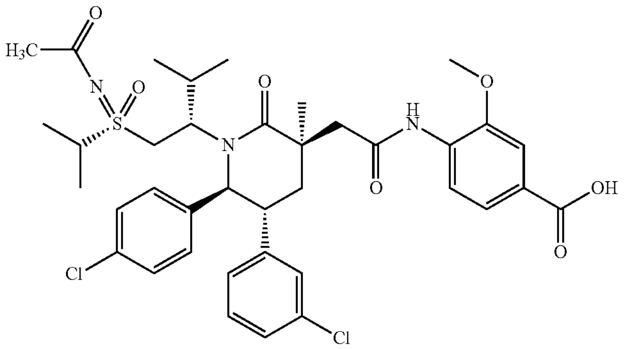 [SMILES: COc1cc(C(=O)O)ccc1NC(=O)C[C@@]1(C)C[C@H](c2cccc(Cl)c2)[C@@H](c2ccc(Cl)cc2)N([C@H](C[S@](=O)(=NC(C)=O)C(C)C)C(C)C)C1=O] |
| 054 | 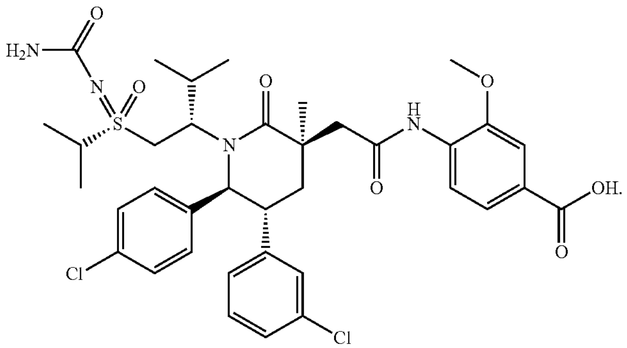 [SMILES: COc1cc(C(=O)O)ccc1NC(=O)C[C@@]1(C)C[C@H](c2cccc(Cl)c2)[C@@H](c2ccc(Cl)cc2)N([C@H](C[S@](=O)(=NC(N)=O)C(C)C)C(C)C)C1=O] |

6. A method of preparing the compound of Formula I of claim 1, wherein the method comprises, or is through step 1, step 2 or step 3:

Step 1:

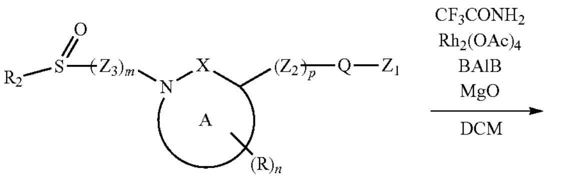

I-1

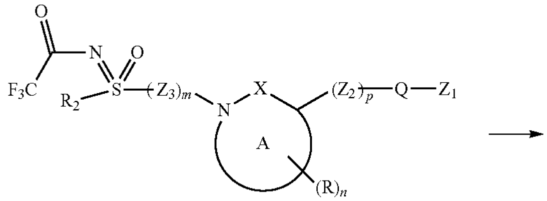

I-2

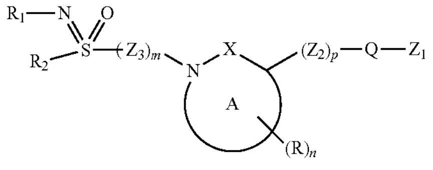

I-3

Step 2:

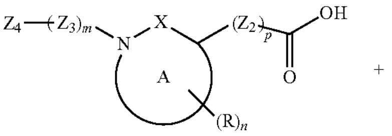

I-4

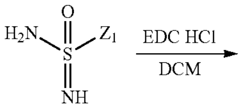

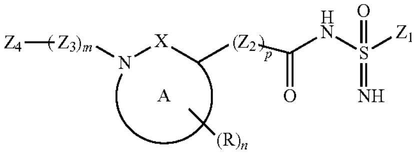

I-5

Step 3:

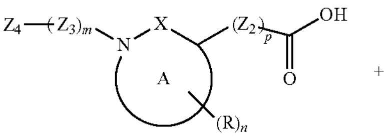

I-4

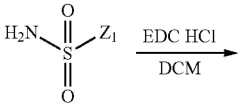

-continued

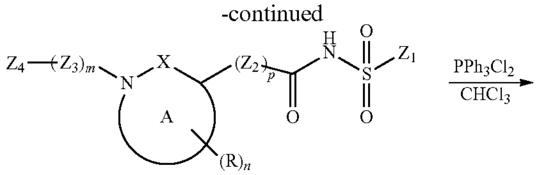

I-6

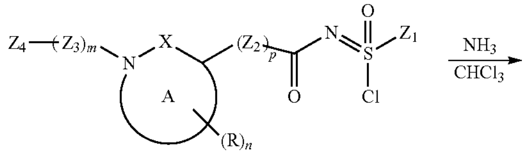

I-7

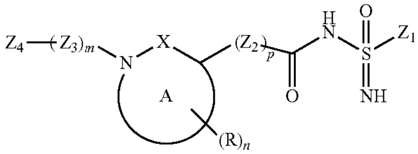

I-5 wherein, each group is defined as described in claim 1.

7. A pharmaceutical composition, comprising (1) the compound as of claim 1 or stereoisomers or tautomers thereof, or pharmaceutically acceptable salts, hydrates or solvates thereof; (2) a pharmaceutically acceptable carrier.

8. A method of treating diseases related to the activity or expression of MDM2 in a subject in need thereof, wherein the diseases related to the activity or expression of MDM2 is selected from the group consisting of bladder cancer, breast cancer, colon cancer, rectal cancer, kidney cancer, liver cancer, lung cancer, small cell lung cancer and non-small cell lung cancer, esophageal cancer, gallbladder cancer, ovarian cancer, pancreatic cancer, gastric cancer, cervical cancer, thyroid cancer, prostate cancer and skin cancer, squamous cell carcinoma; lymphatic lineage hematopoietic system tumors, leukemia, acute lymphocytic leukemia, chronic myeloid leukemia, acute lymphoblastic leukemia, B-cell lymphoma, T-cell lymphoma, Hodgkin's lymphoma, non Hodgkin's lymphoma, hair cell lymphoma and Burkitt's lymphoma, bone marrow lineage hematopoietic system tumors, acute and chronic myeloid leukemia, myelodysplastic syndrome and promyelocytic leukemia; mesenchymal neoplasms, fibrosarcoma and rhabdomyosarcoma and other sarcomas, soft tissue sarcoma and osteosarcoma; central and peripheral nervous system tumors, astrocytoma, neuroblastoma, glioma and neurosarcoma; other tumors, melanoma, seminoma, teratoma, osteosarcoma, xerodermapigmentosum, keratoacanthoma, follicular thyroid cancer and Kaposi's sarcoma, endometrial cancer, head and neck cancer, glioblastoma, malignant ascites, hematopoietic system cancer, thyroid hyperplasia, grave's disease, cyst, asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis, Huntington's disease, inflammatory disease, hypoxia, ulcer, viral infection, bacterial infection and bacterial septicemia, the method comprising administering to the subject an effective amount of the pharmaceutical composition of claim 7.

9. An MDM2 inhibitor, wherein the inhibitor comprises the compound of claim 1, or stereoisomers or tautomers thereof, or pharmaceutically acceptable salts, hydrates or solvates thereof.

10. A method of inhibiting MDM2 activity and expression in vitro comprising contacting the compound of claim 1, or stereoisomers or tautomers thereof, or pharmaceutically acceptable salts, hydrates or solvates thereof with MDM2 protein.

* * * * *